_US005761334A_

United States Patent [19]
Nakajima et al.

[11] Patent Number: 5,761,334
[45] Date of Patent: Jun. 2, 1998

[54] APPARATUS FOR COMPUTER AIDED DIAGNOSIS OF MEDICAL IMAGES HAVING ABNORMAL PATTERNS

[75] Inventors: Nobuyoshi Nakajima; Hideya Takeo; Masahiko Yamada, all of Kanagawa-ken, Japan

[73] Assignee: Fuji Photo Film Co.,Ltd., Kanagawa, Japan

[21] Appl. No.: 590,192

[22] Filed: Jan. 23, 1996

[30] Foreign Application Priority Data

| Jan. 23, 1995 | [JP] | Japan | 7-042277 |
| Apr. 20, 1995 | [JP] | Japan | 7-094693 |
| Dec. 5, 1995 | [JP] | Japan | 7-316679 |

[51] Int. Cl.$^6$ ............................................. G06K 9/00
[52] U.S. Cl. .................................... 382/132; 382/311
[58] Field of Search ............................. 382/128, 132, 260, 274, 311; 128/922

[56] References Cited

U.S. PATENT DOCUMENTS

| 4,571,635 | 2/1986 | Mahmoodi et al. | 358/284 |
| 4,907,156 | 3/1990 | Doi et al. | 364/413.13 |
| 5,133,020 | 7/1992 | Giger et al. | 382/6 |
| 5,231,580 | 7/1993 | Cheung et al. | 364/413.13 |
| 5,311,428 | 5/1994 | Hayes et al. | 364/413.13 |
| 5,467,404 | 11/1995 | Vuylsteke et al. | 382/274 |

FOREIGN PATENT DOCUMENTS

| 357842 | 3/1990 | European Pat. Off. | G06F 15/68 |
| 0507485 | 10/1992 | European Pat. Off. | G01T 1/29 |
| 0610916 | 8/1994 | European Pat. Off. | G06F 15/68 |
| 61-169971 | 7/1986 | Japan | G06F 15/62 |
| 2-1078 | 1/1990 | Japan | G06F 15/68 |
| WO 90/07751 | 7/1990 | WIPO | G06F 15/68 |
| 91/07135 | 5/1991 | WIPO | 382/128 |

OTHER PUBLICATIONS

Spiesberger, "Mammogram Inspection by Computer," *IEEE Transactions on Biomedical Engineering*, vol. BME-26, No. 4, Apr. 1979, pp. 213-219.

"Detection of Tumor Patterns in DR Images (Iris Filter)" *Collected Papers of the Institute of Electronics and Communication Engineers of Japan*, D-II, vol. J75-D-II, No. 3, pp. 663-670, Mar., 1992.

"Extraction of Small Calcified Patterns with a Morphology Filter Using a Multiply Structure Element" *Collected Papers of the Institute of Electronics and Communication Engineers of Japan*, D-II, vol. J75-D-II, No. 7, pp. 1170-1176, Jul., 1992.

Fundamentals of Morphology and Its Application to Mammogram Processing, *Medical Imaging Technology*, vol. 12, No. 1, pp. 59-66, Jan., 1994.

*Primary Examiner*—Andrew W. Johns
*Attorney, Agent, or Firm*—Sughrue, Mion, Zinn, Macpeak & Seas, PLLC

[57] ABSTRACT

An apparatus for computer aided diagnosis of images comprises an entire area image memory for storing an entire area image signal representing a radiation image of an object, and a prospective abnormal pattern detecting device for detecting a prospective abnormal pattern in the radiation image in accordance with the entire area image signal. A judgment device makes a judgment as to the presence or absence of the prospective abnormal pattern in accordance with the results of the detection of the prospective abnormal pattern carried out by the prospective abnormal pattern detecting device. In cases where the judgment device has judged that the prospective abnormal pattern is present, a local area extracting device extracts a local area limited image signal corresponding to a local area containing the prospective abnormal pattern from the entire area image signal having been stored in the entire area image memory. A local area limited image displaying device displays the image of the local area in accordance with the local area limited image signal, which has been extracted by the local area extracting device. An entire area image displaying device displays the entire area of the radiation image of the object in accordance with the entire area image signal.

50 Claims, 28 Drawing Sheets

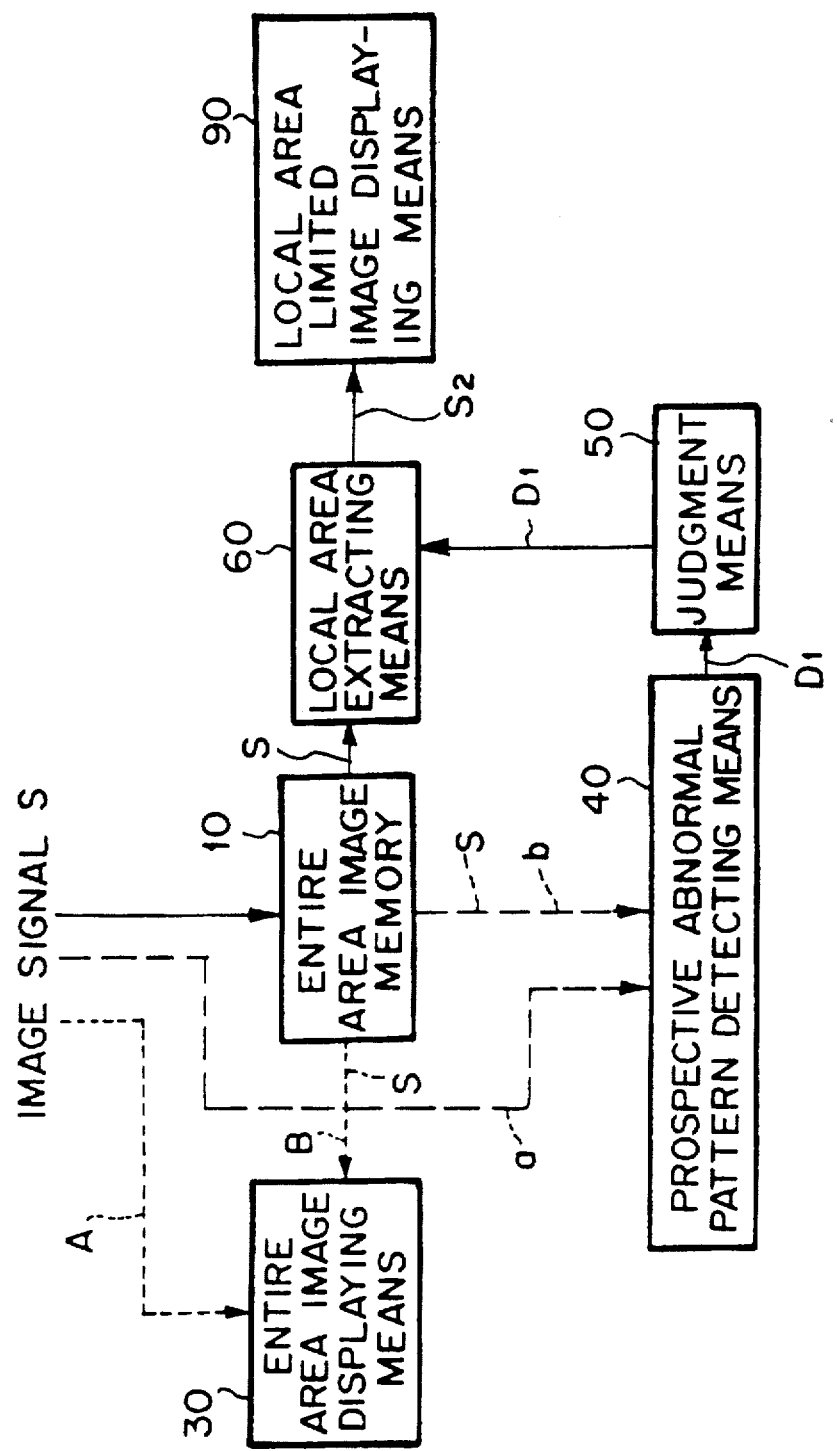

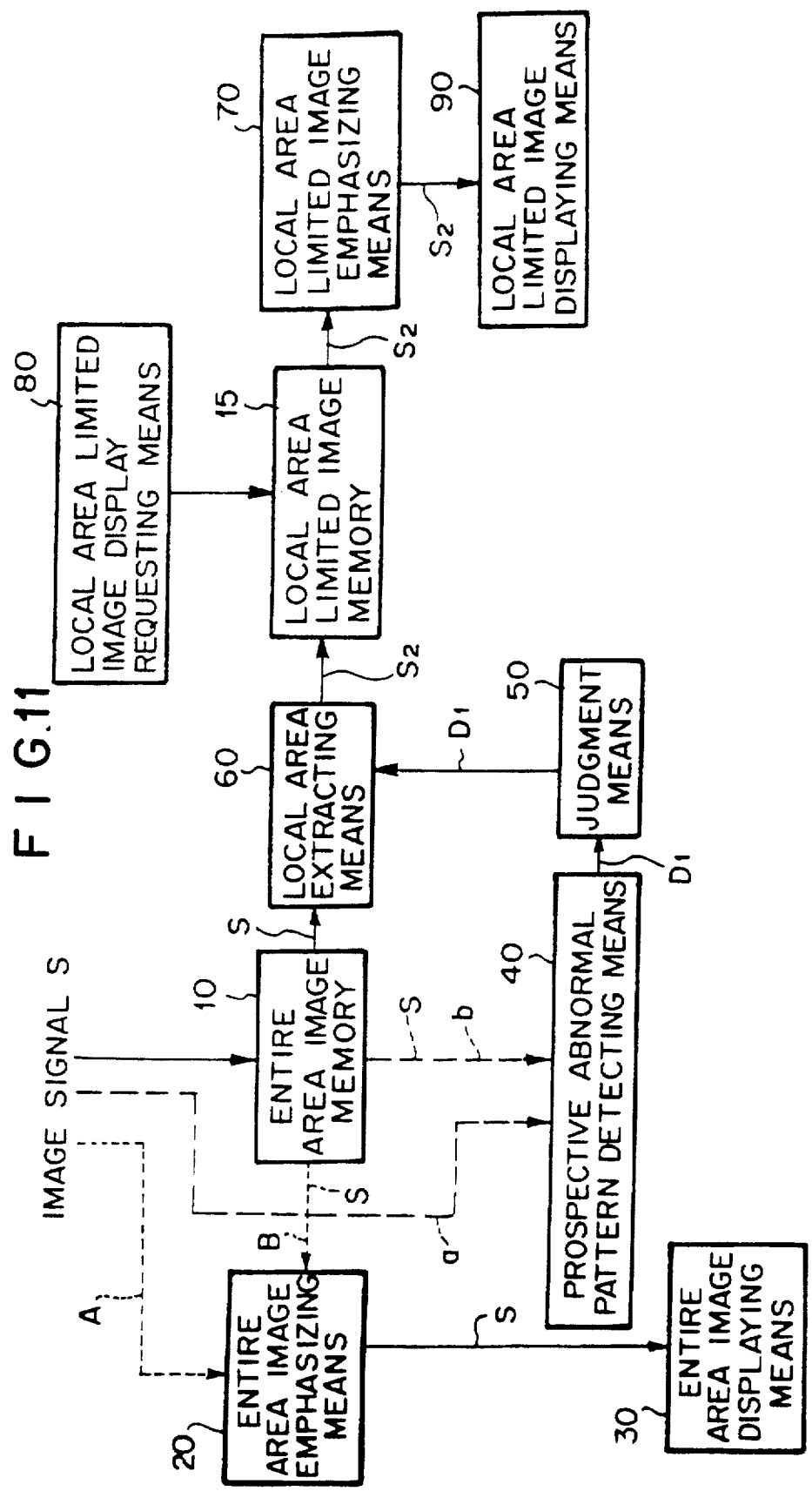
F I G.11

| $f_7$ | $f_6$ | $f_5$ | $f_4$ | $f_3$ |
|---|---|---|---|---|
| $f_8$ | | | | $f_2$ |
| $f_9$ | | | | $f_1$ |
| $f_{10}$ | | | | $f_{16}$ |
| $f_{11}$ | $f_{12}$ | $f_{13}$ | $f_{14}$ | $f_{15}$ |

PICTURE ELEMENT j

PICTURE ELEMENT (x,y) LOCATED ALONG THE RADIAL LINE EXTENDING FROM THE PICTURE ELEMENT OF INTEREST

PICTURE ELEMENT OF INTEREST (k,ℓ)

POSITION IN DIRECTION OF LINE I-I

APPARATUS FOR COMPUTER AIDED DIAGNOSIS OF MEDICAL IMAGES HAVING ABNORMAL PATTERNS

BACKGROUND OF THE INVENTION

1. Field of the Invention

This invention relates to an apparatus for computer aided diagnosis of images, wherein an abnormal pattern in a radiation image of an object is detected from an image signal representing the radiation image and displayed for use as a tool in, particularly, the diagnosis of an illness.

2. Description of the Prior Art

Techniques for reading out a radiation image of an object and reproducing a visible radiation image have heretofore been carried out in various fields. With the techniques, a radiation image of an object, which has been recorded on a recording medium, such as a stimulable phosphor sheet or X-ray film, is read out, an image signal is thereby obtained, and the obtained image signal is subjected to appropriate image processing and then used for reproducing a visible image on a display device, or the like. In particular, recently, various digital radiography techniques, which utilize computers and are referred to as computed radiography, have been proposed and applied to clinical diagnoses, or the like.

The digital radiography has features drastically different from the conventional analog type of radiography in that an image signal can be analyzed quantitatively. Particularly for medical diagnoses of human bodies, techniques referred to as the computer aided diagnosis of medical images (CADM) have been proposed, which aim at more positively utilizing the features of the digital radiography.

The techniques for the computer aided diagnosis of medical images, or the like, assist in making diagnoses by reading patterns in an image at the sites of medical treatment. Specifically, in the past, medical specialists visually read patterns in radiation images having been reproduced on recording media, such as X-ray film, display devices, such as cathode ray tube (CRT) display devices, or the like, and made efforts in order to find out abnormal tumor patterns, which represented cancers, or the like, high-density small calcified patterns, and the like, in the early stages of the diseases. (The tumor patterns, small calcified patterns, and the like, will hereinbelow be referred to as the abnormal patterns.) However, in such cases, there is the risk that the abnormal patterns are left unnoticed or are misunderstood due to subjective judgments, depending on differences between the image understanding capabilities of persons, who view the radiation images.

Therefore, the techniques for the computer aided diagnosis of medical images aim at preventing the persons, who view the radiation images, from failing to notice the abnormal patterns and misunderstanding the abnormal patterns, and thereby aim at enabling the persons to make the efficient and accurate diagnosis of an illness. For such purposes, with the techniques for computer aided diagnosis of medical images, a prospective abnormal pattern, which is considered as being an abnormal pattern, is detected. Also, a marking is put on the detected portion in order to arouse an attention of the person, who views the radiation image. Alternatively, characteristics of the detected prospective abnormal pattern are indicated quantitatively as materials, which are useful for objective judgments of the person, who views the radiation image. Reference should be made to "Detection of Tumor Patterns in DR Images (Iris Filter)," Obata, et al., Collected Papers of The Institute of Electronics and Communication Engineers of Japan, D-II, Vol. J75-D-II, No. 3, pp. 663–670, Mar. 1992; and "Extraction of Small Calcified Patterns with A Morphology Filter Using A Multiply Structure Element," Obata, et al., Collected Papers of The Institute of Electronics and Communication Engineers of Japan, D-II, Vol. J75-D-II, No. 7, pp. 1170–1176, Jul. 1992.

As described above, with the proposition concerning the techniques for computer aided diagnosis of medical images, a marking is merely put on a prospective abnormal pattern in a reproduced image, or a quantitative rating scale is merely indicated For the prospective abnormal pattern.

The marking and the rating scale are efficient to arouse an attention of the person, who views the radiation image, or to prevent the person from misunderstanding the abnormal pattern due to subjective judgments. However, in order for the person, who views the radiation image, to actually make a diagnosis of the site of the abnormal pattern, it is necessary to provide an image, which has good image quality and can serve as an effective tool in the efficient and accurate diagnosis of an illness.

Image processing, such as gradation processing or frequency processing, has heretofore been carried out on an image signal, which represents an image and has been obtained with one of various image obtaining methods, such that a visible image having good image quality can be reproduced and used as an effective tool in, particularly, the accurate and efficient diagnosis of an illness.

Particularly, in the field of medical images, such as radiation images of human bodies serving as objects, it is necessary for specialists, such as doctors, to make an accurate diagnosis of an illness or an injury of the patient in accordance with the obtained image. Therefore, it is essential to carry out the image processing in order that a visible image having good image quality can be reproduced and used as an effective tool in the accurate and efficient diagnosis of an illness.

As one of the image processing, frequency emphasis processing has been disclosed in, for example, Japanese Unexamined Patent Publication No. 61(1986)-169971. With the disclosed frequency emphasis processing, an image signal (i.e., an original image signal) Dorg representing the image density value of an original image is converted into an image signal Dproc with Formula (25).

$$Dproc = Dorg + \beta \times (Dorg - Dus) \tag{25}$$

wherein $\beta$ represents the frequency emphasis coefficient, and Dus represents the unsharp mask signal. The unsharp mask signal Dus comprises a super-low frequency component obtained by setting a mask, i.e. an unsharp mask, constituted of a picture element matrix, which has a size of N columns ×N rows (wherein N represents an odd number) and has its center at the picture element represented by the original image signal Dorg, in a two-dimensional array of picture elements. The unsharp mask signal Dus is calculated with, for example, formula (2)

$$Dus = (\Sigma Dorg)/N^2 \tag{2}$$

wherein $\Sigma Dorg$ represents the sum of the image signal values representing the picture elements located within the unsharp mask.

The value of (Dorg-Dus) in the parenthesis of the second term of Formula (25) is obtained by subtracting the unsharp mask signal, which represents the super-low frequency component, from the original image signal. Therefore, a comparatively high frequency component can be extracted selectively by subtracting the super-low frequency component from the original image signal. The comparatively high frequency component is then multiplied by the frequency emphasis coefficient β, and the obtained product Is added to the original image signal. In this manner, the comparatively high frequency component can be emphasized.

As described above, in order that a visible image having good image quality can be reproduced and used as an effective tool in, particularly, the accurate and efficient diagnosis of an illness, it is essential to carry out the image processing on the given image. However, as disclosed in, for example, Japanese Unexamined Patent Publication No. 2(1990)-1078, in cases where the emphasis processing merely depending on the image density is carried out, components adversely affecting the image quality, such as radiation noise components in a mammogram, are also emphasized. As a result, the image quality of the image and its capability of serving as an effective tool in, particularly, the efficient and accurate diagnosis of an illness become low.

Also, as disclosed in, for example, U.S. Pat. No. 4,571, 635, EP 359842 A1, and WO 90/07731, in cases where emphasis processing depending upon the value of variance of an image signal is carried out, an image portion having a locally large change in density is emphasized to a high extent. Therefore, the problems occur in that undershooting and overshooting become relatively perceptible in the vicinity of the image portion. Particularly, as for X-ray images, an artifact is apt to occur on the high density side.

SUMMARY OF THE INVENTION

The primary object of the present invention is to provide an apparatus for computer aided diagnosis of images, wherein a visible image having good image quality is reproduced and used as an effective tool in, particularly, the accurate and efficient diagnosis of an illness.

Another object of the present invention is to provide an apparatus for computer aided diagnosis of images, wherein a reproduced visible image is obtained such that components unnecessary for a diagnosis, or the like, such as noise components, may not be emphasized, only a specific image portion of interest may be efficiently emphasized, and the occurrence of an artifact may be restricted.

The present invention provides a first apparatus for computer aided diagnosis of images, comprising:

i) an entire area image storing means for storing an entire area image signal representing a radiation image of an object, ii) a prospective abnormal pattern detecting means for detecting a prospective abnormal pattern in the radiation image in accordance with the entire area image signal, iii) a judgment means for making a judgment as to the presence or absence of the prospective abnormal pattern in accordance with the results of the detection of the prospective abnormal pattern carried out by the prospective abnormal pattern detecting means, iv) a local area extracting means which, in cases where the judgment means has judged that the prospective abnormal pattern is present, extracts a local area limited image signal corresponding to a local area containing the prospective abnormal pattern from the entire area image signal having been stored in the entire area image storing means, v) a local area limited image displaying means for displaying the image of the local area in accordance with the local area limited image signal, which has been extracted by the local area extracting means, and vi) an entire area image displaying means for displaying the entire area of the radiation image of the object in accordance with the entire area image signal.

The term "abnormal pattern" as used herein means the pattern representing one of various symptoms. For example, in the cases of medical X-ray images of the chests and mammograms, the term "abnormal pattern" means the pattern representing one of various symptoms of cancers, and the like, such as a neoplasm, a tumor, calcification, hypertrophy of the pleura, and pneumothorax, which are not found in normal patterns, such as blood vessel patterns. The prospective abnormal pattern detecting means need not necessarily be constituted in order to detect all of these abnormal patterns. For example, the prospective abnormal pattern detecting means may be constituted in order to detect only the tumor pattern or only the calcified pattern as the abnormal pattern. Alternatively, the prospective abnormal pattern detecting means may be constituted in order to detect two or more kinds of abnormal patterns among the above-enumerated abnormal patterns. For example, in cases where the processing for detecting the prospective abnormal pattern, which is carried out by the prospective abnormal pattern detecting means, is based upon the algorithm of an iris filter (hereinbelow referred to simply as the iris filter processing), a tumor pattern is detected as the abnormal pattern. In cases where the detection processing of the prospective abnormal pattern detecting means is based upon the algorithm of morphology (hereinbelow referred to simply as the morphology processing), a calcified pattern is detected as the abnormal pattern.

The term "prospective abnormal pattern" as used herein means a true abnormal pattern and a pattern, which is similar to the abnormal pattern and has the same characteristics as the tumor pattern, the calcified pattern, or the like, from the viewpoint of the image characteristics found in the tumor pattern, the calcified pattern, or the like, but which is not clearly determined as being the abnormal pattern and should ultimately be judged by the person, who views the radiation image.

The term "local area containing a prospective abnormal pattern" as used herein means the region, which is located in the vicinity of the prospective abnormal pattern and contains the prospective abnormal pattern. The peripheral edge shape of the local area may take one of various shapes, such as a rectangle, a circle, and an ellipse. Therefore, the local area limited image displaying means displays the prospective abnormal pattern itself and the image of the region in the vicinity of it.

Accordingly, the entire area image can be assumed easily from the image of the region in the vicinity of the prospective abnormal pattern, and the position of the prospective abnormal pattern in the entire area image can be determined easily.

The first apparatus for computer aided diagnosis of images in accordance with the present invention may further comprise:

a local area limited image storing means, which is located between the local area extracting means and the local area limited image displaying means and which temporarily stores the local area limited image signal, and a local area limited image display requesting means, which is located between the local area extracting means and the local area limited image displaying means and which, only when a predetermined image display request is received from the exterior, causes the local area limited image signal to be fed out from the local area limited image storing means and causes the image of the local area to be displayed on the local area limited image displaying means.

With this constitution, in cases where the abnormal pattern is detected, the local area limited image signal, which represents the image of the local area containing the abnormal pattern, is temporarily stored in the local area limited image storing means. Also, when necessary, the person, who views the radiation image, can make a request for displaying the local area limited image.

The first apparatus for computer aided diagnosis of images in accordance with the present invention may further comprise a local area limited image emphasizing means for carrying out image emphasis processing on at least the abnormal pattern image signal, which represents the prospective abnormal pattern and is among the local area limited image signal, such that the image of the prospective abnormal pattern in the image of the local area, which is displayed on the local area limited image displaying means, may have better image quality and higher capability of serving as an effective tool in, particularly, the efficient and accurate diagnosis of an illness than the radiation image (hereinbelow referred to simply as the entire area image), which is displayed on the entire area image displaying means. With the local area limited image emphasizing means, the image emphasis processing is carried out on the local area limited image signal, particularly the abnormal pattern image signal in the local area limited image signal. In this manner, the image of the local area, particularly the image of the prospective abnormal pattern can be displayed such that it may have better image quality and higher capability of serving as an effective tool in, particularly, the efficient and accurate diagnosis of an illness than the entire area image. Therefore, the efficiency and the accuracy of the diagnosis, or the like, can be kept high.

The entire area image, which is displayed on the entire area image displaying means, may be reproduced on the entire area image displaying means from the entire area image signal, which has not been subjected to image processing. Alternatively, in cases where the first apparatus for computer aided diagnosis of images in accordance with the present invention further comprises an entire area image emphasizing means for carrying out image emphasis processing, such as gradation processing or frequency processing, on the entire area image signal, the entire area image may be reproduced on the entire area image displaying means from the entire area image signal, which has been obtained from the image emphasis processing.

Specifically, the local area limited image emphasizing means may be constituted in order to carry out the image emphasis processing on the local area limited image signal, particularly the abnormal pattern image signal, such that the image of the local area, which is displayed on the local area limited image displaying means, particularly the image of the prospective abnormal pattern, may have better image quality and higher capability of serving as an effective tool in, particularly, the efficient and accurate diagnosis of an illness than the entire area image, which is ultimately displayed on the entire area image displaying means, regardless of whether the image emphasis processing is or is not carried out on the entire area image signal.

As the image emphasis processing carried out by the local area limited image emphasizing means, for example, one of the gradation processing, the frequency processing, and the enlargement processing, or a combination of two or more of them may be employed.

In cases where the gradation processing is employed as the image emphasis processing, the gradation processing should preferably be set such that the level of contrast of the image of the local area, which is displayed on the local area limited image displaying means, or the image of the prospective abnormal pattern in the local area may become at least 1.2 times as high as the level of contrast of the entire area image, which is displayed on the entire area image displaying means.

In cases where the frequency processing is employed as the image emphasis processing, the frequency processing should preferably be set such that the degree of emphasis of the image of the local area, which is displayed on the local area limited image displaying means, or the image of the prospective abnormal pattern in the local area may become at least 1.1 times as high as the degree of emphasis of the entire area image, which is displayed on the entire area image displaying means. The frequency processing should more preferably be set such that the degree of emphasis of at least the image of the prospective abnormal pattern in the image of the local area, which is displayed on the local area limited image displaying means, may become at least 1.1 times as high as the degree of emphasis of the entire area image, which is displayed on the entire area image displaying means.

Also, in cases where the enlargement processing is employed as the image emphasis processing, the enlargement processing should preferably be set such that the display size of the image of the local area, which is displayed on the local area limited image displaying means, or the image of the prospective abnormal pattern in the image of the local area may become at least 1.5 times as large as the display size of the image of the local area or the image of the prospective abnormal pattern in the entire area image, which is displayed on the entire area image displaying means.

The enlargement processing may be set such that the scale of enlargement may be constant as described above, or such that the scale of enlargement may be changed in accordance with the size of the prospective abnormal pattern detected by the prospective abnormal pattern detecting means, for example, the peripheral edge length of the tumor pattern or the calcified pattern, or the total sum or the mean value of the number of picture elements located within the calcified pattern detected with the morphology processing, which will be described later. Specifically, when the prospective abnormal pattern is displayed on the local area limited image displaying means, in cases where the size of the detected prospective abnormal pattern is small, the enlargement processing may be carried out with a comparatively large scale of enlargement. In cases where the size of the detected prospective abnormal pattern is large, the enlargement processing may be carried out with a comparatively small scale of enlargement. Thus the enlargement processing may be carried out such that the apparent size of the prospective abnormal pattern on the display surface of the local area limited image displaying means may become approximately equal to a predetermined size regardless of the actual size of the prospective abnormal pattern.

Specifically, the local area limited image emphasizing means may comprise (a) an abnormal pattern size calculating means for calculating the size of the prospective abnormal pattern in accordance with a signal representing the position of the prospective abnormal pattern, which signal has been obtained from the prospective abnormal pattern detecting means, (b) an enlargement scale setting table, in which the scale of enlargement in accordance with the size of the prospective abnormal pattern calculated by the abnormal pattern size calculating means has been set previously such that the size of the image of the prospective abnormal pattern displayed on the local area limited image displaying means may become approximately equal to a predetermined size, and (c) an enlargement processing means for carrying out the enlargement processing on the local area limited image signal or the abnormal pattern image signal.

In this manner, the scale of enlargement may be changed such that the size of the prospective abnormal pattern displayed on the local area limited image displaying means may become approximately equal to a predetermined size regardless of the size of the prospective abnormal pattern detected. In such cases, even if the size of the prospective abnormal pattern detected is small, the prospective abnormal pattern can be viewed as an image having a size approximately equal to a predetermined size. Therefore, the efficiency and the accuracy of the diagnosis, or the like, can be kept high.

The first apparatus for computer aided diagnosis of images in accordance with the present invention may further comprise an entire area image emphasizing means for carrying out predetermined image emphasis processing on the entire area image signal. In cases where the image emphasis processing, such as the gradation processing or the frequency processing, is carried out on the entire area image signal by the entire area image emphasizing means, the image quality of the entire area image and its capability of serving as an effective tool in, particularly, the efficient and accurate diagnosis of an illness can be kept high.

The entire area image displaying means may also serve as the local area limited image displaying means, and the local area limited image may be displayed at a portion of the display surface of the entire area image displaying means. Specifically, while the image of the entire area of the radiation image (i.e., the entire area image) is being displayed on the entire area image displaying means, the local area limited image, which will otherwise be displayed on an independent local area limited image displaying means, may be displayed at a portion of the entire area image, which is being displayed on the entire area image displaying means. (This means that, at the portion of the display surface of the entire area image displaying means, at which portion the local area limited image is displayed, the portion of the entire area image and the local area limited image are not superposed one upon the other, but instead only the local area limited image is displayed without the portion of the entire area image being displayed. At the other portion of the display surface of the entire area image displaying means, the remaining portion of the entire area image is displayed.) Specifically, a window region, the contour of which is rectangular, circular, elliptic, or the like, and in which the local area limited image is to be displayed, may be located at a portion of the display surface of the entire area image displaying means. The local area limited image may be displayed in the window region, and the portion of the entire area image other than the portion corresponding to the window region may be displayed in the region outside of the window region.

The entire area image and the local area limited image may be displayed in various manners in accordance with the kind of the object, the image of which is displayed. Specifically, for example, in cases where the X-ray image of the mamma, or the like, of a single patient is displayed, only the image of the single mamma may be displayed. Alternatively, for example, two entire area image displaying means and/or two local area limited image displaying means may be provided. In this manner, the local area limited image containing the abnormal pattern in one of the two mammae of the patient may be displayed on one of the two image displaying means. At the same time, the local area limited image of the portion of the other mamma, which portion corresponds to the local area of the one mamma, may be displayed on the other image displaying means. In such cases, the person, who views the radiation image, can compare the corresponding portions of the right and left mammae of the single patient.

More specifically, a pair of the entire area images of the right and left mammae of a single patient may be displayed on a single entire area image displaying means. Alternatively, the entire area image of one of the mammae may be displayed on one of two entire area image displaying means, and the entire area image of the other mammae may be displayed on the other entire area image displaying means.

Also, in cases where a prospective abnormal pattern is detected in one of the mammae, the local area limited image containing the prospective abnormal pattern in the one mamma and the image of the local area in the other mamma, which local area corresponds to the portion of the local area in the one mamma, may be displayed in pair on a single local area limited image displaying means, or may be respectively displayed on two local area limited image displaying means. In such cases, the same local area limited image emphasis processing should preferably be carried out on the images of the local areas in the pair of the mammae of the single patient.

Further, in cases where the entire area image displaying means also serves as the local area limited image displaying means, a pair of the entire area images of the right and left mammae of the single patient may be displayed on one or two entire area image displaying means, and the images of the corresponding local areas of the right and left mammae may be displayed respectively in the entire area images.

Furthermore, the image of one of the mammae of the single patient and the image of the other mamma, which has been recorded independently of the image of the one mamma, may be simultaneously displayed on the display surface of the same image displaying means. Specifically, the image of the one mamma may be displayed at the right half of the display surface of the entire area image displaying means, and the image of the other mamma may be displayed simultaneously at the left half of the display surface of the same entire area image displaying means, such that the front sides of the two images may stand facing each other, or the back sides of the two images may stand facing each other. In cases where the prospective abnormal pattern is detected from the entire area image signal, which represents the image of the one mamma, the local area limited image containing the prospective abnormal pattern may be subjected to the emphasis processing and then displayed at a portion of the right half of the display surface, i.e., at a portion of the entire area image of the one mamma. Also, the local area limited image of the portion of the other mamma, which portion corresponds to the position of the prospective abnormal pattern in the one mamma, may be displayed at a portion of the left half of the display surface, i.e., at a portion of the entire area image of the other mamma.

As described above, the two images represented by two image signals obtained independently of each other may be displayed on two independent image displaying means or at different display positions on a single image displaying means, such that the same portions of the two images may correspond to each other. In such cases, the first apparatus for computer aided diagnosis of images in accordance with the present invention may further comprise two means for respectively storing the entire area image signal representing one mamma and the entire area image signal representing the other mamma, means for detecting two image signals (the two entire area image signals or the two local area limited image signals) in association with the relationship between the image positions, and a display control means for controlling the storing means and the detection means and causing the images to be displayed on the image display means.

The local area limited image, which is displayed on the entire area image displaying means, may be displayed in a display region different from the local area, which is located in the radiation image displayed on the entire area image displaying means and which corresponds to the image of the local area. In such cases, the local area limited image does not overlap upon the local area in the displayed entire area image. Therefore, the local area limited image can be viewed while the position of the local area in the entire area image is being recognized. As a result, the efficiency and the accuracy of the diagnosis, or the like, can be kept high.

Also, the display region for the local area limited image, which is displayed on the entire area image displaying means, may be determined such that it may be accommodated in a display region, which is different from the object image displayed on the entire area image displaying means. In this manner, the local area limited image can be prevented from overlapping upon the local region in the entire area image and upon the object image in the entire area image.

It is considered that the display region for the local area limited image having been determined in the manner described above will change in size in accordance with the size of the object image displayed on the entire area image displaying means. Specifically, if the region other than the region, in which the object image is displayed, is very small, the display region for the local area limited image will become very small.

In such cases, the size of the local area limited image itself may be reduced in accordance with the size of the display region for the local area limited image. However, in such cases, it is not possible to obtain large effects of extracting and displaying only the local area limited image in order that the local area limited image having good image quality can be reproduced and used as an effective tool in, particularly the accurate and efficient diagnosis of an illness.

Therefore, in cases where the size of the display region for the local area limited image in the entire area image displaying means is smaller than the size of the local area limited image, only a portion of the local area limited image, which is capable of being displayed within the display region for the local area limited image, should preferably be displayed, and the local area limited image should preferably be scrolled within the display region. In such cases, though only a portion of the local area limited image can be displayed at a given instant in the display region, the display region can be utilized as the window, and the local area limited image can be scrolled within the window. In this manner, the necessary portion of the local area limited image can be viewed successively.

The number of the local area limited image displayed simultaneously with the entire area image on the entire area image displaying means is not limited to one. In cases where a plurality of abnormal patterns are detected, the same number of local area limited images as that of the abnormal patterns may be displayed.

As the processing for detecting the prospective abnormal pattern, which is carried out by the prospective abnormal pattern detecting means, the iris filter processing, the morphology processing, or the combination of them may be employed.

With the iris filter, the gradients of image signal values, which are represented by the density values of a radiation image, are calculated as gradient vectors, and information representing the degree of centralization of the gradient vectors Is fed out. The iris filter processing is the technique for detecting a tumor pattern, or the like, in accordance with the calculated degree of centralization of the gradient vectors.

Specifically, it has been known that, for example, in a radiation image recorded on an X-ray film (i.e., an image yielding an image signal of a high signal level for a high image density), the density values of a tumor pattern are slightly smaller than the density values of the surrounding image areas. The gradient vector at an arbitrary picture element located in the tumor pattern is directed toward the vicinity of the center point of the tumor pattern. On the other hand, in an elongated pattern, such as a blood vessel pattern, gradient vectors do not centralize upon a specific point. Therefore, the distributions of the directions of the gradient vectors in local areas may be evaluated, and a region, in which the gradient vectors centralize upon a specific point, may be detected. The thus detected region may be taken as a prospective tumor pattern, which is considered as being a tumor pattern. The processing with the iris filter is based on such fundamental concept. Steps of algorithms of the iris filter will be described hereinbelow. (Step 1) Calculation of gradient vectors For each picture element j among all of the picture elements constituting a given image, the direction θ of the gradient vector of the image signal representing the image is calculated with Formula (8).

$$\theta = \tan^{-1} \frac{(f_3 + f_4 + f_5 + f_6 + f_7) - (f_{11} + f_{12} + f_{13} + f_{14} + f_{15})}{(f_1 + f_2 + f_3 + f_{15} + f_{16}) - (f_7 + f_8 + f_9 + f_{10} + f_{11})} \quad (8)$$

As illustrated in FIG. 18, $f_1$ through $f_6$ in Formula (8) represent the picture element values (i.e., the image signal values) corresponding to the picture elements located at the peripheral areas of a mask, which has a size of five picture elements (located along the column direction of the picture element array)×five picture elements (located along the row direction of the picture element array) and which has its center at the picture element j. (Step 2) Calculation of the degree of centralization of gradient vectors Thereafter, for each picture element among all of the picture elements constituting the given image, the picture element is taken as a picture element of interest, and the degree of centralization C of the gradient vectors with respect to the picture element of interest is calculated with Formula (9).

$$C = (1/N) \sum_{j=1}^{N} \cos \theta_j \quad (9)$$

As illustrated in FIG. 19, in Formula (9), N represents the number of the picture elements located in the region inside of a circle, which has its center at the picture element of interest and has a radius R, and θj represents the angle made between the straight line, which connects the picture element of interest and each picture element j located in the circle, and the gradient vector at the picture element j which gradient vector has been calculated with Formula (8). Therefore, in cases where the directions of the gradient vectors of the respective picture elements j centralize upon the picture element of interest, the degree of centralization C represented by Formula (9) takes a large value.

The gradient vector of each picture element j, which is located in the vicinity of a tumor pattern, is directed approximately to the center portion of the tumor pattern regardless of the level of the contrast of the tumor pattern. Therefore, it can be regarded that the picture element of interest associated with the degree of centralization C, which takes a large value, is the picture element located at the center portion of the tumor pattern. On the other hand, in a linear pattern, such as a blood vessel pattern, the directions of the gradient vectors are biased to a certain direction, and therefore the value of the degree of centralization C is small. Accordingly, a tumor pattern can be detected by taking each of all picture elements, which constitute the image, as the picture element of interest, calculating the value of the degree of centralization C with respect to the picture element of interest, and rating whether the value of the degree of centralization C is or is not larger than a predetermined threshold value. Specifically, the iris filter has the features over an ordinary difference filter in that the iris filter is not apt to be adversely affected by blood vessel patterns, mammary gland patterns, or the like, and can efficiently detect tumor patterns.

In actual processing, such that the detection performance unaffected by the sizes and shapes of tumor patterns may be achieved, it is contrived to adaptively change the size and the shape of the filter. FIG. 20 shows an example of the filter. The filter is different from the filter shown in FIG. 19. With the filter of FIG. 20, the degree of centralization is rated only with the picture elements, which are located along radial lines extending radially from a picture element of interest in M kinds of directions at $2\pi/M$ degree intervals. (In FIG. 20, by way of example, 32 directions at 11.25 degree intervals are shown.)

In cases where the picture element of interest has the coordinates (k, l), the coordinates ([x], [y]) of the picture element, which is located along an i'th radial line and is the n'th picture element as counted from the picture element of interest, are given by Formulas (10) and (11).

$$x = k + n \cos\{2\pi(i-1)/M\} \quad (10)$$

$$y = l + n \sin\{2\pi(i-1)/M\} \quad (11)$$

wherein [x] represents the maximum integer, which does not exceed x, and [y] represents the maximum integer, which does not exceed y.

Also, for each of the radial lines, the output value obtained for the picture elements ranging from the picture element of interest to a picture element, which is located along the radial line and at which the maximum degree of centralization is obtained, is taken as the degree of centralization with respect to the direction of the radial line. The mean value of the degrees of centralization, which have been obtained for all of the radial lines (in this case, 32 radial lines), is then calculated. The mean value of the degrees of centralization having thus been calculated is taken as the degree of centralization C of the gradient vector group with respect to the picture element of interest. Specifically, the degree of centralization Ci(n), which is obtained for the picture elements ranging from the picture element of interest to the n'th picture element located along the i'th radial line, is calculated with Formula (12).

$$Ci(n) = \sum_{l=1}^{n} \{(\cos \theta_{il})/n\}, \quad (12)$$

$$Rmin \leq n \leq Rmax$$

wherein Rmin and Rmax respectively represent the minimum value and the maximum value having been set for the radius of the tumor pattern, which is to be detected.

The calculation of the degree of centralization Ci(n) may be carried out by using Formula (12') in lieu of Formula (12).

$$Ci(n) = \frac{1}{n - Rmin + 1} \sum_{l=Rmin}^{n} \cos \theta_{il}, \quad (12')$$

$$Rmin \leq n \leq Rmax$$

Specifically, with Formula (12'), the degree of centralization Ci(n) is obtained for the picture elements, which are located along the i'th radial line and fall within the range from an Rmin'th picture element, that corresponds to the minimum value Rmin, as counted from the picture element of interest, to an n'th picture element, that falls within the range from the Rmin'th picture element to an Rmax'th picture element corresponding to the maximum value Rmax, as counted from the picture element of interest.

Thereafter, The degree of centralization C of the gradient vector group is calculated with Formulas (13) and (14)

$$Cimax = \max_{Rmin \leq n \leq Rmax} Ci(n) \quad (13)$$

$$C = (1/M) \sum_{i=1}^{M} Cimax \quad (14)$$

Formula (13) represents the maximum value of the degree of centralization Ci(n) obtained for each of the radial lines with Formula (12). Therefore, the region from the picture element of interest to the picture element associated with the degree of centralization Ci(n), which takes the maximum value, may be considered as being the region of the prospective tumor pattern. By the detection of such regions for all of the radial lines with Formula (13), it is possible to judge the shape of the peripheral edge of the region, which may be regarded as the prospective tumor pattern.

With Formula (13), the maximum values of the degrees of centralization within the aforesaid regions are calculated for all directions of the radial lines. Thereafter, with Formula (14), the mean value of the maximum values of the degrees of centralization within the aforesaid regions, which maximum values have been given by Formula (13) for all directions of the radial lines, is calculated. The calculated mean value is compared with a predetermined threshold value T. From the results of the comparison, a judgment is made as to whether there is or is not a probability that the region having its center at the picture element of interest will be the prospective abnormal pattern.

The region, in which the degree of centralization C of the gradient vector group with Formula (14) is rated, is similar to the iris of the human's eye, which expands or contracts in accordance with the brightness of the external field. The size and the shape of the region is changed adaptively in accordance with the distribution of the gradient vectors. Therefore, the filter used is referred to as the iris filter. (Step 3) Rating of the shape and form of the prospective tumor pattern In general, patterns of malignant tumors have the characteristics of the shapes and forms described below.

1) The side edges are irregular.
2) The shape is close to an ellipse.
3) The region inside of the pattern has a convex or concave density distribution.

Therefore, a judgment is made as to the shape and form by considering these characteristics such that patterns of normal tissues may be eliminated from the detected prospective pattern, and such that only the more definite "prospective abnormal pattern, i.e. only the prospective abnormal pattern having a very high probability of being a tumor pattern, can be detected. The characteristic measures used in making the judgment include the spreadness, the elongation, the roughness of side edges, the circularity, and the degree of convexity or concavity (i.e., the entropy) of the density distribution in the region inside of the pattern.

By carrying out the steps described above, the iris filter can efficiently detect a tumor pattern from a radiation image.

How the morphology processing is carried out will be described hereinbelow. The morphology processing is the technique for detecting a small calcified pattern, which is one of the characteristic forms of mammary cancers as in the cases of the tumor patterns. The morphology processing is carried out by using a multi-scale $\lambda$ and a structure element (i.e., a mask) B. The morphology processing has the features in that, for example, (1) it is efficient for extracting a calcified pattern itself, (2) it is not affected by complicated background information, and (3) the extracted calcified pattern does not become distorted. Specifically, the morphology processing is advantageous over ordinary differentiation processing in that it can more accurately detect the geometrical information concerning the size, the shape, and the density distribution of the calcified pattern. The morphology processing is carried out in the manner described below. (Fundamental operation of morphology processing) In general, the morphology operation is expanded as the theory of sets in an N-dimensional space. As an aid in facilitating the intuitive understanding, the morphology operation will be described hereinbelow with reference to a two-dimensional gray level image.

The gray level image is considered as a space, in which a point having coordinates (x, y) has a height corresponding to a density value f(x, y). In this case, it is assumed that the image signal representing the density value f(x, y) is a high luminance-high signal level type of image signal, in which a low density (i.e., a high luminance when the image is displayed on a CRT display device) is represented by a high image signal level.

Firstly, as an aid in facilitating the explanation, a one-dimensional function f(x) corresponding to the cross-section of the space is considered. It is assumed that structure element g used in the morphology operation is a symmetric function of Formula (15), which is symmetric with respect to the origin.

$$g^s(x)=g(-x) \quad (15)$$

It is also assumed that the value is 0 in a domain of definition G, which is represented by Formula (16).

$$G=\{-m,-m+1,\ldots,-1,0,1,\ldots,m-1,m\} \quad (16)$$

In such cases, the fundamental forms of the morphology operation are very simple operations carried out with Formulas (17), (18), (19), and (20).

$$\text{dilation; } [f \oplus G^s](i)=\max\{f(i-m),\ldots,f(i),\ldots,f(i+m)\} \quad (17)$$

$$\text{erosion ; } [f \ominus G^s](i)=\max\{f(i-m),\ldots,f(i),\ldots,f(i+m)\} \quad (18)$$

$$\text{opening } f_s=(f \ominus g^s) \oplus g \quad (19)$$

$$\text{closing } f^s=(f \oplus g^s) \ominus g \quad (20)$$

Specifically, as illustrated in FIG. 21A, the dilation processing is the processing for retrieving the maximum value in a width of $\pm m$ (the value determined in accordance with a structure element B) having its center at a picture element of interest. As illustrated in FIG. 21B, the erosion processing is the processing for retrieving the minimum value in the width of $\pm m$ having its center at the picture element of interest. The opening processing is equivalent to the searching of the maximum value after the searching of the minimum value. Also, the closing processing is equivalent to the searching of the minimum value after the searching of the maximum value. More specifically, as illustrated in FIG. 21C, the opening processing is equivalent to the processing for smoothing the density curve f(x) from the low luminance side, and removing a convex density fluctuating portion (i.e., the portion at which the luminance is higher than that of the surrounding portions), which fluctuates in a range spatially narrower than the mask size of 2m. Also, as illustrated in FIG. 21D, the opening processing is equivalent to the processing for smoothing the density curve f(x) from the high luminance side, and removing a concave density fluctuating portion (i.e., the portion at which the luminance is lower than that of the surrounding portions), which fluctuates in the range spatially narrower than the mask size of 2m.

In cases where the structure element g is not symmetric with respect to the origin, the dilation operation with Formula (17) is referred to as the Minkowski sum, and the erosion operation with Formula (18) is referred to as the Minkowski difference.

In cases where the image signal representing the density value f(x) is a high density-high signal level type of image signal, in which a high density is represented by a high image signal level, the relationship between the density value f(x) and the image signal value becomes reverse to the relationship between the density value f(x) and the image signal value in the high luminance-high image signal level type of image signal. Therefore, the dilation processing, which is carried out on the high density-high signal level type of image signal, coincides with the erosion processing, which is carried out on the high luminance-high signal level type of image signal as shown in FIG. 21B. The erosion processing, which is carried out on the high density-high signal level type of image signal, coincides with the dilation processing, which is carried out on the high luminance-high signal level type of image signal as shown in FIG. 21A. The opening processing, which is carried out on the high density-high signal level typo of image signal, coincides with the closing processing, which is carried out on the high luminance-high signal level type of image signal as shown in FIG. 21D. Also, the closing processing, which is carried out on the high density-high signal level type of image signal, coincides with the opening processing, which is carried out on the high luminance-high signal level type of image signal as shown in FIG. 21C.

The morphology processing is herein described with respect to the high luminance-high signal level type of image signal. (Application to detection of calcified patterns)

In order for a calcified pattern to be detected, it is considered to employ a difference method, in which a smoothed image signal is subtracted from the original image signal. However, with a simple smoothing method, it is difficult to discriminate the calcified pattern from an elongated non-calcified pattern (for example, a pattern of the mammary gland, a blood vessel, mammary gland supporting tissues, or the like). Therefore, Obata of Tokyo University of Agriculture and Technology, et al. have proposed a morphology filter, which is represented by Formula (21) and is based upon the opening operation using a multiply structure element. [Reference should be made to "Extraction of Small Calcified Patterns with A Morphology Filter Using A Multiply Structure Element," Collected Papers of The Institute of Electronics and Communication Engineers of Japan, D-II, Vol. J75-D-II, No. 7, pp. 1170–1176, Jul. 1992; and "Fundamentals of Morphology and Its Application to Mammogram Processing," Medical Imaging Technology, Vol. 12, No. 1, Jan. 1994.]

$$P = f - \max\{(f \ominus Bi) \oplus Bi\} \quad (21)$$
$$i \in (1, \ldots, M)$$
$$= f - \max\{f_{Bi}\}$$
$$i \in (1, \ldots, M)$$

In Formula (21), Bi (wherein i=1, 2, ..., M) represents, for example, four linear structure elements (in this case, M=4) shown in FIG. 22. (The four structure elements, as a whole, will hereinbelow be referred to as the multiply structure element.) In cases where the structure element B is set to be larger than the calcified pattern to be detected, a calcified pattern, which is a convex signal change portion finer than the structure element B (i.e., which is an image portion fluctuating in a spatially narrow range), is removed in the opening processing. On the other hand, an elongated non-calcified pattern is longer than the structure element B. Therefore, in cases where the inclination of the non-calcified pattern (i.e. the direction along which the non-calcified pattern extends) coincides with one of the directions of the four structure elements Bi, the non-calcified pattern remains unremoved after the opening processing, i.e. the operation of the second term of Formula (21), has been carried out. Therefore, when the smoothed image signal obtained from the opening processing (i.e. the signal representing the image, from which the calcified pattern has been removed) is subtracted from the original image signal f, an image can be obtained which contains only the small prospective calcified pattern. This is the concept behind Formula (21).

As described above, in cases where the image signal is of the high density-high signal level type, the density value of the calcified pattern is smaller than the density values of the surrounding image portions, and the calcified pattern constitutes a concave signal change portion with respect to the surrounding portions. Therefore, the closing processing is applied in lieu of the opening processing, and Formula (21') is applied in lieu of Formula (21).

$$P = f - \min\{(f \oplus Bi) \ominus Bi\} \quad (21')$$
$$i \in (1, \ldots, M)$$
$$= f - \min\{f_{Bi}\}$$
$$i \in (1, \ldots, M)$$

However, it often occurs that a non-calcafied pattern having the same size as the size of the calcified pattern remains in the obtained image. In such cases, the signal, which represents the non-calcified pattern and is contained in P of Formula (21), is removed by utilizing -the differentiation information based upon the morphology operation carried out- with Formula (22).

$$Mgrad = (\frac{1}{2}) \cdot (f \oplus \lambda B - f \ominus \lambda B) \quad (22)$$

A large value of Mgrad indicates a high possibiliaty of being a calcified pattern. Therefore, a prospective calcified pattern Cs can be detected with Formula (23).

if $P(i,j) \geq T1$ and $Mgrad(i,j) \geq T2$ then $C_s(i,j)=P$ else $C_s(i,j)=0$ (23)

In Formula (23), T1 and T2 represents the predetermined threshold values, which can be determined experimentally.

However, a non-calcified pattern, which has a size different from the size of the calcified pattern, can be removed by only the comparison of P of Formula (21) and the predetermined threshold value T1. Therefore, in cases where there is no risk that a non-calcified pattern having the same size as the size of the calcified pattern remains, it is sufficient for the condition of the first term of Formula (23), i.e. the condition of $P(i, j) > T1$, to be satisfied.

Finally, the cluster Cc of the calcified pattern is detected by the combination of the opening operation and the closing operation of the multi-scale in accordance with Formula (24).

$$C_c = C_s \oplus \lambda_1 B \ominus \lambda_3 B \oplus \lambda_2 B \quad (24)$$

In Formula (24), $\lambda_1$ and $\lambda_2$ are respectively determined by the maximum distance of the calcified pattern to be combined and the maximum radius of the isolated pattern to be removed, and $\lambda_3 = \lambda_1 + \lambda_2$.

As for the high luminance-high signal level type of image signal, the morphology filter is operated in the manner described above. In cases where the image signal is of the high density-high signal level type (in which a picture element of a high density has a large digital signal value), the relationship between the opening operation and the closing operation is reversed.

The present invention also provides a second apparatus for computer aided diagnosis of images, comprising:

i) an entire area image storing means for storing an entire area image signal representing a radiation image of an object, ii) an iris filter for calculating the degree of centralization of gradients of the entire area image signal, and thereby detecting an image portion, which is associated with a high degree of centralization, in the radiation image in accordance with the entire area image signal, iii) a judgment means for making a judgment as to the presence or absence of the image portion in accordance with the results of the detection of the image portion carried out by the iris filter, iv) a local area extracting means which, in cases where the judgment means has judged that the image portion is present, extracts a local area limited image signal corresponding to a local area containing the image portion from the entire area image signal having been stored in the entire area image storing means, v) a local area limited image displaying means for displaying the image of the local area in accordance with the local area limited image signal, which has been extracted by the local area extracting means, vi) an entire area image displaying means for displaying the entire area of the radiation image of the object in accordance with the entire area image signal, and vii) a local area limited image emphasizing means for selectively carrying out image emphasis processing on the abnormal pattern image signal, which represents the image portion and is among the local area limited image signal, in accordance with the results of the detection of the image portion carried out by the iris filter, such that the image portion in the image of the local area, which is displayed on the local area limited image displaying means, may have better image quality and higher capability of serving as an effective tool in, particularly, the efficient and accurate diagnosis of an illness than the radiation image, which is displayed on the entire area image displaying means.

As described above, the iris filter processing (hereinbelow often referred to as the operation of the iris filter) is already known as the operation processing for selectively extracting only a specific image portion, such as an abnormal pattern, from an image. Reference should be made to "Detection of Tumor Patterns in DR Images (Iris Filter)" described above. The iris filter processing has been studied as a technique efficient for detecting, particularly, a tumor pattern, which is one of characteristic forms of mammary cancers. However, the image to be processed with the iris filter is not limited to the tumor pattern in a mammogram, and the iris filter processing is applicable to any kind of image having the characteristics such that the gradients of the image signal representing the image are centralized.

As described above by taking the processing for the detection of the tumor pattern as an example, the processing for detecting the image portion with the iris filter is carried out with the processing of Step 1 to Step 3.

For example, in Step 3 described above, the circularity may be employed as the characteristic measure for the shape judgment. In such cases, when the degrees of centralization are binarized, the distribution of the binarized degrees of centralization corresponding to the tumor pattern ordinarily takes a shape close to a circle. The diameter of the circle having the same area as the area of the region obtained from the binary conversion is represented by Le. Also, the lengths of the longitudinal side and the lateral side of a square, which has the minimum area capable of accommodating the region, are respectively represented by a and b. In such cases, the circularity dairy is defined by Formula (26).

$$d_{circ} = Le/(a+b)$$

wherein $$Le = 2(S/\pi)^{1/2} \tag{26}$$

In cases where the value of the circularity is smaller than a predetermined threshold value, it is judged that the region is not a tumor pattern, and the region is not detected as the tumor pattern. In cases where the value of the circularity is not smaller than the predetermined threshold value, it is judged that the region is a tumor pattern, and the region is detected as the tumor pattern.

In the manner described above, with the iris filter, only the tumor pattern can be efficiently detected from the radiation image.

The term "image portion associated with a high degree of centralization" as used herein for the second apparatus for computer aided diagnosis of images in accordance with the present invention means specifically the image portion, which is obtained from the operation of the iris filter carrying out the processing of Step 1 to Step 3 described above.

In the second apparatus for computer aided diagnosis of images in accordance with the present invention, the local area limited image emphasizing means may comprise an abnormal pattern emphasizing means for carrying out an operation with Formula (1)

$$Dproc = Dorg + \alpha \cdot Giris \tag{1}$$

on the original image signal Dorg, which represents each of picture elements of the radiation image, by using an iris filter signal Giris, which has been obtained from the iris filter in accordance with the degree of centralization with respect to the original image signal Dorg, and an emphasis coefficient $\alpha$.

As the iris filter signal Giris, the signal representing the degree of centralization itself calculated with Formula (14) may be employed.

Also, in the second apparatus for computer aided diagnosis of images in accordance with the present invention, the local area limited image emphasizing means may comprise:

an unsharp mask signal calculating means for carrying out an operation on the original image signal Dorg, which represents each of picture elements of the radiation image, in order to calculate an unsharp mask signal Dus with respect to an unsharp mask constituted of a picture element matrix, which has a size of N columns×N rows and has its center at the picture element represented by the original image signal Dorg, the unsharp mask signal Dus being calculated with Formula (2)

$$Dus = (\sigma Dorg)/N^2 \tag{2}$$

wherein $\sigma Dorg$ represents the sum of the image signal values representing the picture elements located within the unsharp mask, a conversion table for converting an iris filter signal Giris, which has been obtained from the iris filter in accordance with the degree of centralization, into an emphasis coefficient $\beta(Giris)$ in accordance with the iris filter signal Giris, and an abnormal pattern emphasizing means for carrying out an operation with Formula (3)

$$Dproc = Dorg + \beta(Giris) \cdot (Dorg - Dus) \tag{3}$$

on the original image signal Dorg by using the unsharp mask signal Dus and the emphasis coefficient $\beta$ (Giris).

The emphasis coefficient $\beta(Giris)$ is an emphasis function having been set such that the output in accordance with the signal, which represents that a picture element is the one corresponding to the image portion described above, may be fed out as a value larger than the output in accordance with the signal, which represents that a picture element is not the one corresponding to the image portion described above. For example, the monotonously increasing function of the type shown in FIG. 25 should preferably be employed as the emphasis coefficient $\beta$ (Giris).

The present invention also provides a third apparatus for computer aided diagnosis of images, comprising:

i) an entire area image storing means for storing an entire area image signal representing a radiation image of an object, ii) a morphology filter for detecting an image portion, at which the image signal fluctuates in a spatially narrower range than a predetermined multiply structure element Bi, in the radiation image in accordance with the entire area image signal by using the multiply structure element Bi and a scale factor $\lambda$, iii) a judgment means for making a judgment as to the presence or absence of the image portion in accordance with the results of the detection of the image portion, at which the image signal fluctuates in a spatially narrower range than the multiply structure element Bi, the detection having been carried out by the morphology filter, iv) a local area extracting means which, in cases where the judgment means has judged that the image portion is present, extracts a local area limited image signal corresponding to a local area containing the image portion from the entire area image signal having been stored in the entire area image storing means, v) a local area limited image displaying means for displaying the image of the local area in accordance with the local area limited image signal, which has been extracted by the local area extracting means, vi) an entire area image displaying means for displaying the entire area of the radiation image of the object in accordance with the entire area image signal, and vii) a local area limited image emphasizing means for selectively carrying out image emphasis processing on the abnormal pattern image signal, which represents the image portion and is among the local area limited image signal, in accordance with the results of the detection of the image portion carried out by the morphology filter, such that the image portion in the image of the local area, which is displayed on the local area limited image displaying means, may have better image quality and higher capability of serving as an effective tool in, particularly, the efficient and accurate diagnosis of an illness than the radiation image, which is displayed on the entire area image displaying means.

As described above, the processing based upon the algorithm of morphology (hereinbelow referred to as the morphology operation or the morphology processing) has been studied as a technique efficient for detecting, particularly, a small calcified pattern, which is one of characteristic forms of mammary cancers. Reference should be made to "Extraction of Small Calcified Patterns with A Morphology Filter Using A Multiply Structure Element" described above. However, the image to be processed with the morphology processing is not limited to the small calcified pattern in a mammogram, and the morphology processing is applicable to any kind of image, in which the size and the shape of a specific image portion (i.e., an abnormal pattern, or the like) to be detected are known previously.

The morphology processing is carried out in the same manner as that described above by taking the processing for the detection of the small calcified pattern in a mammogram as an example.

Specifically, the term "image portion at which an image signal fluctuates in a spatially narrower range than a multiply structure element Bi" as used herein for the third apparatus for computer aided diagnosis of images in accordance with the present invention means the image portion detected with the morphology processing.

In the third apparatus for computer aided diagnosis of images in accordance with the present invention, the local area limited image emphasizing means may comprise:

a conversion table for converting a morphology signal Dmor into an output f(Dmor) in accordance with the morphology signal Dmor, the morphology signal Dmor having been obtained from the morphology filter with respect to the original image signal Dorg, which represents each of picture elements of the radiation image, the morphology signal Dmor representing the image portion, at which the image signal fluctuates in a spatially narrower range than the multiply structure element Bi, and an abnormal pattern emphasizing means for carrying out an operation with Formula (4)

$$Dproc = Dorg + \alpha \cdot f(Dmor) \quad (4)$$

on the original image signal Dorg by using the output f(Dmor) and an emphasis coefficient $\alpha$.

As illustrated in FIG. 29, the function f(Dmor) should preferably be set to convert such that the output f(Dmor) may be fixed at 0 (zero) with respect to a region C1, in which the value of the morphology signal |Dmor| is very small, such that the output f(Dmor) may be monotonously increased with respect to |Dmor| for a region C2, in which the value of the morphology signal |Dmor| is comparatively large, and such that the output f(Dmor) may be fixed at the upper limit value with respect to a region C3, in which the value of the morphology signal |Dmor| is very large. In such cases, in the region C1, in which the value of Dmor is small, high-frequency radiation noise detected by the morphology filter can be reduced. Also, in the region C3 having a certain extent of contrast, excessive emphasis processing can be prevented from being carried out.

As the function f(Dmor), the morphology signal Dmor itself may be employed.

Also, in the third apparatus for computer aided diagnosis of images in accordance with the present invention, the local area limited image emphasizing means may comprise:

a conversion table for converting the original image signal Dorg, which represents each of picture elements of the radiation image, into an emphasis coefficient b(Dorg) in accordance with the original image signal Dorg, and an abnormal pattern emphasizing means for carrying out an operation with Formula (5)

$$Dproc = Dorg + \beta(Dorg) \cdot (Dorg - Dmor) \quad (5)$$

on the original image signal Dorg by using a morphology signal Dmor and the emphasis coefficient $\beta$ (Dorg), the morphology signal Dmor having been obtained from the morphology filter and representing the image portion, at which the image signal fluctuates in a spatially narrower range than the multiply structure element Bi.

In this constitution, (i) in cases where the emphasis processing is to be carried out for an image portion (for example, a calcified pattern represented by the high luminance-high signal level type of image signal), in which the value of the original image signal Dorg is larger than the image signal values representing the surrounding image areas and at which the image signal fluctuates in a spatially narrower range than the multiply structure element Bi, as illustrated in FIG. 30A, the emphasis coefficient $\beta$(Dorg) should preferably be set as being a function monotonously increasing with respect to Dorg. Also, (ii) in cases where the emphasis processing is to be carried out for an image portion (for example, a calcified pattern represented by the high density-high signal level type of image signal), in which the value of the original image signal Dorg is smaller than the image signal values representing the surrounding image areas and at which the image signal fluctuates in a spatially narrower range than the multiply structure element Bi, as illustrated in FIG. 30B, the emphasis coefficient $\beta$(Dorg) should preferably be set as being a function monotonously decreasing with respect to Dorg.

Further, in the third apparatus for computer aided diagnosis of images in accordance with the present invention, the local area limited image emphasizing means may comprise:

a conversion table for converting a morphology signal Dmor into an emphasis coefficient $\beta$(Dmor) in accordance with the morphology signal Dmor, the morphology signal Dmor having been obtained from the morphology filter with respect to the original image signal Dorg, which represents each of picture elements of the radiation image, the morphology signal Dmor representing the image portion, at which the image signal fluctuates in a spatially narrower range than the multiply structure element Bi, and an abnormal pattern emphasizing means for carrying out an operation with Formula (6)

$$Dproc=Dorg+\beta(Dmor)\cdot(Dorg-Dmor) \quad (6)$$

on the original image signal Dorg by using the emphasis coefficient β(Dmor) and a signal, which represents the difference between the original image signal Dorg and the morphology signal Dmor.

As illustrated in FIG. 31, in cases where the emphasis processing is carried out with Formula (6) in accordance with the morphology signal Dmor, the emphasis coefficient β(Dmor) should preferably be set as being a function monotonously increasing with respect to Dmor.

The aforesaid morphology operation may be carried out with Formula (27) shown below. In such cases, an image portion, in which the value of the original image signal Dorg is larger than the image signal values representing the surrounding image areas, can be extracted, and the extracted image portion can be selectively subjected to the emphasis processing.

$$Dmor=Dorg-\max\ \{(Dorg\ominus\lambda Bi)\oplus\lambda Bi\}i=1,\ldots,n \quad (27)$$

The expression X–λY represents that λ times of calculations for finding the Minkowski difference are carried out with the structure element Y on the image signal X, and X+λY represents that λ times of calculations for finding the Minkowski sum are carried out with the structure element Y on the image signal X.

As the structure element B, by way of example, a bisymmetric element having a form of a square, a rectangle, a circle, an ellipse, a rhombus, or the like, is preferable.

Alternatively, the aforesaid morphology operation may be carried out with Formula (28) shown below. In such cases, an image portion, in which the value of the original image signal Dorg is smaller than the image signal values representing the surrounding image areas, can be extracted, and the extracted image portion can be selectively subjected to the emphasis processing.

$$Dmor=Dorg-\min\ \{(Dorg\oplus\lambda Bi)\ominus\lambda Bi\}i=1,\ldots,n \quad (28)$$

Furthermore, in the third apparatus for computer aided diagnosis of images in accordance with the present invention, the local area limited image emphasizing means may comprise:

an unsharp mask signal calculating means for carrying out an operation on the original image signal Dorg, which represents each of picture elements of the radiation image, in order to calculate an unsharp mask signal Dus with respect to an unsharp mask constituted of a picture element matrix, which has a size of N columns ×N rows and has its center at the picture element represented by the original image signal Dorg, the unsharp mask signal Dus being calculated with Formula (2)

$$Dus=(\Sigma Dorg)/N^2 \quad (2)$$

a conversion table for converting a morphology signal Dmor into an emphasis coefficient β (Dmor) in accordance with the morphology signal Dmor, the morphology signal Dmor having been obtained from the morphology filter and representing the image portion, at which the image signal fluctuates in a spatially narrower range than the multiply structure element Bi, and an abnormal pattern emphasizing means for carrying out an operation with Formula (7)

$$Dproc=Dorg+\oplus(Dmor)\cdot(Dorg-Dus) \quad (7)$$

on the original image signal Dorg by using the unsharp mask signal Dus and the emphasis coefficient b(Dmor).

As illustrated in FIG. 28A or FIG. 28B, the function β (Dmor) is a function, wherein the output is restricted to a small value with respect to the region, in which the value of |Dmor| is small.

As the structure element B, by way of example, a bisymmetric element having a form of a square, a rectangle, a circle, an ellipse, a rhombus, or the like, is preferable.

Also, as the morphology operation, one of various operations carried out with Formulas (27) to (33) shown below may be employed.

$$Dmor=Dorg-\max\ \{(Dorg\ominus\lambda Bi)\oplus\lambda Bi\}i=1,\ldots,n \quad (27)$$

$$Dmor=Dorg-\min\ (Dorg\oplus\lambda Bi)\ominus\lambda Bi\}i=1,\ldots,n \quad (28)$$

$$Dmor=Dorg-\max\ (Dorg\ominus\lambda Bi)\ i=1,\ldots,m \quad (29)$$

$$Dmor=Dorg-\min\ (Dorg\oplus\lambda Bi)\ i=1,\ldots,n \quad (30)$$

$$Dmor = \bigcup_{\lambda=0}^{N} \{\max(Dorg \ominus \lambda Bi) - \quad (31)$$

$$i=1,\ldots,n$$

$$\max\ (Dorg \ominus \lambda Bi)_g\}$$

$$i=1,\ldots,n$$

The expression $(X-\lambda Y)_Y$ represents that the opening operation with the structure element Y is carried out on the image signal $(X-\lambda Y)$, and $$\bigcup_{\lambda=0}^{N}$$

represents the sum of sets of λ=0, 1, . . . , N.

$$Dmor = \bigcup_{\lambda=0}^{N} \{\min(Dorg \oplus \lambda Bi) - \quad (32)$$

$$i=1,\ldots,n$$

$$\min\ (Dorg \oplus \lambda Bi)^g\}$$

$$i=1,\ldots,n$$

The expression $(X+\lambda Y)^Y$ represents that the closing operation with the structure element Y is carried out on the image signal $(X+\lambda Y)$ $$Dmor = \operatorname{lmin}(Dorg \oplus \lambda Bi) - \quad (33)$$

$$i=1,\ldots,n$$

$$\max(Dorg \ominus \lambda Bi)|$$

$$i=1,\ldots,n$$

Specifically, by the application of the morphology operation carried out with Formula (27), it is possible to extract, as the morphology signal Dmor, a signal representing the picture elements constituting an image portion, in which the value of the original image signal Dorg is larger than the image signal values representing the surrounding image areas, and at which the image signal fluctuates in a spatially narrower range than the multiply structure element Bi (for example, the calcified pattern in cases where the image signal is of the nigh luminance-high signal level type). Also, the extracted image portion can be efficiently processed with the emphasis processing.

Also, by the application of the morphology operation carried out with Formula (28), it is possible to extract, as the morphology signal Dmor, a signal representing the picture elements constituting an image portion, in which the value of the original image signal Dorg is smaller than the image signal values representing the surrounding image areas, and at which the image signal fluctuates in a spatially narrower range than the multiply structure element Bi (for example, the calcified pattern in cases where the image signal is of the high density-high signal level type). Also, the extracted image portion can be efficiently processed with the emphasis processing.

Further, by the application of the morphology operation carried out with Formula (29), it is possible to extract, as the morphology signal Dmor, a signal representing the picture elements constituting an image portion, in which the value of the original image signal Dorg is larger than the image signal values representing the surrounding image areas, and at which the image signal fluctuates in a spatially narrower range than the multiply structure element Bi, and an image edge portion at which the luminance (or the density) changes sharply. Also, the extracted image portion can be efficiently processed with the emphasis processing.

By the application of the morphology operation carried out with Formula (30), it is possible to extract, as the morphology signal Dmor, a signal representing the picture elements constituting an image portion, in which the value of the original image signal Dorg is smaller than the image signal values representing the surrounding image areas, and at which the image signal fluctuates in a spatially narrower range than the multiply structure element Bi, and an image edge portion at which the luminance (or the density) changes sharply. Also, the extracted image portion can be efficiently processed with the emphasis processing.

By the application of the morphology operation carried out with Formula (31), it is possible to extract, as the morphology signal Dmor, a signal representing the picture elements constituting an image portion, in which the value of the original image signal Dorg is larger than the image signal values representing the surrounding image areas, and at which the image signal fluctuates in a spatially narrower range than the multiply structure element Bi and a change in the density (or a change in the luminance) is large (for example, a skeleton pattern in the image represented by the original image signal Dorg). Also, the extracted image portion (for example, the skeleton pattern) can be efficiently processed with the emphasis processing. FIG. 32 shows an example of the skeleton processing carried out with Formula (31). As illustrated in FIG. 32, a calculation is made to find a difference signal between a signal representing an image, which has been obtained by carrying out the erosion processing on an original image X with a structure element B (in this case, a circular structure having a radius of r), and a signal representing an image, which has been obtained by carrying out the opening processing on the image obtained from the erosion processing. The sum of sets of the difference signals obtained from the λ number of operations (wherein λ=1, 2, . . . , N) represents a skeleton patterns a and b.

By the application of the morphology operation carried out with Formula (32), it is possible to extract, as the morphology signal Dmor, a signal representing the picture elements constituting an image portion, in which the value of the original image signal Dorg is smaller than the image signal values representing the surrounding image areas, and at which the image signal fluctuates in a spatially narrower range than the multiply structure element Bi and a change in the density (or a change in the luminance) is large (for example, a skeleton pattern in the image represented by the original image signal Dorg). Also, the extracted image portion (for example, the skeleton pattern) can be efficiently processed with the emphasis processing.

The morphology operation carried out with Formula (31) or (32) is ordinarily referred to as the skeleton processing. With the skeleton processing, particularly in cases where it is applied to an image signal representing a bone trabecula pattern in a radiation image), only the skeleton element can be selectively and efficiently emphasized.

By the application of the morphology operation carried out with Formula (33), it is possible to extract, as the morphology signal Dmor, a signal representing the picture elements constituting an image portion, in which a local change in the luminance (or a change in the density) is large. Also, the extracted image portion can be efficiently processed with the emphasis processing.

In cases where the morphology operation is carried out with Formula (33), in order for the undershooting and overshooting to be restricted, (Dorg-Dus) in the second term in Formula (7) should be altered to, for example, a function f(Dorg-Dus) as shown in FIG. 33, which restricts the output, with respect to the range of the Dorg values not larger than a predetermined value or with respect to the range of the Dorg values not smaller than a predetermined value.

The second and third apparatuses for computer aided diagnosis of images in accordance with the present invention may be modified such that the entire area image displaying means may also serve as the local area limited image displaying means, and the local area limited image may be displayed at a portion of the display surface of the entire area image displaying means. Specifically, while the entire area image is being displayed on the entire area image displaying means, the local area limited image, which will otherwise be displayed on an independent local area limited image displaying means, may be displayed at a portion of the entire area image, which is being displayed on the entire area image displaying means. (This means that, at the portion of the display surface of the entire area image displaying means, at which portion the local area limit-ed image is displayed, the portion of the entire area image and the local area limited image are not superposed one upon the other, but instead only the local area limited image is displayed without the portion of the entire area image being displayed. At the other portion of the display surface of the entire area image displaying means, the remaining portion of the entire area image is displayed.)

The entire area image and the local area limited image may be displayed in various manners in accordance with the kind of the object, the image of which is displayed. Specifically, for example, in cases where the X-ray image of the mamma, or the like, of a single patient is displayed, only the image of the single mamma may be displayed. Alternatively, for example, two entire area image displaying means and/or two local area limited image displaying means may be provided. In this manner, the local area limited image containing the abnormal pattern in one of the two mammae of the patient may be displayed on one of the two image displaying means. At the same time, the local area limited image of the portion of the other mamma, which portion corresponds to the local area of the one mamma, may be displayed on the other image displaying means. In such cases, the person, who views the radiation image, can compare the corresponding portions of the right and left mammae of the single patient.

More specifically, a pair of -he entire area images of the right and left mammae of a single patient may be displayed on a single entire area image displaying means. Alternatively, the entire area image of one of the mammae may be displayed on one of two entire area image displaying means, and the entire area image of the other mammae may be displayed on the other entire area image displaying means.

Also, in cases where a prospective abnormal pattern is detected in one of the mammae, the local area limited image containing the prospective abnormal pattern in the one mamma and the image of the local area in the other mamma, which local area corresponds to the portion of the local area in the one mamma, may be displayed in pair on a single local area limited image displaying means, or may be respectively displayed on two local area limited image displaying means. In such cases, the same local area limited image emphasis processing should preferably be carried out on the images of the local areas in the pair of the mammae of the single patient.

Further, in cases where the entire area image displaying means also serves as the local area limited image displaying means, a pair of the entire area images of the right and left mammae of the single patient may be displayed on one or two entire area image displaying means, and the images of the corresponding local areas of the right and left mammae may be displayed respectively in the entire area images.

Furthermore, the image of one of the mammae of the single patient and the image of the other mamma, which has been recorded independently of the image of the one mamma, may be simultaneously displayed on the display surface of the same image displaying means. Specifically, the image of the one mamma may be displayed at the right half of the display surface of the entire area image displaying means, and the image of the other mamma may be displayed simultaneously at the left half of the display surface of the same entire area image displaying means, such that the two images may stand facing each other. In cases where the prospective abnormal pattern is detected from the entire area image signal, which represents the image of the one mamma, the local area limited image containing the prospective abnormal pattern may be subjected to the emphasis processing and then displayed at a portion of the right half of the display surface, i.e., at a portion of the entire area image of the one mamma. Also, the local area limited image of the portion of the other mamma, which portion corresponds to the position of the prospective abnormal pattern in the one mamma, may be displayed at a portion of the left half of the display surface, i.e., at a portion of the entire area image of the other mamma.

As described above, the two images represented by two image signals obtained independently of each other may be displayed on two independent image displaying means or at different display positions on a single image displaying means, such that the same portions of the two images may correspond to each other. In such cases, the second and third apparatuses for computer aided diagnosis of images in accordance with the present invention may further comprise two means for respectively storing the entire area image signal representing one mamma and the entire area image signal representing the other mamma, means for detecting two image signals (the two entire area image signals or the two local area limited image signals) in association with the relationship between the image positions, and a display control means for controlling the storing means and the detection means and causing the images to be displayed on the image display means.

With the first apparatus for computer aided diagnosis of images in accordance with the present invention, the entire area image displaying means displays the entire area of the radiation image of the object in accordance with the entire area image signal, which has been received directly or via the entire area image storing means from the exterior. Also, the entire area image signal is Fed into the prospective abnormal pattern detecting means directly or via the entire area image storing means. In accordance with the entire area image signal, the prospective abnormal pattern detecting means detects a prospective abnormal pattern, which is considered as being an abnormal pattern, such as a tumor pattern. In cases where the prospective abnormal pattern has been detected, the prospective abnormal pattern detecting means specifies the picture elements corresponding to the image signal, which represents the prospective abnormal pattern. Also, the prospective abnormal pattern detecting means feeds a position signal, which represents the positions of the specified picture elements, into the judgment means. In cases where a prospective abnormal pattern has not been detected, no position signal is fed out.

In cases where the position signal is received, the judgment means judges that the prospective abnormal pattern has been detected. Also, the judgment means feeds the received position signal into the local area extracting means. In cases where it has been judged that no prospective abnormal pattern has been detected, no position signal is received from the prospective abnormal pattern detecting means, and therefore the processing is finished.

The local area extracting means also receives the entire area image signal from the entire area image storing means. In accordance with the received entire area image signal and the received position signal, the local area extracting means specifies the picture elements (i.e., the local area constituted of the set of these picture elements), which include the picture elements corresponding to the image signal representing the prospective abnormal pattern and are located in the vicinity of them, according to a predetermined processing procedure. The local area extracting means thus extracts the local area limited image signal, which represents the image of the local area, from the entire area image signal.

The extracted local area limited image signal is fed into the local area limited image displaying means. In accordance with the received local area limited image signal, the local area limited image displaying means displays the local area limited image containing the prospective abnormal pattern.

In this manner, on the local area limited image displaying means, only the local area limited image containing the prospective abnormal pattern is displayed independently of the entire area image. Therefore, the person, who views the radiation image, can concentrate his attention on the local area limited image, which is displayed on the local area limited image displaying means. As a result, the efficiency and the accuracy of the diagnosis, or the like, can be kept high, and the time required for making the diagnosis, or the like, can be kept short.

Also, as described above, the first apparatus for computer aided diagnosis of images in accordance with the present invention may further comprise the local area limited image storing means, which is located between the local area extracting means and the local area limited image displaying means and which temporarily stores the local area limited image signal, and the local area limited image display requesting means, which is located between the local area extracting means and the local area limited image displaying means and which, only when a predetermined image display request is received from the exterior, causes the local area limited image signal to be fed out from the local area limited image storing means and causes the image of the local area to be displayed on the local area limited image displaying means. With this constitution, the local area limited image signal, which has been extracted by the local area extracting means, is fed into and temporarily stored in the local area limited image storing means, and the processing is temporarily ceased.

When the person, who views the radiation image, feeds a signal, which represents a request for displaying the local area limited image, into the local area limited image display requesting means, the signal representing the request for displaying the local area limited image is fed from the local area limited image display requesting means into the local area limited image storing means. In accordance with this signal, the local area limited image storing means feeds the stored local area limited image signal into the local area limited image displaying means, and the processing is thus resumed.

With the apparatus for computer aided diagnosis of images having the constitution described above, the local area limited image signal, which represents the local area limited image containing the detected prospective abnormal pattern, is temporarily stored in the local area limited image storing means. Therefore, the person, who views the radiation image, can arbitrarily determine whether to display the local area limited image on the local area limited image displaying means or not in accordance with circumstances, such as the time available for the image viewing.

Specifically, ordinarily, the person, who views the radiation image, firstly views the entire area image in order to recognize the entire image information to some extent, and thereafter views a detail structure. Therefore, with the constitution described above, the person, who views the radiation image, can firstly view the entire area image displayed on the entire area image displaying means. At a desired point of time after or during the viewing of the entire area image, the person, who views the radiation image, can immediately display the local area limited image, which contains the prospective abnormal pattern, on the local area limited image displaying means by carrying out a simple operation for making a display request to the local area limited image display requesting means. Thus the apparatus for computer aided diagnosis of images can be operated in accordance with the actual circumstances at the sites of medical treatment, or the like.

Also, the first apparatus for computer aided diagnosis of images in accordance with the present invention may further comprise the local area limited image emphasizing means for carrying out image emphasis processing on at least the abnormal pattern image signal, which is among the local area limited image signal, such that at least the image of the prospective abnormal pattern in the image of the local area, which is displayed on the local area limited image displaying means, may have better image quality and higher capability of serving as an effective tool in, particularly, the efficient and accurate diagnosis of an illness than the entire area image, which is displayed on the entire area image displaying means. With this constitution, the local area limited image signal, which has been extracted by the local area extracting means, is fed into the local area limited image emphasizing means and is thereby subjected to the image emphasis processing, such as the gradation processing, the frequency processing, and the enlargement processing.

The image emphasis processing is carried out in order to enhance the image quality of the local area limited image, which is related to the diagnosis, or the like, and its capability of serving as an effective tool in, particularly, the efficient and accurate diagnosis of an illness. For example, in cases where the gradation processing is employed as the image emphasis processing, the gradation processing may be carried out such that the level of contrast of the local area limited image (or the image of the prospective abnormal pattern), which is displayed on the local area limited image displaying means may become higher than the level of contrast of the entire area image, which is displayed on the entire area image displaying means. The gradation processing should preferably be set such that the level of contrast of the local area limited image (or the image of the prospective abnormal pattern) may become at least 1.2 times as high as the level of contrast of the entire area image. In cases where the frequency processing is employed as the image emphasis processing, the frequency processing may be set such that the degree of emphasis of the local area limited image (or the image of the prospective abnormal pattern), which is displayed on the local area limited image displaying means, may be higher than the degree of emphasis of the entire area image, which is displayed on the entire area image displaying means. The frequency processing should preferably be set such that the degree of emphasis of the local area limited image (or the image of the prospective abnormal pattern) may become at least 1.1 times as high as the degree of emphasis of the entire area image. Also, in cases where the enlargement processing is employed as the image emphasis processing, such that detail structures can be viewed accurately, the enlargement processing should preferably be set so that the display size of the local area limited image (or the image of the prospective abnormal pattern), which is displayed on the local area limited image displaying means, may become at least 1.5 times as large as the display size of the local area limited image (or the image of the prospective abnormal pattern) in the entire area image, which is displayed on the entire area image displaying means.

Further, as described above, the enlargement processing may be set such that the scale of enlargement may be changed in accordance with the size of the prospective abnormal pattern detected by the prospective abnormal pattern detecting means. In this manner, the scale of enlargement may be changed such that the size of the prospective abnormal pattern displayed may become approximately equal to a predetermined size regardless of the size of the prospective abnormal pattern detected. In such cases, even if the size of the prospective abnormal pattern detected Is small, the prospective abnormal pattern can be viewed as an image having a size approximately equal to a predetermined size. Therefore, the efficiency and the accuracy of the diagnosis, or the like, can be kept high.

With the first apparatus for computer aided diagnosis of images in accordance with the present invention, which further comprises the entire area image emphasizing means, the image emphasis processing, such as the gradation processing or the frequency processing, is carried out on the image signal, which represents the entire area image displayed on the entire area image displaying means, by the entire area image emphasizing means, such that the image quality of the entire area image and its capability of serving as an effective tool in, particularly, the efficient and accurate diagnosis of an illness can be kept high. In cases where the image emphasis processing is carried out on the entire area image by the entire area image emphasizing means, the image emphasis processing of the local area limited image, which is displayed on the local area limited image displaying means, is carried out to a higher extent (i.e., to a higher level of contrast with the gradation processing, with a higher degree of emphasis with the frequency processing, or with a larger scale of enlargement with the enlargement processing for obtaining detail structures capable of being viewed more accurately) than the image emphasis processing of the entire area image, which is displayed on the entire area image displaying means, such that, as for the local area limited image (or the image of the prospective abnormal pattern), the image displayed on the local area limited image displaying means may have better image quality and higher capability of serving as an effective tool in, particularly, the efficient and accurate diagnosis of an illness than the image displayed on the entire area image displaying means. Particularly, the gradation processing should preferably be set such that the level of contrast of the image, which is displayed on the local area limited image displaying means, may become at least 1.2 times as high as the level of contrast of the image, which is displayed on the entire area image displaying means. The frequency processing should preferably be set such that the degree of emphasis of the image, which is displayed on the local area limited image displaying means, may become at least 1.1 times as high as the degree of emphasis of the image, which is displayed on the entire area image displaying means. Also, the enlargement processing should preferably be set so that the display size of the local area limited image (or the image of the prospective abnormal pattern), which is displayed on the local area limited image displaying means, may become at least 1.5 times as large as the display size of the local area limited image (or the image of the prospective abnormal pattern) in the entire area image, which is displayed on the entire area image displaying means.

The first apparatus for computer aided diagnosis of images in accordance with the present invention may be constituted such that the entire area image displaying means may also serve as the local area limited image displaying means. With this constitution, while the entire area image is being displayed on the display surface of the entire area image displaying means, the local area limited image containing the prospective abnormal pattern can be displayed at a portion of the entire area image when a display request is made from the local area limited image display requesting means.

In cases where the entire area image and the local area limited image containing the prospective abnormal pattern are displayed on a single display surface of the display means, the position of the prospective abnormal pattern in the entire area image can be found more easily. Therefore, the efficiency and the accuracy of the diagnosis, or the like, can be kept high.

The local area limited image, which is displayed on the entire area image displaying means, may be displayed in a display region, which is different from the local area in the radiation image displayed on the entire area image displaying means. In such cases, the local area limited image does not overlap upon the local area in the displayed entire area image. Therefore, the local area limited image can be viewed while the position of the local area in the entire area image is being recognized. As a result, the efficiency and the accuracy of the diagnosis, or the like, can be kept high.

Also, the display region for the local area limited image, which is displayed on the entire area image displaying means, may be determined such that it may be accommodated in a display region, which is different from the object image displayed on the entire area image displaying means. In this manner, the local area limited image can be prevented from overlapping upon the local region in the entire area image and upon the object image in the entire area image. Also, the local area limited image may be scrolled within the window region on the display surface of the entire area image displaying means. In such cases, even if the size of the display region for the local area limited image in the entire area image displaying means is smaller than the size of the local area limited image, only a portion of the local area limited image can be displayed in the window, and the local area limited image can be scrolled within the window. In this manner, the necessary portion of the local area limited image can be viewed successively.

In cases where a plurality of window regions are provided, when a plurality of prospective abnormal patterns are detected, all of them can be viewed simultaneously with the entire area image. Such a constitution is more efficient for diagnosis, or the like.

With the second apparatus for computer aided diagnosis of images in accordance with the present invention, the entire area image displaying means displays the entire area of the radiation image of the object in accordance with the entire area image signal, which has been received directly or via the entire area image storing means from the exterior. Also, the entire area image signal is fed into the iris filter directly or via the entire area image storing means. In accordance with the entire area image signal, the iris filter carries out the processing of Step 1 to Step 3 described above and detects an image portion, such as a tumor pattern, which is associated with a high degree of centralization of the gradients of the image signal. In cases where the image portion, which is associated with a high degree of centralization of the gradients of the image signal, has been detected, the iris filter specifies the picture element corresponding to the image portion. Also, the iris filter feeds a position signal, which represents the position of the specified picture element, and an iris filter signal Giris with respect to the picture element into the judgment means. In cases where an image portion, which is associated with a high degree of centralization of the gradients of the image signal, has not been detected, the position signal and the iris filter signal Giris are not fed out.

In cases where the position signal is received, the judgment means judges that the image portion (hereinbelow referred to as the "image portion, such as the abnormal pattern" in the explanation of the second apparatus for computer aided diagnosis of images in accordance with the present invention), which is associated with a high degree of centralization of the gradients of the image signal, has been detected. Also, the judgment means feeds the received position signal into the local area extracting means. In cases where it has been judged that the image portion, such as the abnormal pattern, has not been detected, no position signal is received from the iris filter, and therefore the processing is finished.

The local area extracting means also receives the entire area image signal from the entire area image storing means. In accordance with the received entire area image signal and the received position signal, the local area extracting means specifies the picture elements (i.e., the local area constituted of the set of these picture elements), which include the picture element corresponding to the image portion, such as the abnormal pattern, and are located in the vicinity of it, according to a predetermined processing procedure. The local area extracting means thus extracts the local area limited image signal, which represents the image of the local area, from the entire area image signal.

The extracted local area limited image signal is fed into the local area limited image emphasizing means. The local area limited image emphasizing means also receives the iris filter signal, which has been generated in accordance with the degree of centralization of the gradients of the image signal. The local area limited image emphasizing means carries out emphasis processing on the local area limited image signal (i.e., the original image signal) Dorg in accordance with the iris filter signal Giris. As described above, the iris filter signal Giris takes a large value with respect to the picture element corresponding to the image portion, such as the abnormal pattern, and a small value with respect to picture elements other than the picture element corresponding to the image portion, such as the abnormal pattern. Therefore, by the weighting of the iris filter signal Girls and the addition of the weighted iris filter signal Giris to the original image signal Dorg, only the image portion, such as the abnormal pattern, can be selectively and efficiently emphasized.

An image signal Dproc is obtained from the emphasis processing carried out by the local area limited image emphaszing means. The image signal Dproc is fed into the local area limited image displaying means. In accordance with the received image signal Dproc, the local area limited image displaying means displays the local area limited image containing the abnormal pattern.

In this manner, only the image, in which the image portion, such as the abnormal pattern, has been emphasized to a high extent, is displayed on the local area limited image displaying means. Therefore, the efficiency and the accuracy of the diagnosis, or the like, which is made by viewing the image, can be kept high.

Also, the local area limited image containing the image portion, such as the abnormal pattern, is displayed independently of the entire area image. Therefore, the person, who views the radiation image, can concentrate his attention on the local area limited image, which is displayed on the local area limited image displaying means. As a result, the efficiency and accuracy of the diagnosis, or the like, can be kept high. In cases where the entire area image displaying means also serves as the local area limited image displaying means, the image area emphasized to a high extent is only the image portion, such as the abnormal pattern, and therefore the effects of enhancing the efficiency and the accuracy of the diagnosis, or the like, can be obtained.

As described above, the image portion to be subjected to the emphasis processing is not limited to the tumor pattern, in which the density value is smaller than the density values of the surrounding areas. For example, a pattern, in which the density value is larger than the density values of the surrounding areas and the density gradients are centralized, can also be selectively subjected to the emphasis processing. Therefore, the second apparatus for computer aided diagnosis of images in accordance with the present invention is applicable to the high density-high signal level type of image signal and the high luminance-high signal level type of image signal. This also applies to the modifications of the second apparatus for computer aided diagnosis of images in accordance with the present invention.

In cases where the local area limited image emphasizing means is provided with the abnormal pattern emphasizing means for carrying out the emphasis processing with Formula (1), the same effects as those described above can be obtained.

Further, with the second apparatus for computer aided diagnosis of images in accordance with the present invention, wherein the local area limited image emphasizing means is provided with the unsharp mask signal calculating means, the conversion table, and the abnormal pattern emphasizing means, the unsharp mask signal calculating means carries out the operation with Formula (2) in order to calculate the unsharp mask signal Dus with respect to each picture element. The conversion table is used for converting the iris filter signal Giris into the emphasis coefficient $\beta$ (Girls) in accordance with the iris filter signal Giris Also, the abnormal pattern emphasizing means carries out the emphasis processing with Formula (3) on the original image signal Dorg by using the unsharp mask signal Dus, the emphasis coefficient $\beta$ (Giris), and the original image signal Dorg.

With the calculation of the second term of Formula (3), the super-low frequency component Dus is subtracted from the original image signal Dorg, and a comparatively high frequency component (i.e., the component other than the super-low frequency component) can be extracted from the original image signal Dorg. The comparatively high frequency component having thus been extracted contains radiation noise, which is a high frequency component. However, the frequency emphasis coefficient $\beta$ (Giris) , by which the comparatively high frequency component is multiplied, is based upon the iris filter signal Giris having the value in accordance with whether the picture element corresponds to or does not correspond to the image portion, such as the abnormal pattern. Therefore, even if an unnecessary component, such as quantum noise, is contained in the high frequency component (Dorg-Dus), in cases where the picture element is not the one constituting the image portion, such as the abnormal pattern, the value of $\beta$ (Giris) with respect to the picture element will be small, and the degree of emphasis with respect to the picture element will be kept low.

In cases where the picture element is the one constituting the image portion, such as the abnormal pattern, the value of $\beta$ (Giris) with respect to the picture element is large, and therefore the degree of emphasis with respect to the picture element is kept high.

Therefore, regardless of whether radiation noise is or is not contained in the high frequency component (Dorg-Dus) of the image, the image portion, such as the abnormal pattern, can be selectively emphasized with the function $\beta$ (Giris), which has a value in accordance with whether the image area is or is not the image portion, such as the abnormal pattern.

With the third apparatus for computer aided diagnosis of images in accordance with the present invention, the entire area image displaying means displays the entire area of the radiation image of the object in accordance with the entire area image signal, which has been received directly or via the entire area image storing means from the exterior. Also, the entire area image signal is fed into the morphology filter directly or via the entire area image storing means. In accordance with the entire area image signal, the morphology filter carries out the morphology operation by using the multiply structure element Bi and the scale factor $\lambda$ and thereby detects the image portion, such as the small calcified pattern, at which the image signal fluctuates in a spatially narrower range than the multiply structure element Bi. In cases where the image portion, at which the image signal fluctuates in a spatially narrower range than the multiply structure element Bi, has been detected, the morphology filter specifies the picture element corresponding to the image portion. Also, the morphology filter feeds a position signal, which represents the position of the specified picture element, and a morphology signal Dmor with respect to the picture element into the judgment means. In cases where an image portion, at which the image signal fluctuates in a spatially narrower range than the multiply structure element Bi, has not been detected, the position signal and the morphology signal Dmor are not fed out.

In cases where the position signal is received, the judgment means judges that the image portion has been detected. Also, the judgment means feeds the received position signal into the local area extracting means. In cases where it has been judged that the image portion has not been detected, no position signal is received from the morphology filter, and therefore the processing is finished.

The local area extracting means also receives the entire area image signal from the entire area image storing means. In accordance with the received entire area image signal and the received position signal, the local area extracting means specifies the picture elements (i.e., the local area constituted of the set of these picture elements), which include the picture element corresponding to the image portion, such as the abnormal pattern, and are located in the vicinity of it, according to a predetermined processing procedure. The local area extracting means thus extracts the local area limited image signal, which represents the image of the local area, from the entire area image signal.

The extracted local area limited image signal is fed into the local area limited image emphasizing means. The local area limited image emphasizing means also receives the morphology signal Dmor described above. The local area limited image emphasizing means carries out emphasis processing on the local area limited image signal (i.e., the original image signal) Dorg in accordance with the morphology signal Dmor. As described above, the morphology signal Dmor takes a large value with respect to the picture element corresponding to the image portion, at which the image signal fluctuates in a spatially narrower range than the structure element. Also, the morphology signal Dmor takes a small value with respect to picture elements other than the picture element corresponding to the image portion, at which the image signal fluctuates in a spatially narrower range than the structure element. Specifically, the morphology signal Dmor takes a small value with respect to picture elements corresponding to an image portion, at which the image signal fluctuates in a range spatially coinciding with or wider than the structure element. Therefore, by the weighting of the morphology signal Dmor and the addition of the weighted morphology signal Dmor to the original image signal Dorg, only the image portion, such as the abnormal pattern, at which the image signal fluctuates finely, can be selectively and efficiently emphasized.

An image signal Dproc is obtained from the emphasis processing carried out by the local area limited image emphasizing means. The image signal Dproc is fed into the local area limited image displaying means. In accordance with the received image signal Dproc, the local area limited image displaying means displays the local area limited image containing the image portion, such as the small calcified pattern, at which the image signal fluctuates finely.

In this manner, only the image, in which the image portion, such as the abnormal pattern, has been emphasized to a high extent, is displayed on the local area limited image displaying means. Therefore, the efficiency and the accuracy of the diagnosis, or the like, which is made by viewing the image, can be kept high.

Also, the local area limited image containing the image portion, such as the abnormal pattern, is displayed independently of the entire area image. Therefore, the person, who views the radiation image, can concentrate his attention on the local area limited image, which is displayed on the local area limited image displaying means. As a result, the efficiency and accuracy of the diagnosis, or the like, can be kept high. In cases where the entire area image displaying means also serves as the local area limited image displaying means, the image area emphasized to a high extent is only the image portion, such as the abnormal pattern, and therefore the effects of enhancing the efficiency and the accuracy of the diagnosis, or the like, can be obtained.

As described above, the image portion to be subjected to the emphasis processing is not limited to the small calcified pattern, in which the density value is smaller than the density values of the surrounding areas. For example, in accordance with the morphology operation applied, a small pattern, in which the density value is larger than the density values of the surrounding areas, can also be selectively subjected to the emphasis processing. Therefore, the third apparatus for computer aided diagnosis of images in accordance with the present invention is applicable to the high density-high signal level type of image signal and the high luminance-high signal level type of image signal. This also applies to the modifications of the third apparatus for computer aided diagnosis of images in accordance with the present invention.

Further, with the third apparatus for computer aided diagnosis of images in accordance with the present invention, wherein the local area limited image emphasizing means comprises the conversion table, which is used for converting the morphology signal Dmor into the output f(Dmor) in accordance with the morphology signal Dmor, and the abnormal pattern emphasizing means for carrying out the operation with Formula (4), the same effects as those described above can be obtained.

Furthermore, with the third apparatus for computer aided diagnosis of images in accordance with the present invention, wherein the local area limited image emphasizing means comprises the abnormal pattern emphasizing means for carrying out the operation with Formula (5) or Formula (6), the same effects as those described above can be obtained.

Also, with the third apparatus for computer aided diagnosis of images in accordance with the present invention, wherein the local area limited image emphasizing means is provided with the unsharp mask signal calculating means, the conversion table, and the abnormal pattern emphasizing means, the unsharp mask signal calculating means carries out the operation with Formula (2) in order to calculate the unsharp mask signal Dus with respect to each picture element. The conversion table is used for converting the morphology signal Dmor into the emphasis coefficient $\beta$ (Dmor) in accordance with the morphology signal Dmor. Also, the abnormal pattern emphasizing means carries out the emphasis processing with Formula (7) on the original image signal Dorg by using the unsharp mask signal Dus, the emphasis coefficient $\beta$ (Dmor), and the original image signal Dorg.

With the calculation of the second term of Formula (7), the super-low frequency component Dus is subtracted from the original image signal Dorg, and a comparatively high frequency component (i.e., the component other than the super-low frequency component) can be extracted from the original image signal Dorg. The comparatively high frequency component having thus been extracted contains radiation noise, which is a high frequency component. However, the frequency emphasis coefficient $\beta$ (Dmor), by which the comparatively high frequency component is multiplied, is based upon the morphology signal Dmor having the value in accordance with whether the picture element corresponds to or does not correspond to the image portion, such as the abnormal pattern. Therefore, even if an unnecessary component, such as quantum noise, is contained in the high frequency component (Dorg-Dus), in cases where the picture element is not the one constituting the image portion, such as the small calcified pattern, the value of $\beta$ (Dmor) with respect to the picture element will be small, and the degree of emphasis with respect to the picture element will be kept low.

In cases where the picture element is the one constituting the image portion, such as the small calcified pattern, the value of $\beta$ (Dmor) with respect to the picture element is large, and therefore the degree of emphasis with respect to the picture element is kept high.

Therefore, regardless of whether radiation noise is or is not contained in the high frequency component (Dorg-Dus) of the image, the image portion, such as the abnormal pattern, can be selectively emphasized with the function $\beta$ (Dmor), which has a value in accordance with whether the image area is or is not the image portion, such as the abnormal pattern.

BRIEF DESCRIPTION OF THE DRAWINGS

FIG. 1 is a block diagram showing a first embodiment of the apparatus for computer aided diagnosis of images in accordance with the present invention.

FIG. 11 is a block diagram showing a constitution, wherein the modification of the second embodiment shown in FIG. 8 is further provided with an entire area image emphasizing means 20 for carrying out image emphasis processing on an entire area image signal S, which represents an entire area image P displayed on an entire area image displaying means 30.

DESCRIPTION OF THE PREFERRED EMBODIMENTS

Figure 2A:
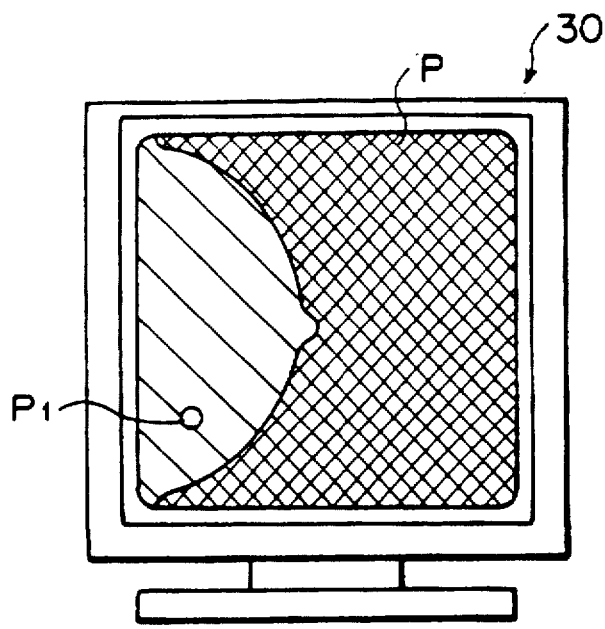
FIG. 2A is a schematic view showing an entire area image P of a radiation image, which is displayed on an entire area image displaying means.

The present invention will hereinbelow be described in further detail with reference to the accompanying drawings.

FIG. 1 is a block diagram showing a first embodiment of the apparatus for computer aided diagnosis of images in accordance with the present invention. This embodiment comprises an entire area image memory 10 for storing a digital image signal (i.e, an entire area image signal) S representing an entire radiation image (i.e., an entire area image) P of an object, and an entire area image displaying means 30, which may be constituted of a CRT display device, or the like, and which displays the entire area image P of the object in accordance with the entire area image signal S received directly from the exterior or having been stored in the entire area image memory 10. This embodiment also comprises a prospective abnormal pattern detecting means 40 for detecting a prospective abnormal pattern $P_1$ in the radiation image P in accordance with the entire area image signal S, which has been stored in the entire area image memory 10, and a judgment means 50 for making a judgment as to whether the prospective abnormal pattern $P_1$ has been or has not been detected by the prospective abnormal pattern detecting means 40. This embodiment further comprises a local area extracting means 60 which, in cases where the judgment means 50 has judged that the prospective abnormal pattern $P_1$ has been detected, extracts an image signal (i.e., a local area limited image signal) $S_2$ representing a local area limited image $P_2$ containing the prospective abnormal pattern $P_1$ from the entire area image signal S having been stored in the entire area image memory 10. This embodiment still further comprises a local area limited image displaying means 90, which may be constituted of a CRT display device, or the like, and which displays the local area limited image $P_2$ in accordance with the local area limited image signal $S_2$ having been extracted by the local area extracting means 60.

In this embodiment, by way of example, an image of the mamma having a tumor therein is taken as the radiation image P, and a tumor pattern representing the tumor is taken as the prospective abnormal pattern $P_1$. Also, an iris filter is employed as the prospective abnormal pattern detecting means 40. However, the apparatus for computer aided diagnosis of images in accordance with the present invention is not limited to such an embodiment.

With the iris filter, the gradients of the image signal (i.e., the density values), which is subjected to the detection of the tumor pattern in the radiation image, are calculated as gradient vectors, and information representing the degree of centralization of the gradient vectors is fed out. The iris filter processing is carried out with the detection processing algorithm for detecting a prospective tumor pattern in accordance with the degree of centralization of the gradient vectors, which is carried out with Formula (14). However, the term "iris filter" as used in this embodiment does not indicate the algorithm itself and indicates the means for carrying out the processing for detecting the prospective tumor pattern with the algorithm.

The term "local area" as used herein means the region, which is located in the vicinity of the tumor pattern taken as the prospective abnormal pattern and contains the tumor pattern.

How this embodiment operates will be described hereinbelow.

The entire area image signal S, which represents the radiation image P of the mamma having the tumor therein and serving as the object, is fed from an external storage medium, such as a magneto-optical disk, an image read-out apparatus, or the like, into the entire area image memory 10. Also, the entire area image signal S is fed directly from the exterior into the entire area image displaying means 30 (along a line A shown in FIG. 1). Alternatively, the entire area image signal S having been stored in the entire area image memory 10 may be fed from the entire area image memory 10 into the entire area image displaying means 30 (along a line B shown in FIG. 1). As illustrated in FIG. 2A, the entire area image displaying means 30 displays the entire area of the radiation image P in accordance with the entire area image signal S.

The radiation image P contains the prospective tumor pattern $P_1$ described above. Therefore, the entire area image P containing the prospective tumor pattern $P_1$ is displayed on the entire area image displaying means 30.

The entire area image signal S having been stored in the entire area image memory 10 is also fed into the prospective abnormal pattern detecting means (in this embodiment, the iris filter) 40. In accordance with the procedure described above, the iris filter 40 calculates the gradient vector of the received entire area image signal S representing each of picture elements of the radiation image. The iris filter 40 also calculates the degree of centralization of the gradient vector, which is given by the predetermined calculation formula and which serves as a measure for rating the degree of centralization of the direction of the gradient vector. The iris filter 40 rates the distribution of the degrees of centralization of the gradient vectors, and thereby detects an image signal $S_1$, which represents the prospective tumor pattern $P_1$.

In this manner, the picture element (and its position), which corresponds to the image signal (hereinbelow referred to as the tumor pattern image signal) $S_1$ representing the prospective tumor pattern $P_1$, is specified by the iris filter 40.

The judgment means 50 judges that the tumor pattern image signal $S_1$ representing the prospective tumor pattern $P_1$ has been detected by the iris filter 40. Also, the judgment means 50 feeds a position signal (hereinbelow referred to as the tumor picture element position signal) $D_1$, which specifies the position of the picture element represented by the tumor pattern image signal $S_1$, into the local area extracting means 60. In cases where it has been judged that the tumor pattern image signal $S_1$ representing the prospective tumor pattern $P_1$ has not been detected by the iris filter 40, the tumor picture element position signal $D_1$, which specifies the position of the picture element represented by the tumor pattern image signal $S_1$, is not fed out, and the processing is finished.

In cases where it has been judged that the tumor pattern image signal $S_1$ has been detected, the entire area image signal S having been stored in the entire area image memory 10 is also fed into the local area extracting means 60. In accordance with the received entire area image signal S and the received tumor picture element position signal $D_1$, the local area extracting means 60 specifies the picture elements (i.e., the local area constituted of the set of these picture elements), which include the picture elements corresponding to the tumor pattern image signal $S_1$ and are located in the vicinity of them, according to a predetermined processing procedure. The local area extracting means 60 thus extracts the local area limited image signal $S_2$, which represents the local area limited image $P_2$, from the entire area image signal S.

Figure 2B:
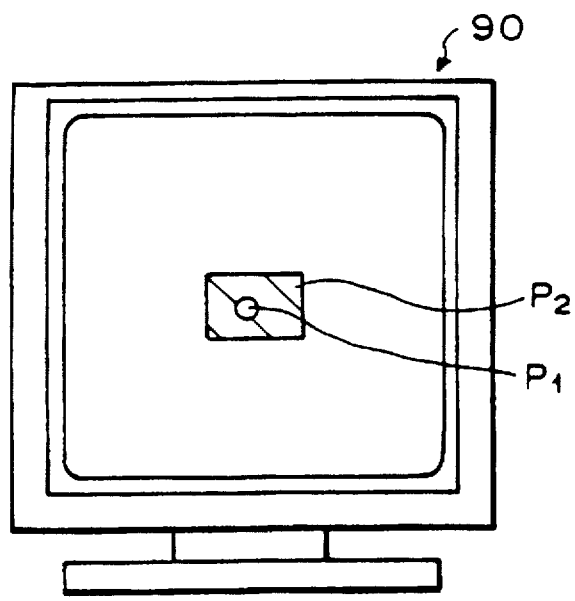
FIG. 2B is a schematic view showing a local area limited image $P_2$ containing a prospective abnormal pattern $P_1$, which is displayed on a local area limited image displaying means.

The extracted local area limited image signal $S_2$ is fed into the local area limited image displaying means 90. As illustrated in FIG. 2B, the local area limited image $P_2$ containing the prospective tumor pattern $P_1$ is displayed on the display surface of the local area limited image displaying means 90 in accordance with the local area limited image signal $S_2$.

In this manner, of the entire area image P, only the local area limited image $P_2$ containing the prospective tumor pattern $P_1$ is independently displayed on the local area limited image displaying means 90. Therefore, the person, who views the radiation image, can concentrate his attention on the local area limited image $P_2$, which is displayed on the local area limited image displaying means 90. As a result, the efficiency and the accuracy of the diagnosis, or the like, can be kept high, and the time required for making the diagnosis, or the like, can be kept short.

In this embodiment, the entire area image signal S is fed via the entire area image memory 10 into the prospective abnormal pattern detecting means 40 (along a line b shown in FIG. 1). Alternatively, the entire area image signal S may be fed directly from the magneto-optical disk, an image read-out apparatus, or the like, into the prospective abnormal pattern detecting means 40 (along a line a shown in FIG. 1).

This also applies to the embodiments, which will be described later.

Also, in this embodiment, the mamma having a tumor therein is taken as the object, the tumor pattern representing the tumor is taken as the prospective abnormal pattern, and the iris filter is employed as the prospective abnormal pattern detecting means. However, the apparatus for computer aided diagnosis of images in accordance with the present invention is not limited to such an embodiment. For example, the mamma having a cancerous portion forming a calcified pattern, in which very fine high-density regions are distributed slightly densely, may be taken as the object, and the calcified pattern may be taken as the prospective abnormal pattern. Also, the aforesaid morphology filter for carrying out the processing for detecting the calcified pattern may be employed as the prospective abnormal pattern detecting means.

When the prospective abnormal pattern is displayed on the local area limited image displaying means, the characteristic measures of the prospective abnormal pattern, which were taken in the detection of the prospective abnormal pattern carried out by the prospective abnormal pattern detecting means, (specifically, the value of the degree of centralization of the gradient vectors and the extent of the irregularity of tumor pattern side edges in the cases of the tumor pattern, or the calcification density in the case of the calcified pattern) may be displayed as the quantitatively determined information on the local area limited image displaying means together with the prospective abnormal pattern.

Figure 3:
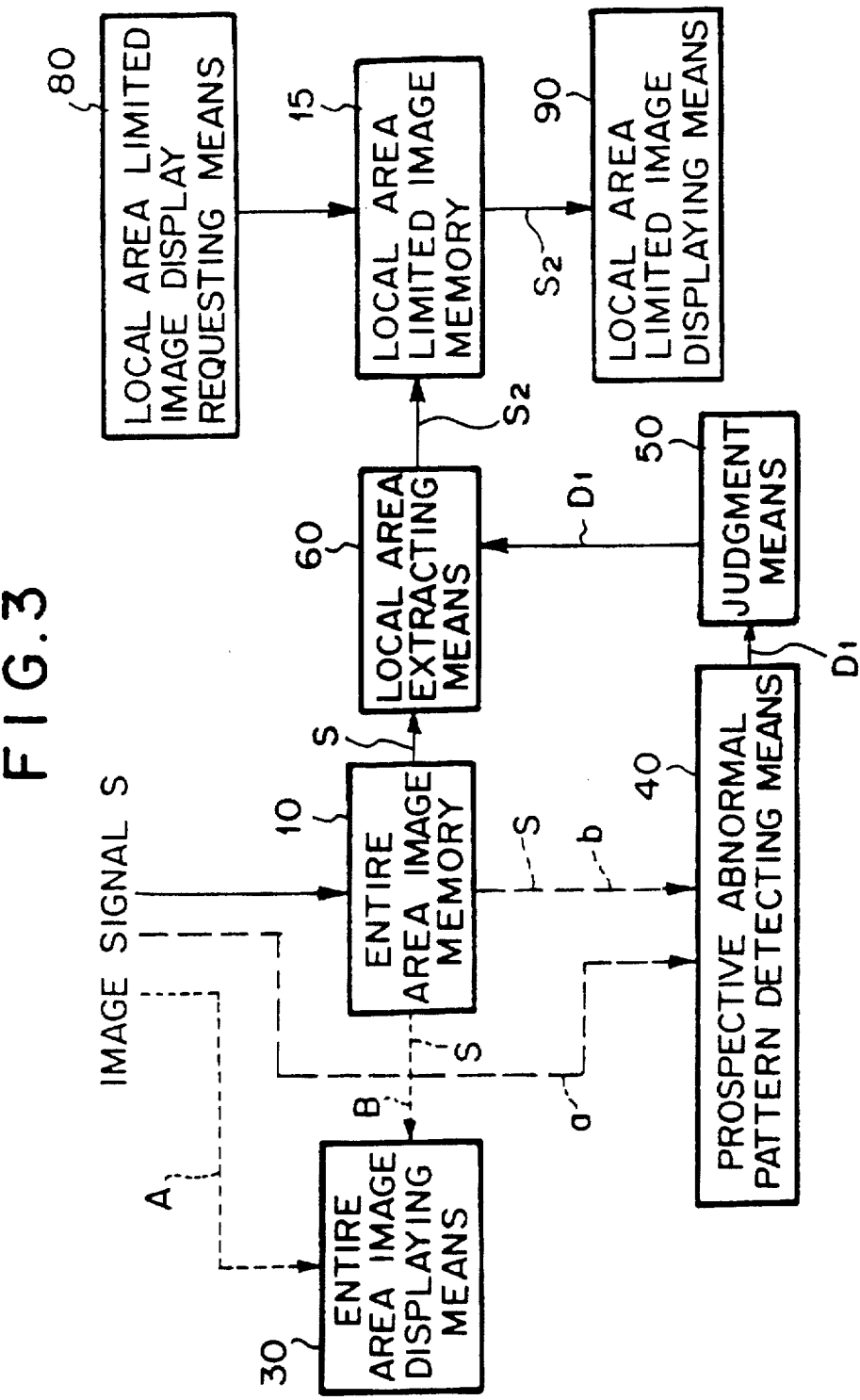
FIG. 3 is a block diagram showing a second embodiment of the apparatus for computer aided diagnosis of images in accordance with the present invention.

FIG. 3 is a block diagram showing a second embodiment of the apparatus for computer aided diagnosis of images in accordance with the present invention. The second embodiment is the same as the first embodiment of FIG. 1, except that the second embodiment further comprises a local area limited image memory 15 and a local area limited image display requesting means 80, which are located between the local area extracting means 60 and the local area limited image displaying means 90. The local area limited image memory 15 temporarily stores the local area limited image signal $S_2$. Only when a predetermined image display request is received from the exterior, the local area limited image display requesting means 80 causes the local area limited image signal $S_2$ to be fed out from the local area limited image memory 15 and causes the local area limited image $P_2$ to be displayed on the local area limited image displaying means 90.

Specifically, in the same manner as that in the first embodiment, the local area extracting means 60 extracts the local area limited image signal $S_2$ in accordance with the results of the judgment made by the judgment means 50. The local area limited image signal $S_2$, which has been extracted by the local area extracting means 60, is fed into and temporarily stored in the local area limited image memory 15, and the processing is temporarily ceased. When the person, who views the radiation image, feeds a signal, which represents a request for displaying the local area limited image, into the local area limited image display requesting means 80, the signal representing the request for displaying the local area limited image is fed from the local area limited image display requesting means 80 into the local area limited image memory 15. In accordance with this signal, the local area limited image memory 15 feeds the stored local area limited image signal $S_2$ into the local area limited image displaying means 90, and the processing is thus resumed.

With the second embodiment, the local area limited image signal $S_2$, which represents the local area limited image containing the detected prospective abnormal pattern, is temporarily stored in the local area limited image memory 15. Therefore, the person, who views the radiation image, can arbitrarily determine whether to display the local area limited image on the local area limited image displaying means 90 or not in accordance with circumstances, such as the time available for the image viewing. Specifically, ordinarily, the person, who views the radiation image, firstly views the entire area image in order to recognize the entire image information to some extent, and thereafter views a detail structure. Therefore, with the second embodiment, the person, who views the radiation image, can firstly view the entire area image displayed on the entire area image displaying means 30. At a desired point of time after or during the viewing of the entire area image, the person, who views the radiation image, can immediately display the local area limited image, which contains the prospective abnormal pattern, on the local area limited image displaying means 90 by carrying out a simple operation for making a display request to the local area limited image display requesting means 80. Thus the apparatus for computer aided diagnosis of images can be operated in accordance with the actual circumstances at the sites of medical treatment, or the like.

Figure 4:
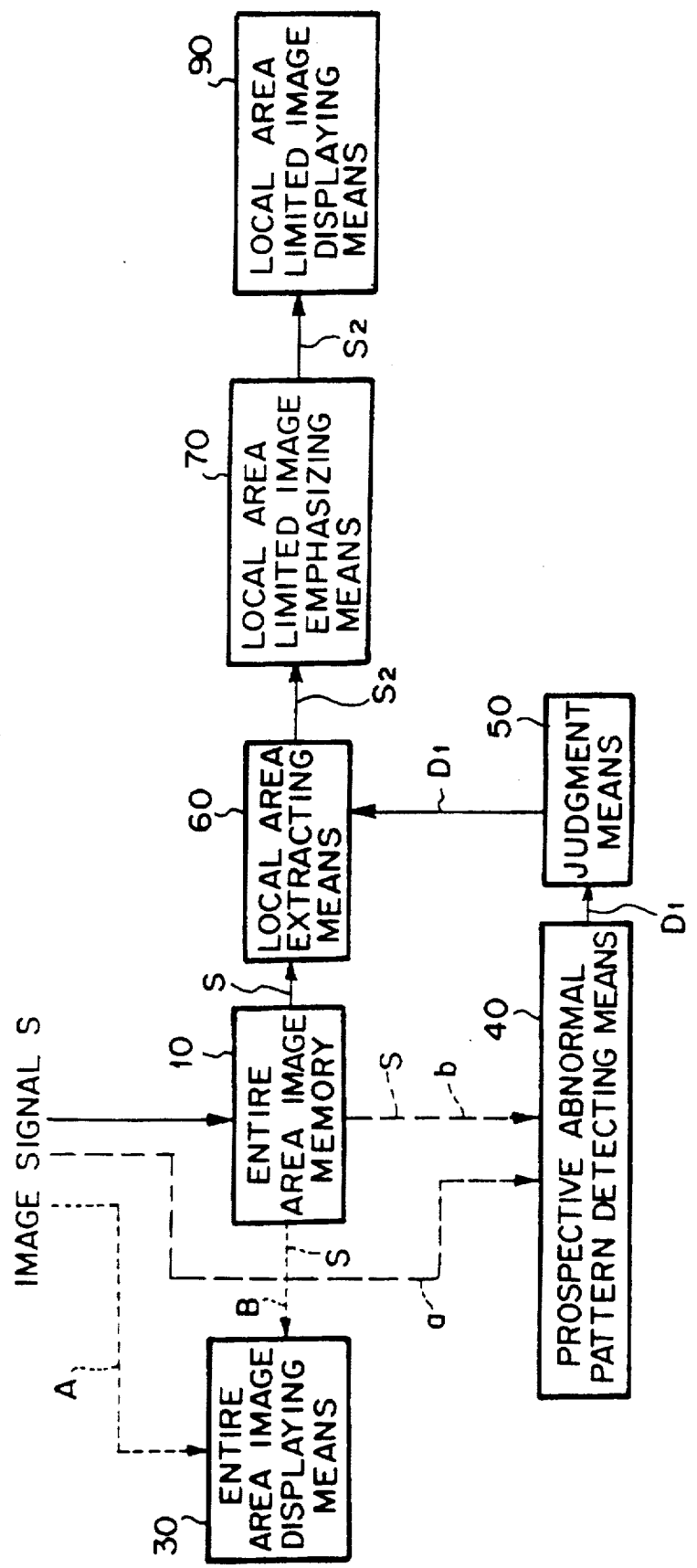
FIG. 4 is a block diagram showing a third embodiment of the apparatus for computer aided diagnosis of images in accordance with the present invention.

FIG. 4 is a block diagram showing a third embodiment of the apparatus for computer aided diagnosis of images in accordance with the present invention. The third embodiment is the same as the first embodiment, except that the third embodiment further comprises a local area limited image emphasizing means 70. The local area limited image emphasizing means 70 carries out image emphasis processing on at least the abnormal pattern image signal $S_1$, which is among the local area limited image signal $S_2$, such that at least the prospective abnormal pattern $P_1$ in the local area limited image $P_2$, which is displayed on the local area limited image displaying means 90, may have better image quality and higher capability of serving as an effective tool in, particularly, the efficient and accurate diagnosis of an illness than the entire area image P, which is displayed on the entire area image displaying means 30.

Figure 5A:
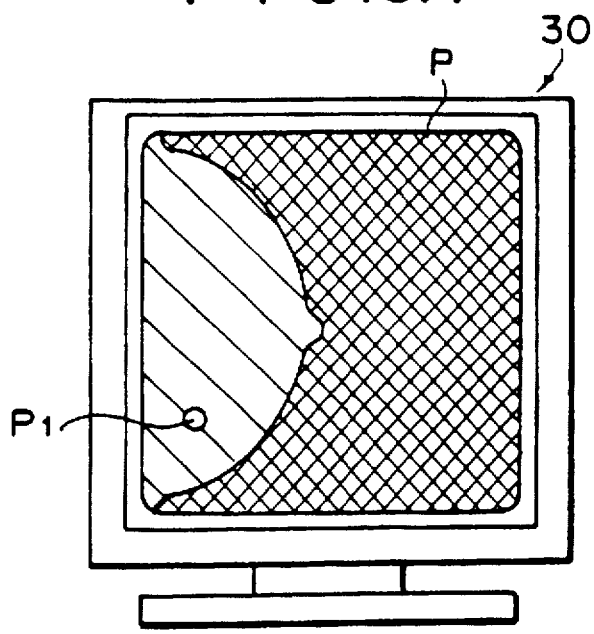
FIG. 5A is a schematic view showing an entire area image P of a radiation image, which is displayed on an entire area image displaying means.

Specifically, the entire area image signal S is fed into the entire area image displaying means 30 directly from the exterior (along a line A shown in FIG. 4) or via the entire area image memory 10 (along a line B shown in FIG. 4). As illustrated in FIG. 5A, the entire area image P is displayed on the entire area image displaying means 30. In the same manner as that in the first embodiment, the local area extracting means 60 extracts the local area limited image signal $S_2$ in accordance with the results of the judgment made by the judgment means 50. The local area limited image signal $S_2$, which has been extracted by the local area extracting means 60, is fed into the local area limited image emphasizing means 70 and is thereby subjected to the image emphasis processing, such as the gradation processing, the frequency processing, and the enlargement processing.

Specifically, the image emphasis processing is set in the manner described in (1), (2), and (3) below.

(1) The gradation processing is set such that the level of contrast of the local area limited image $P_2$, which is displayed on the local area limited image displaying means 90, may become at least 1.2 times as high as the level of contrast of the entire area image P, which is displayed on the entire area image displaying means 30.

(2) The frequency processing is set such that the degree of emphasis of the local area limited image $P_2$, which is displayed on the local area limited image displaying means 90, may become at least 1.1 times as high as the degree of emphasis of the entire area image P, which is displayed on the entire area image displaying means 30.

(3) The enlargement processing is set so that the display size of the local area limited image $P_2$, which is displayed on the local area limited image displaying means 90, may become at least 1.5 times as large as the display size of the local area limited image in the entire area image P, which is displayed on the entire area image displaying means 30.

Figure 5B:
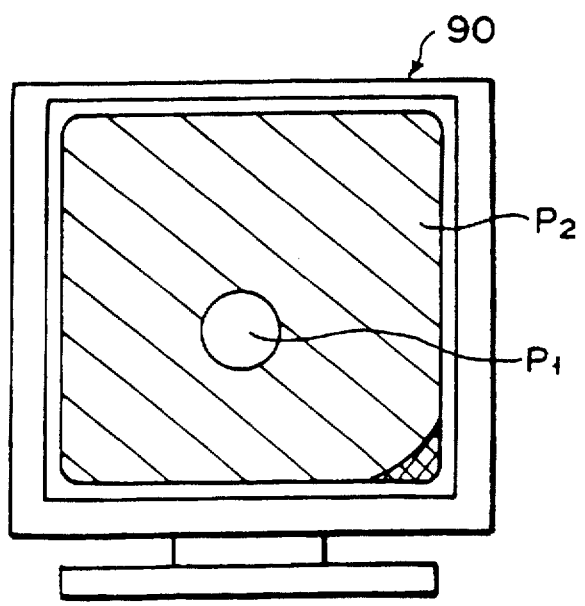
FIG. 5B is a schematic view showing a local area limited image $P_2$ containing a prospective abnormal pattern $P_1$, which is displayed on a local area limited image displaying means.

The local area limited image signal $S_2$, which has been obtained from the image emphasis processing, is fed into the local area limited image displaying means 90. As illustrated in FIG. 5B, the local area limited image displaying means 90 displays the local area limited image $P_2$ in accordance with the received local area limited image signal $S_2$. By the setting in the local area limited image emphasizing means 70, the level of contrast of the local area limited image $P_2$, which is displayed on the local area limited image displaying means 90, is at least 1.2 times as high as the level of contrast of the entire area image P, which is displayed on the entire area image displaying means 30. Also, the degree of emphasis of the local area limited image $P_2$, which is displayed on the local area limited image displaying means 90, is at least 1.1 times as high as the degree of emphasis of the entire area image P, which is displayed on the entire area image displaying means 30. Further, the display size of the local area limited image $P_2$, which is displayed on the local area limited image displaying means 90, is at least 1.5 times as large as the display size of the local area limited image in the entire area image P, which is displayed on the entire area image displaying means 30. Therefore, the local area limited image $P_2$, which is displayed on the local area limited image displaying means 90, has better image quality and higher capability of serving as an effective tool in, particularly, the efficient and accurate diagnosis of an illness. Also, only the local area limited image $P_2$ is displayed on the local area limited image displaying means 90 independently of the entire area image P. Accordingly, the person, who views the radiation image, can concentrate his attention on the local area limited image $P_2$, which contains the prospective tumor pattern $P_1$. As a result, the efficiency and the accuracy of the diagnosis, or the like, can be kept high, and the time required for making the diagnosis, or the like, can be kept short.

In the local area limited image emphasizing means 70, the image emphasis processing, such as the gradation processing, the frequency processing, and the enlargement processing, need not necessarily be carried out on the entire local area limited image signal $S_2$ and may be carried out only on the abnormal pattern image signal $S_1$, which is other than the image signal corresponding to the neighboring region in the local area limited image signal $S_1$. In cases where the image emphasis processing is thus carried out only on the abnormal pattern image signal $S_1$, the aforesaid values of the enhancement of the contrast, the degree of emphasis, and the display size are taken as the values for the prospective abnormal pattern P with respect to the entire area image. Specifically, the image emphasis processing carried out by the local area limited image emphasizing means 70 is set in the manner described in (1'), (2'), and (3') below.

(1') The gradation processing is set such that the level of contrast of the prospective abnormal pattern $P_1$, which is displayed on the local area limited image displaying means 90, may become at least 1.2 times as high as the level of contrast of the entire area image P, which is displayed on the entire area image displaying means 30.

(2') The frequency processing is set such that the degree of emphasis of the prospective abnormal pattern $P_1$, which is displayed on the local area limited image displaying means 90, may become at least 1.1 times as high as the degree of emphasis of the entire area image P, which is displayed on the entire area image displaying means 30.

(3') The enlargement processing is set so that the display size of the prospective abnormal pattern $P_1$, which is displayed on the local area limited image displaying means 90, may become at least 1.5 times as large as the display size of the prospective abnormal pattern in the entire area image P, which is displayed on the entire area image displaying means 30.

The enlargement processing is not limited to the enlargement processing in which the scale of enlargement is fixed at, for example, 1.5 as described above. The enlargement processing may be set such that the scale of enlargement may be changed in accordance with the size of the prospective abnormal pattern, which has been detected by the prospective abnormal pattern detecting means 40. Specifically, when the prospective abnormal pattern $P_1$ is displayed on the local area limited image displaying means 90, in cases where the size of the detected prospective abnormal pattern is small, the enlargement processing may be carried out with a comparatively large scale of enlargement. In cases where the size of the detected prospective abnormal pattern is large, the enlargement processing may be carried out with a comparatively small scale of enlargement. Thus the enlargement processing may be carried out such that the apparent size of the prospective abnormal pattern on the display surface of the local area limited image displaying means 90 may become approximately equal to a predetermined size regardless of the actual size of the prospective abnormal pattern.

Figure 6:
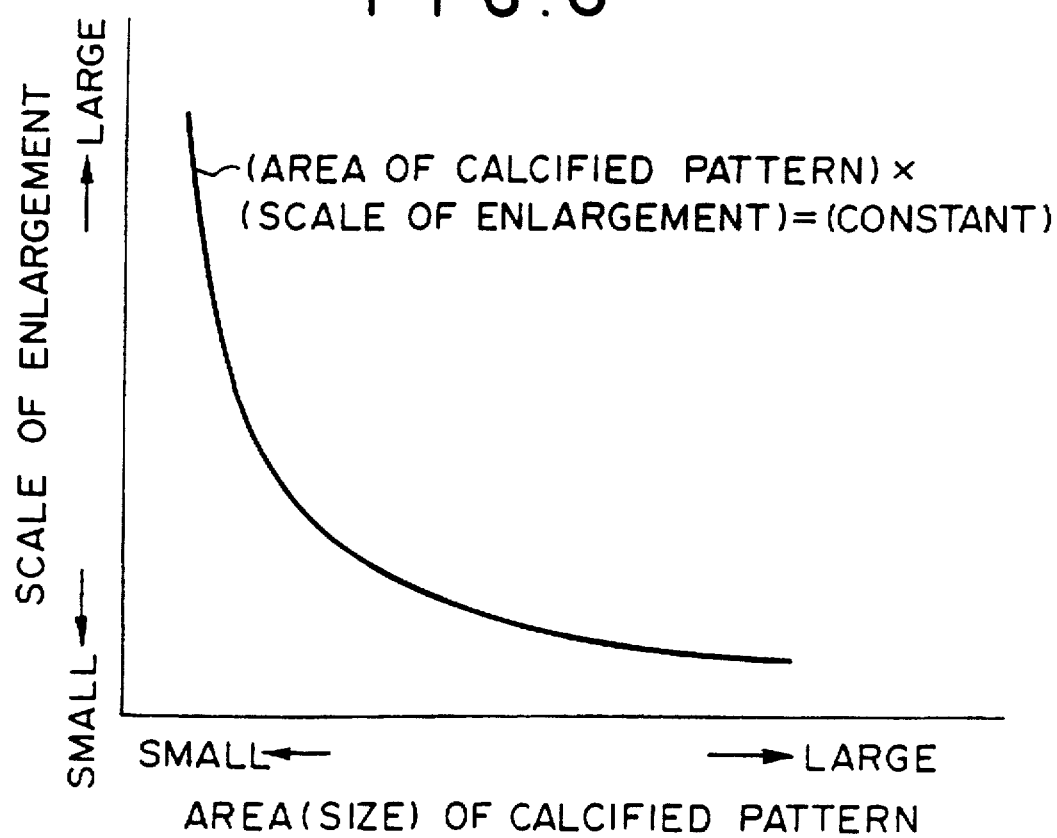
FIG. 6 is a graph showing an enlargement scale setting table, in which the scale of enlargement is set in accordance with the size of a prospective abnormal pattern having been calculated with an abnormal pattern size calculating means.

Specifically, the local area limited image emphasizing means 70 may comprise (a) an abnormal pattern size calculating means for calculating the size of the prospective abnormal pattern in accordance with the position signal $D_1$ representing the position of the prospective abnormal pattern, which signal has been obtained from the prospective abnormal pattern detecting means, (b) an enlargement scale setting table (shown in FIG. 6), in which the scale of enlargement in accordance with the size of the prospective abnormal pattern calculated by the abnormal pattern size calculating means has been set previously such that the size of the image of the prospective abnormal pattern displayed on the local area limited image displaying means 90 may become approximately equal to a predetermined size, and (c) an enlargement processing means for carrying out the enlargement processing on the local area limited image signal $S_2$ or the abnormal pattern image signal $S_1$.

In this manner, the scale of enlargement may be changed such that the size of the prospective abnormal pattern $P_1$ displayed on the local area limited image displaying means 90 may become approximately equal to a predetermined size regardless of the size of the prospective abnormal pattern detected. In such cases, even if the size of the prospective abnormal pattern detected is small, the person, who views the radiation image, can view the prospective abnormal pattern $P_1$ as an image having a size approximately equal Lo a predetermined size. Therefore, the efficiency and the accuracy of the diagnosis, or the like, can be kept high.

The calculation of the size of the prospective abnormal pattern with the abnormal pattern size calculating means may be made in accordance with, for example, the peripheral edge length of the prospective abnormal pattern, such as the tumor pattern or the calcified pattern. Alternatively, in cases where the prospective abnormal pattern detecting means 40 is the morphology filter, the size of the prospective abnormal pattern may be calculated with the technique described below.

Specifically, in cases where the value P of Formula (21) based on the aforesaid opening operation (i.e., the density value of the calcified pattern calculated with the morphology filter) is not smaller than a predetermined threshold value Th (i.e., $P \geq Th$), which is used to judge whether a picture element corresponds or does not correspond to the prospective abnormal pattern (prospective calcified pattern), the picture element is regarded as corresponding to the prospective calcified pattern, and a value of "1" is allocated to the picture element. In cases where the value P of Formula (21) is smaller than the predetermined threshold value Th (i.e., $P<Th$), the picture element is regarded as not corresponding to the prospective calcified pattern, and a value of "0" is allocated to the picture element. In this manner, the characteristics of each picture element are binarized. The size of the prospective abnormal pattern is then calculated from the total sum or the mean value of the number of the picture elements, which has been regarded as corresponding to the prospective calcified pattern and allocated with the value of "1."

$$P = f - \max\{(f \ominus Bi) \oplus Bi\} \quad (21)$$
$$i \in (1, \ldots, M)$$
$$= f - \max\{f_{Bi}\}$$
$$i \in (1, \ldots, M)$$

Figure 7:
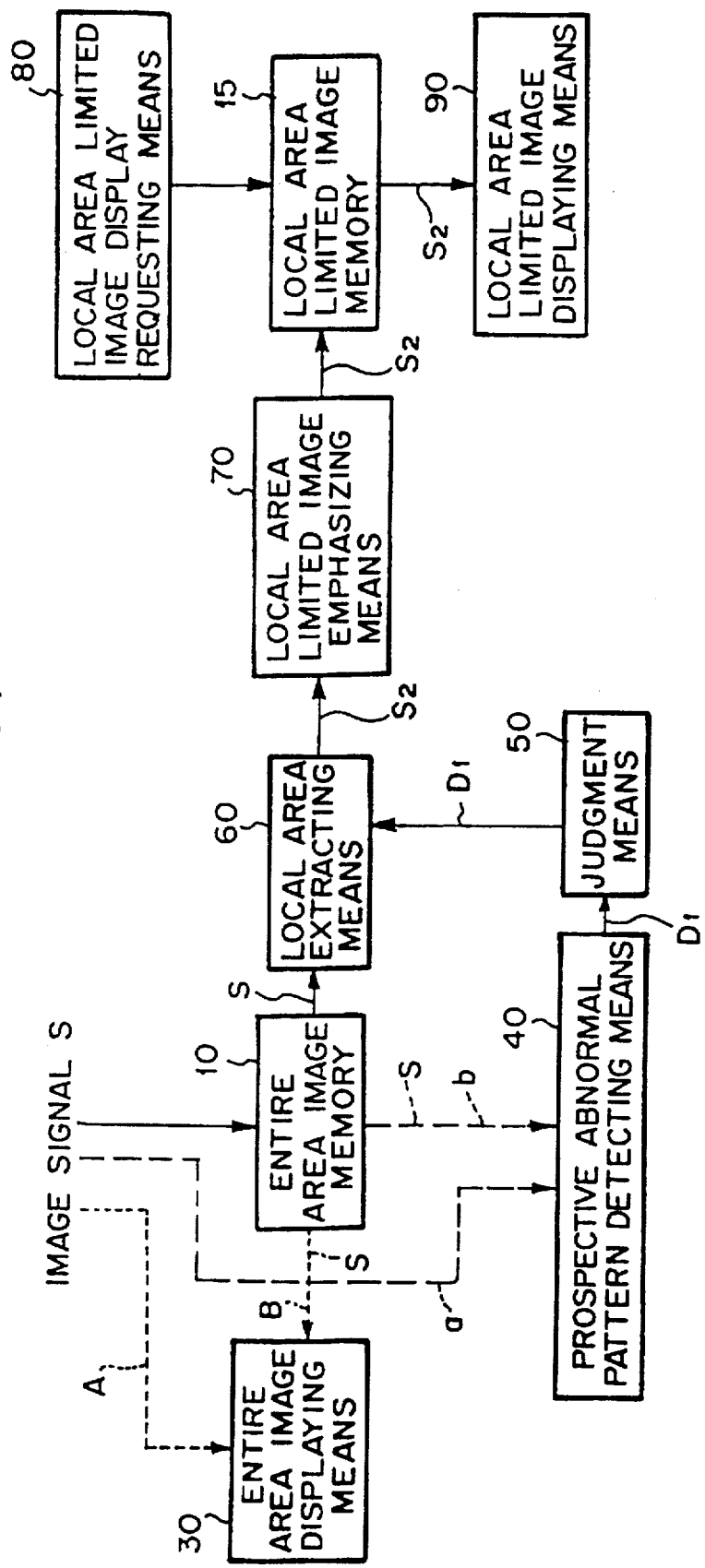
FIG. 7 is a block diagram showing a modification of the second embodiment of FIG. 3, which is provided with a local area limited image emphasizing means 70 for carrying out image emphasis processing on a local area limited image signal $S_2$ received from a local area extracting means 60.
Figure 8:
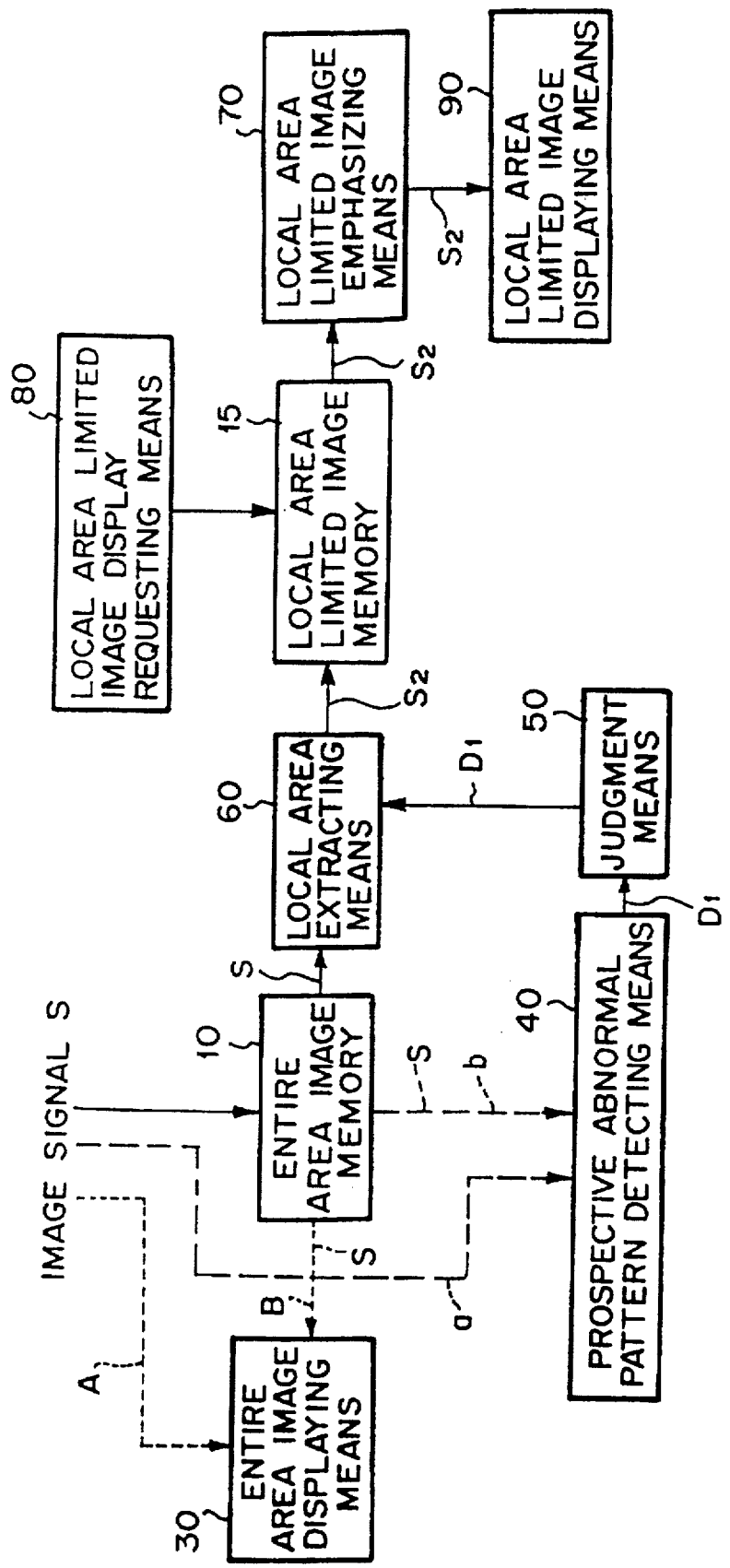
FIG. 8 is a block diagram showing a modification of the second embodiment of FIG. 3, which is provided with a local area limited image emphasizing means 70 for carrying out image emphasis processing on a local area limited image signal $S_2$ received from a local area limited image memory 15.

The aforesaid local area limited image emphasizing means 70 may be applied to the second embodiment of the apparatus for computer aided diagnosis of images in accordance with the present invention. Specifically, as illustrated in FIG. 7, the local area limited image emphasizing means 70 may be located such that it may carry out the image emphasis processing on the local area limited image signal $S_2$, which has been received from the local area extracting means 60. Alternatively, as illustrated in FIG. 8, the local area limited image emphasizing means 70 may be located such that it may carry out the image emphasis processing on the local area limited image signal $S_2$, which has been received from the local area limited image memory 15.

In the modification of FIG. 7, the local area limited image signal $S_2$, which has been obtained from the image emphasis processing carried out by the local area limited image emphasizing means 70, is temporarily stored in the local area limited image memory 15. When a display request is made, the local area limited image signal $S_2$ is fed from the local area limited image memory 15 into the local area limited image displaying means 90, and the local area limited image $P_2$ in accordance with the local area limited image signal $S_2$ is displayed on the local area limited image displaying means 90 as illustrated in FIG. 5B.

Figure 9:
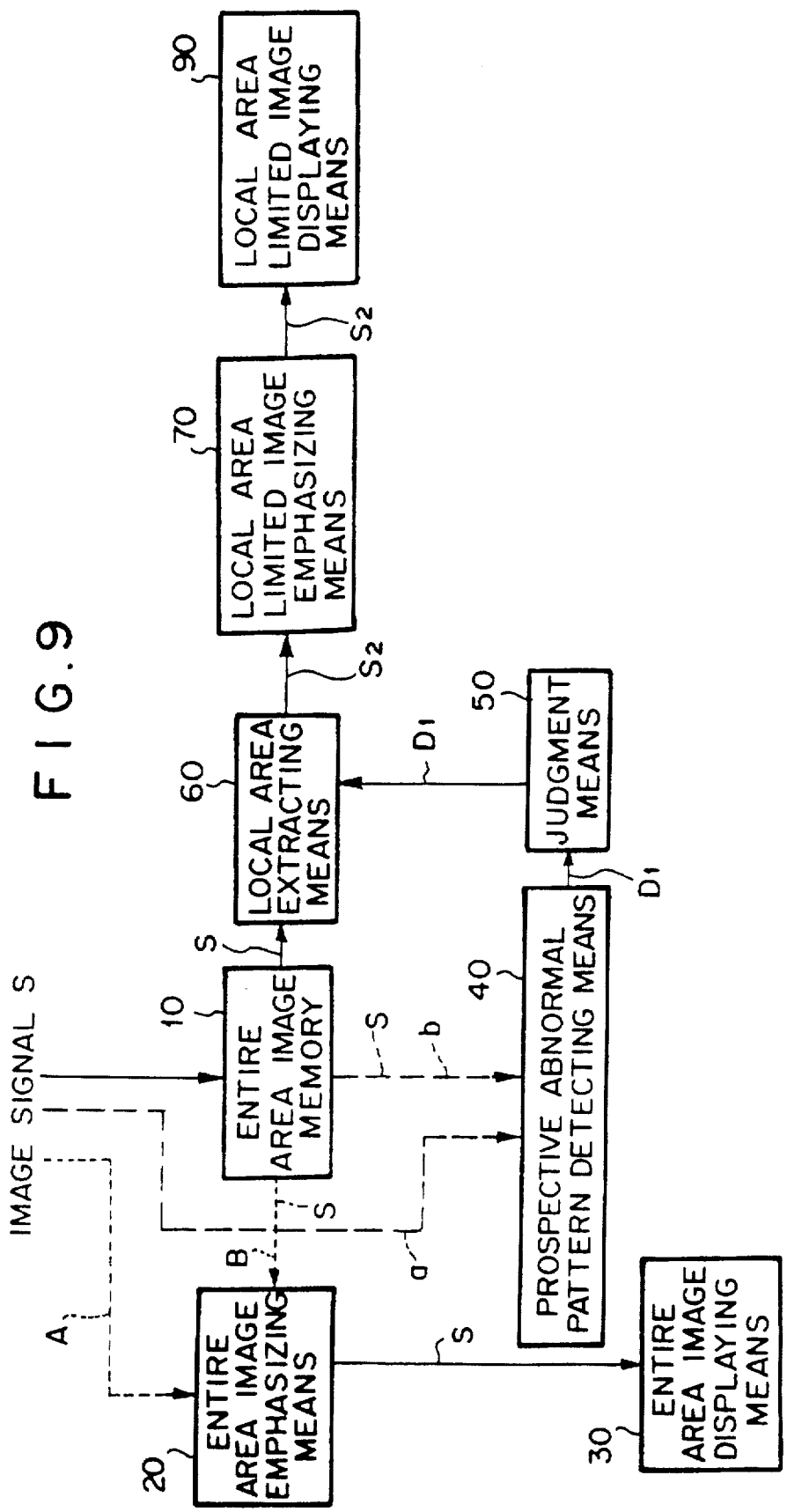
FIG. 9 is a block diagram showing a fourth embodiment of the apparatus for computer aided diagnosis of images in accordance with the present invention.

FIG. 9 is a block diagram showing a fourth embodiment of the apparatus for computer aided diagnosis of images in accordance with the present invention. The fourth embodiment is the same as the third embodiment of FIG. 4, except that the fourth embodiment further comprises an entire area image emphasizing means 20, which carries out the image emphasis processing, such as the gradation processing, the frequency processing, or the combination of them, on the entire area image signal S representing the entire area image P, which is to be displayed on the entire area image displaying means 30.

Specifically, in the same manner as that in the aforesaid third embodiment, the local area limited image $P_2$ is displayed on the local area limited image displaying means 90. Also, the entire area image signal S having been given to the apparatus is fed into the entire area image emphasizing means 20 directly from the exterior (along a line A shown in FIG. 9) or via the entire area image memory 10 (along a line B shown in FIG. 9). The entire area image emphasizing means 20 carries out the image emphasis processing, such as the gradation processing, the frequency processing, or the combination of them, on the received entire area image signal S. The entire area image signal S having been obtained from the image emphasis processing is fed into the entire area image displaying means 30. The entire area image displaying means 30 displays the entire area image P in accordance with the received entire area image signal S.

By the image emphasis processing carried out to a certain extent on the entire area image, the entire area image P having good image quality can be displayed and used as an effective tool in, particularly, the accurate and efficient diagnosis of an illness.

The entire area image emphasizing means 20 aims at enhancing the image quality of the entire area image P and its capability of serving as an effective tool in, particularly, the efficient and accurate diagnosis of an illness. Therefore, in cases where the constitution for carrying out the image emphasis processing also on the entire area image P is employed, the local area limited image $P_2$ (or the prospective abnormal pattern $P_1$), which is obtained from the image emphasis processing carried out by the local area limited image emphasizing means 70, has better image quality and higher capability of serving as an effective tool in, particularly, the efficient and accurate diagnosis of an illness than the local area limited image $P_2$ (or the prospective abnormal pattern $P_1$), which is contained in the entire area image P obtained from the image emphasis processing carried out by the entire area image emphasizing means 20.

Figure 10:
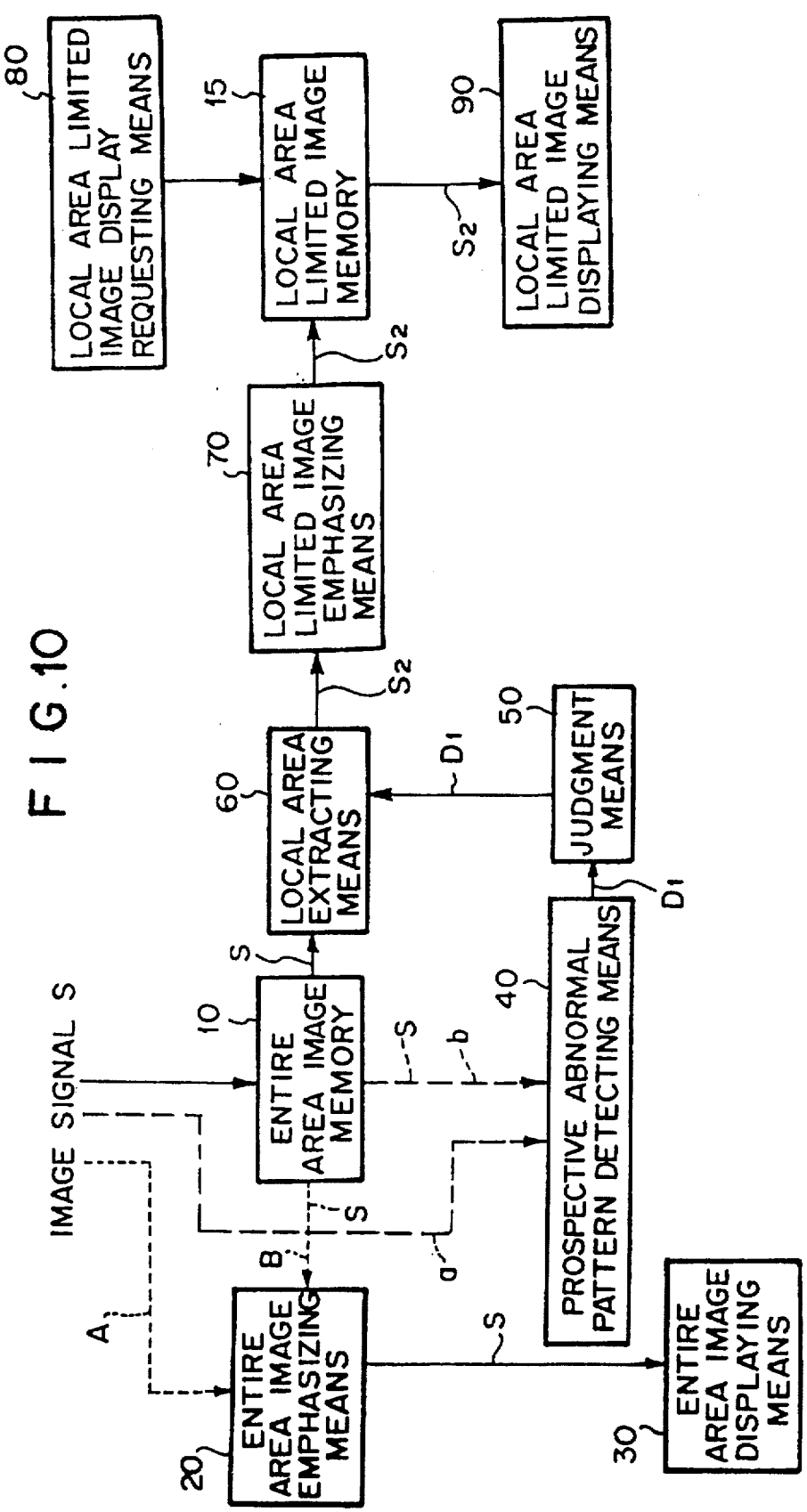
FIG. 10 is a block diagram showing a constitution, wherein the modification of the second embodiment shown in FIG. 7 is further provided with an entire area image emphasizing means 20 for carrying out image emphasis processing on an entire area image signal S, which represents an entire area image P displayed on an entire area image displaying means 30.

FIGS. 10 and 11 shows constitutions modified in the same manner as that in the fourth embodiment. FIG. 10 is a block diagram showing a constitution, wherein the modification of the second embodiment shown in FIG. 7 is further provided with the entire area image emphasizing means 20 for carrying out image emphasis processing, such as the gradation processing, the frequency processing, or the combination of them, on the entire area image signal S, which represents the entire area image P displayed on the entire area image displaying means 30. FIG. 11 is a block diagram showing a constitution, wherein the modification of the second embodiment shown in FIG. 8 is further provided with the entire area image emphasizing means 20 for carrying out image emphasis processing on the entire area image signal S, which represents the entire area image P displayed on the entire area image displaying means 30. The constitution shown in FIG. 10 or FIG. 11 are the same as the modification of the second embodiment shown in FIG. 7 or FIG. 8, except that the entire area image emphasizing means 20 is further provided.

In the constitution shown in FIG. 10 or FIG. 11, the local area limited image $P_2$ is displayed on the local area limited image displaying means 90 in the same manner as that in the modification of the second embodiment shown in FIG. 7 or FIG. 8. Also, the entire area image P is displayed on the entire area image displaying means 30 in the same manner as that in the fourth embodiment of FIG. 9.

Figure 12:
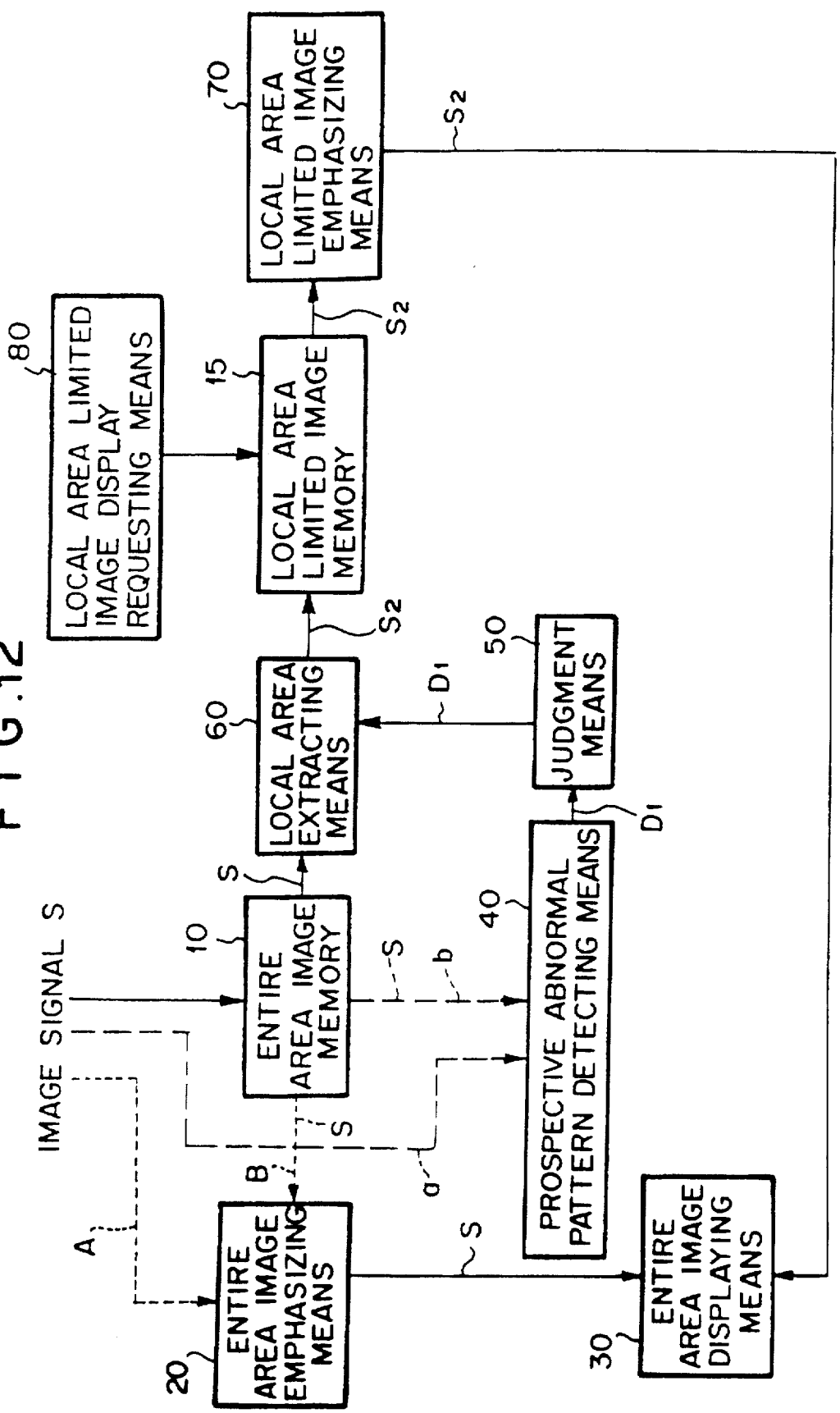
FIG. 12 is a block diagram showing a constitution, wherein the entire area image displaying means 30 in the constitution of FIG. 11 also serves as a local area limited image displaying means 90.
Figure 13:
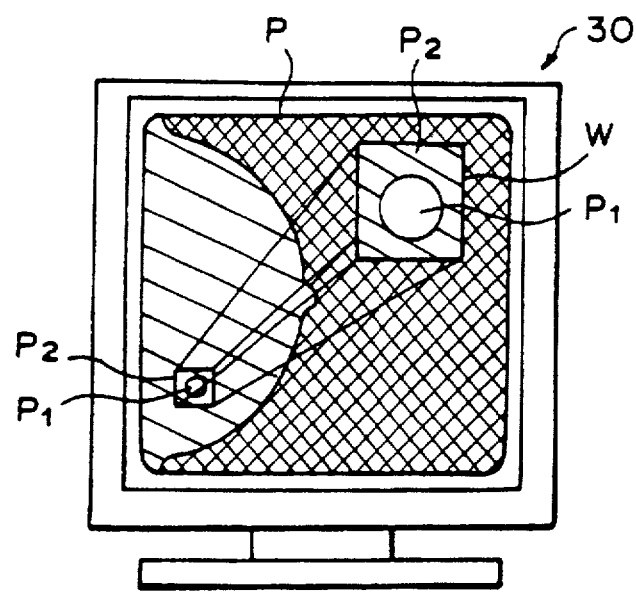
FIG. 13 is an explanatory view showing how an entire area image and a local area limited image are displayed in the constitution, in which an entire area image displaying means also serves as a local area limited image displaying means.

FIG. 12 is a block diagram showing a constitution, wherein the entire area image displaying means 30 in the constitution of FIG. 11 also serves as the local area limited image displaying means 90. Specifically, the constitution of FIG. 11 is modified such that a window region W, in which the local area limited image $P_2$ is to be displayed, may be located at a portion of the display surface of the entire area image displaying means 30, on which the entire area image P is being displayed. Therefore, as illustrated in FIG. 13, while the entire area image P is being displayed on the entire area image displaying means 30, the local area limited image $P_2$, which will otherwise be displayed on the independent local area limited image displaying means 90, is displayed at a portion of the entire area image P, which is being displayed on the entire area image displaying means 30. (This means that, in the window region W of the entire area image displaying means 30, at which region the local area limited image $P_2$ is displayed, the portion of the entire area image P and the local area limited image $P_2$ are not superposed one upon the other, but instead only the local area limited image $P_2$ is displayed without the portion of the entire area image P being displayed. At the other portion of the display surface of the entire area image displaying means 30, the remaining portion of the entire area image P is displayed.) The window region W is set by a display control means (not shown).

In the constitution of FIG. 12, before a display request is made by the person, who views the radiation image, to the local area limited image display requesting means 80, only the entire area image P is displayed over the entire display surface of the entire area image displaying means 30. When a display request is made, as illustrated in FIG. 13, the window region W is set on the entire area image displaying means 30, and the local area limited image $P_2$ is displayed in the window region W in the manner described above.

In cases where the entire area image P and the local area limited image $P_2$ containing the prospective abnormal pattern $P_1$ are displayed simultaneously on the same display surface of the single display means, the position of the prospective abnormal pattern $P_1$ in the entire area image P can be understood more easily. Therefore, the efficiency and the accuracy of the diagnosis, or the like, can be kept high.

The entire area image P and the local area limited image $P_2$ may be displayed in various manners in accordance with the kind of the object, the image of which is displayed. For example, in cases where the X-ray image of the mamma, or the like, of a single patient is displayed, only the image of the single mamma may be displayed. Alternatively, for example, two entire area image displaying means and/or two local area limited image displaying means may be provided. In this manner, the local area limited image $P_2$ containing the abnormal pattern in one of the two mammae of the patient may be displayed on one of the two local area limited image displaying means. At the same time, a local area limited image $P_2'$ of the portion of the other mamma, which portion corresponds to the local area of the one mamma, may be subjected to the same emphasis processing as that for the local area limited image $P_2$ of the one mamma and displayed on the other local area limited image displaying means. In such cases, the person, who views the radiation image, can compare the corresponding portions $P_2$ and $P_1'$ of the right and left mammae of the single patient. Accordingly, the efficiency and the accuracy of the diagnosis can be enhanced even further.

Also, as for the entire area image displaying means, the entire area images of a pair of the mammae of the single patient may be respectively displayed on two independent entire area image displaying means.

Further, the aforesaid window region may be located on each of the two entire area image displaying means. Each of the images of the corresponding local areas of the right and left mammae may be displayed together with one of the entire area images of the two mamma, which are displayed respectively on the two entire area image displaying means.

Figure 14A:
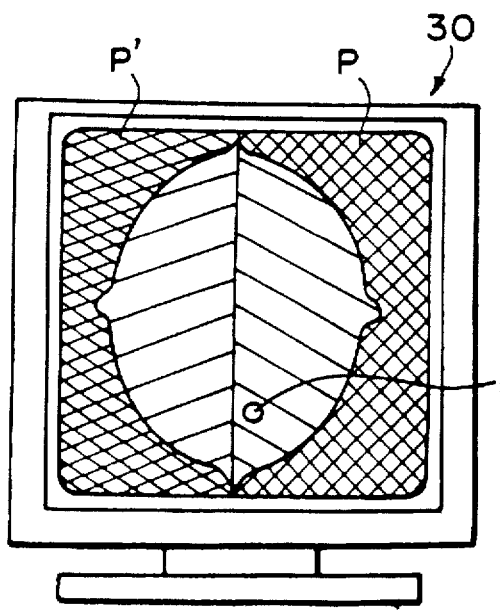
FIG. 14A is an explanatory view showing how the images of two mammae are simultaneously displayed on an entire area image displaying means.
Figure 14B:
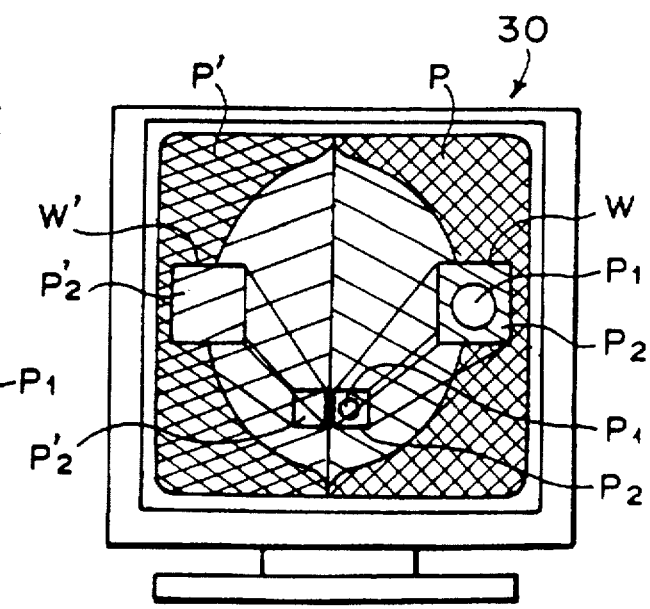
FIG. 14B is an explanatory view showing how the images of two mammae are simultaneously displayed on an entire area image displaying means and how the entire area images and local area limited images are displayed in the constitution, in which an entire area image displaying means also serves as a local area limited image displaying means.

Furthermore, the image of one of the mammae of the single patient and the image of the other mamma, which has been recorded independently of the image of the one mamma, may be simultaneously displayed on the display surface of the same image displaying means. Specifically, as illustrated in FIG. 14A, an entire area image P of the one mamma may be displayed at the right half of the display surface of the entire area image displaying means 30, and an entire area image P' of the other mamma may be displayed simultaneously at the left half of the display surface of the same entire area image displaying means 30, such that the two entire area images P and P' may be adjacent to each other (for example, such that the front sides of the two images may stand facing each other, or the back sides of the two images may stand facing each other). As illustrated in FIG. 14B, in cases where the prospective abnormal pattern P is detected from the entire area image signal S, which represents the image of the one mamma, the local area limited image $P_2$ containing the prospective abnormal pattern $P_1$ may be subjected to the emphasis processing and then displayed in a window region W, which is located in the right half of the display surface. Also, the local area limited image $P_2'$ of the portion of the other mamma, which portion corresponds to the position of the prospective abnormal pattern $P_1$ in the one mamma, may be subjected to the same emphasis processing and displayed in a window region W', which is located in the left half of the display surface.

With this constitution, the images of the two mammae of the single patient can be directly compared with each other, and therefore a detail deference between the two mammae, such as a difference in the presence or absence of an abnormal pattern or the shape or form of the abnormal pattern, can be found easily.

Locating the window region W on the entire area image displaying means 30 and displaying the entire area image and the local area limited image on the single display surface may be carried out in various ways. How the size and the position of the window region are set will be described hereinbelow.

Figure 15:
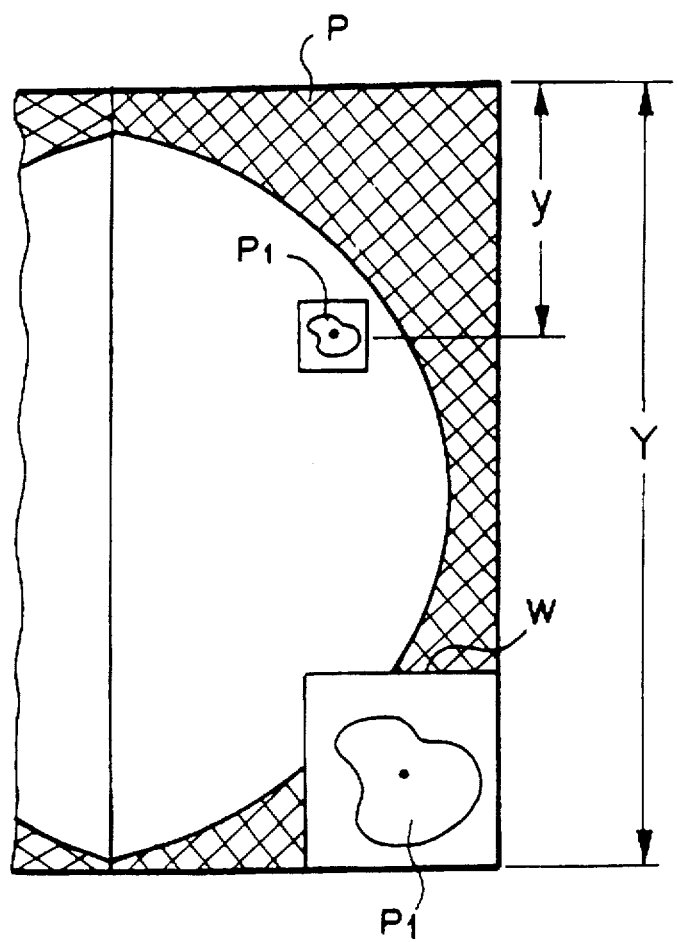
FIG. 15 is an explanatory view showing how a window region W is set on the display surface of an entire area image displaying means.

FIG. 15 is an explanatory view showing how the window region W is set on the display surface of the entire area image displaying means 30, on which the entire area images of the right and left mammae of a single patient are displayed simultaneously such that the back sides of the two images may stand facing each other as shown in FIG. 14B. In FIG. 15, only the right half of the display surface is shown.

In the entire area image displaying means 30 shown in FIG. 15, the vertical length of the display surface is represented by Y, the distance of the detected prospective abnormal pattern $P_1$ from the top end of the entire area image P displayed on the display surface is represented by y, and the position of the window region W is set at the position described below by a display control means (not shown).

Specifically, in cases where y<Y/2, the window region W is located on the side lower than the middle portion of the display surface with respect to the vertical direction. In cases where y>Y/2, the window region W is located on the side higher than the middle portion of the display surface with respect to the vertical direction.

In this manner, the window region W is located on the lower side in cases where the prospective abnormal pattern $P_1$ is present on the upper side. Therefore, the prospective abnormal pattern $P_1$ contained in the entire area image P is not obstructed by the window region W. Accordingly, while the position of the prospective abnormal pattern $P_1$ in the entire area image P is being confirmed, the processed image of the prospective abnormal pattern $P_1$ having been obtained from the image processing, which image has good image quality and can serve as an effective tool in, particularly, the efficient and accurate diagnosis of an illness, can be displayed and viewed in the window region W. As a result, the efficiency and the accuracy of the diagnosis, or the like, can be kept high. In cases where the prospective abnormal pattern $P_1$ is present on the lower side, the window region W is located on the upper side, and therefore the same effects as those described above can be obtained.

Figure 16A:
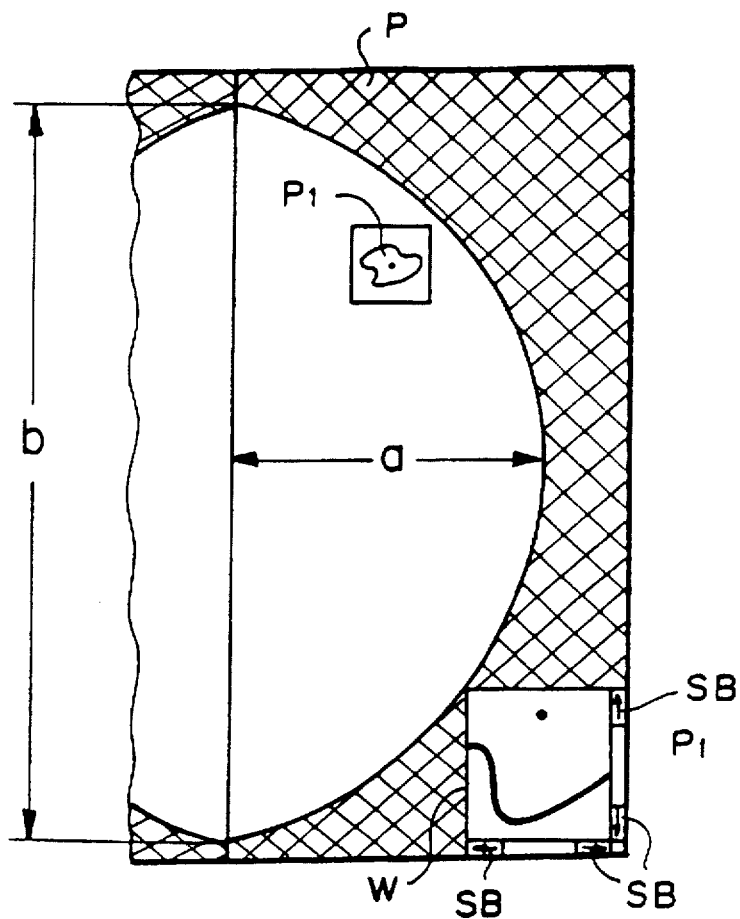
FIG. 16A is an explanatory view showing how a window region is provided with scroll bars.

FIG. 16A shows an example, wherein the window region W does not obstruct the prospective abnormal pattern $P_1$ and the image of the object.

Specifically, in the entire area image displaying means shown in FIG. 16A, the window region W is set by the display control means (not shown) such that it may be located at a position other than the image of the object (in this case, the mamma) in the entire area image P (for example, at the background region).

Such setting is carried out by the display control means (not shown), which calculates the shape and location of the region other than the object image in accordance with the sizes a, b of the region occupied by the object image on the display surface. Therefore, the position and the size of the window region W are changed in accordance with the region occupied by the object image.

It will often occur that the local area limited image to be displayed in the window region W has been enlarged to a desired size by the local area limited image emphasizing means 70, and the prospective abnormal pattern $P_1$ cannot be completely accommodated within the window region W. In such cases, the size of the window region W is varied in accordance with the region occupied by the object image. Also, scroll bars SB, SB, . . . corresponding to the vertical and horizontal directions are provided at the side end and the bottom end of the window region W. The scroll bars SB, SB, . . . are operated, for example, clicked with a mouse device for display surface operation, such that the local area limited image to be displayed in the window region W can be moved within the window region W. In this manner, different portions of the local area limited image can be successively viewed within the window region W.

Figure 16B:
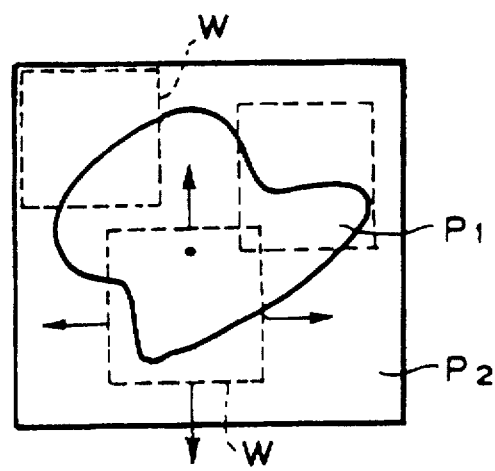
FIG. 16B is an explanatory view showing how a window is moved.

Specifically, as illustrated in FIG. 16B, a window w, which is indicated by the broken line, may be moved with respect to the local area limited image $P_2$, which is to be displayed in the window region W. In this manner, the image in the window w may be displayed in the window region W. These operations may be controlled by the aforesaid display control means.

Figure 17A:
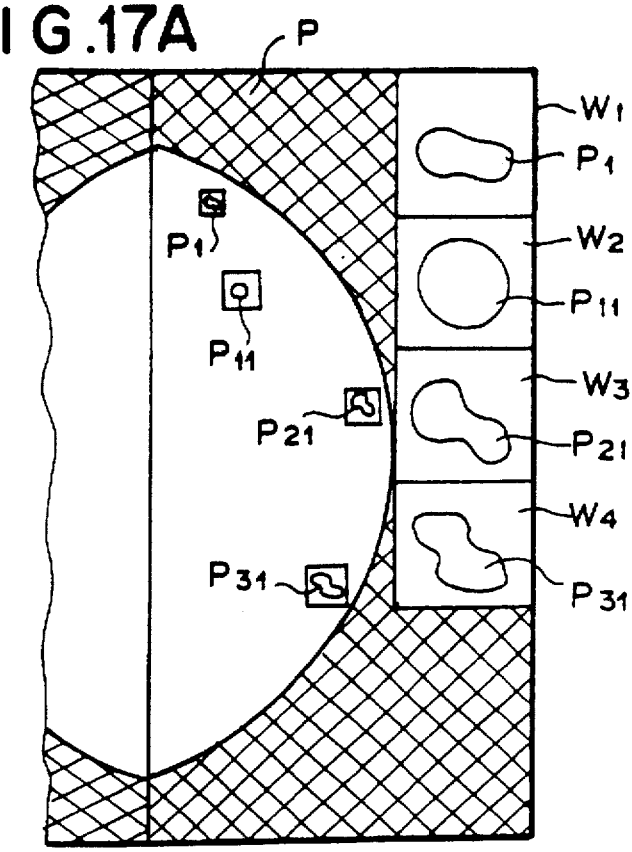
FIG. 17A is an explanatory view showing how a plurality of window regions are displayed with the same size regardless of the sizes of local area limited images.
Figure 17B:
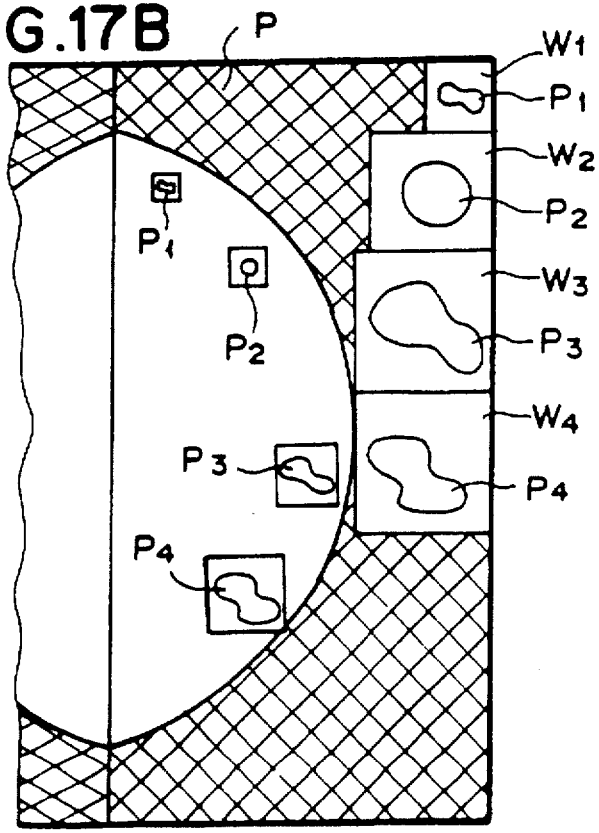
FIG. 17B is an explanatory view showing how a plurality of window regions are displayed with the sizes changed in accordance with the sizes of local area limited images.
Figures 18, 19:
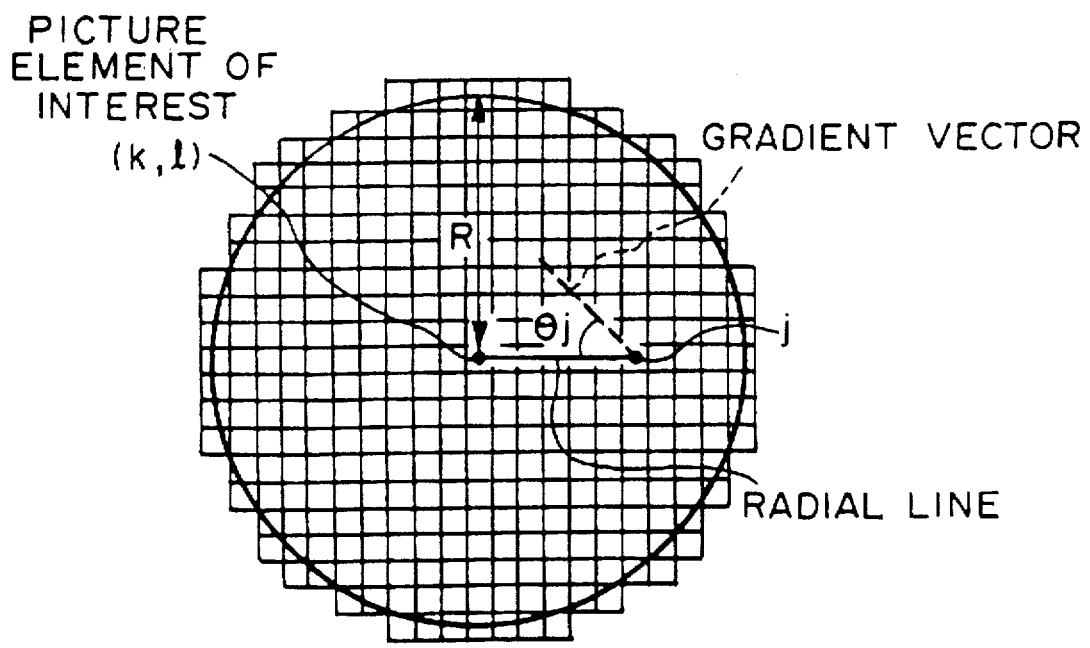
FIG. 18 is an explanatory view showing a mask, which has a size of 5×5 picture elements and is used for calculating directions $\theta$ of gradient vectors in an iris filter.
FIG. 19 is an explanatory view showing the concept behind the degree of centralization of a gradient vector with respect to a picture element of interest.
Figure 21A:
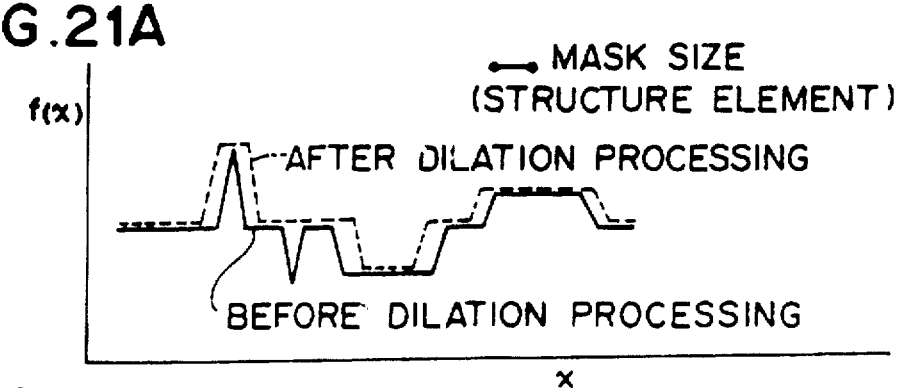
FIG. 21A is a graph showing how a dilation processing, which is one of fundamental operations with a morphology filter, is carried out.
Figure 21B:
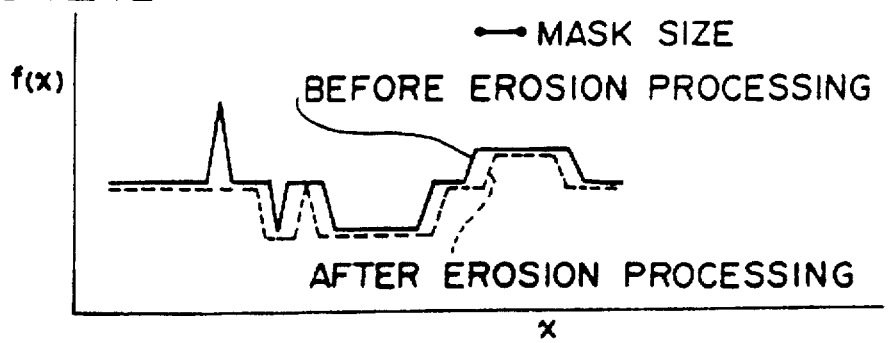
FIG. 21B is a graph showing how an erosion processing, which is one of fundamental operations with a morphology filter, is carried out.
Figure 21C:
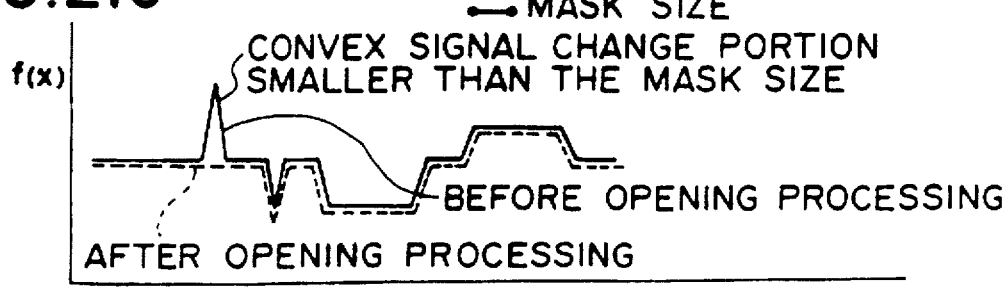
FIG. 21C is a graph showing how an opening processing, which is one of fundamental operations with a morphology filter, is carried out.
Figure 21D:
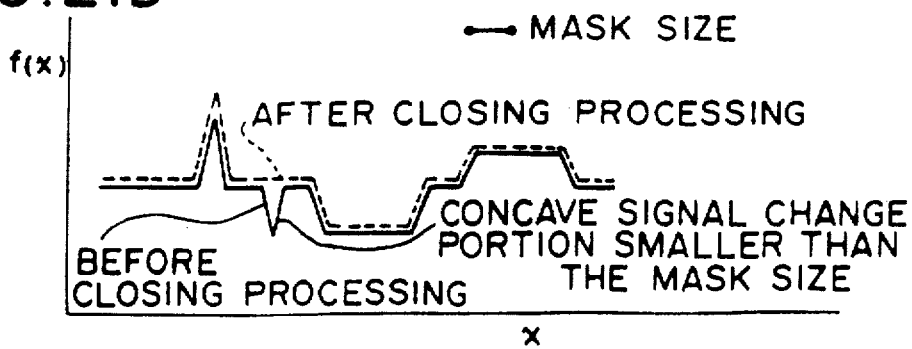
FIG. 21D is a graph showing how a closing processing, which is one of fundamental operations with a morphology filter, is carried out.
Figure 20:
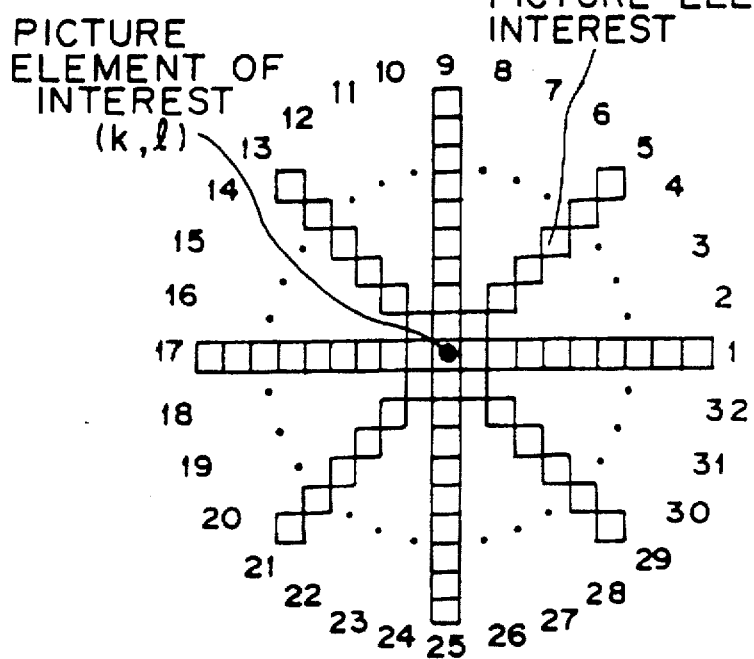
FIG. 20 is an explanatory view showing the picture elements, which are located along a plurality of (in this case, 32) radial lines extending radially from a picture element of interest and for which the degree of centralization of a gradient vector is rated.
Figure 22:
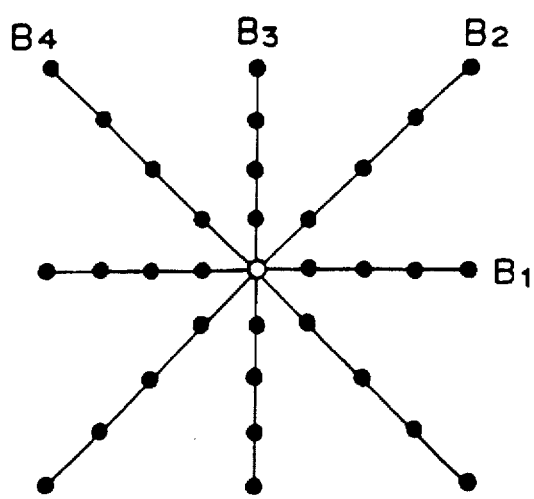
FIG. 22 is an explanatory view showing four linear structure elements employed in a morphology filter.

FIGS. 17A and 17B show how a plurality of local area limited images, which correspond to a plurality of prospective abnormal patterns $P_1$, $P_{11}$, $P_{21}$, and $P_{31}$ having been detected in an object image, are independently displayed in a plurality of window regions $W_1$, $W_2$, $W_3$, and $W_4$.

FIG. 17A is an explanatory view showing how the window regions $W_1$, $W_2$, $W_3$, and $W_4$ are displayed with the same size regardless of the sizes of local area limited images. FIG. 17B is an explanatory view showing how the window regions $W_1$, $W_2$, $W_3$, and $W_4$ are displayed with the sizes changed in accordance with the sizes of local area limited images.

In the example shown in FIG. 17A, in cases where the sizes of the prospective abnormal patterns $P_1$, $P_{11}$, $P_{21}$, and $P_{31}$, which are to be displayed respectively in the window regions $W_1$, $W_2$, $W_3$, and $W_4$, have been set previously by the local area limited image emphasizing means 70, the prospective abnormal patterns may be displayed with the set sizes. In such cases, if the sizes of the prospective abnormal patterns $P_1$, $P_{11}$, $P_{21}$, and $P_{31}$ become larger than the window regions $W_1$, $W_2$, $W_3$, and $W_4$, the scroll bars SB, SB, . . . shown in FIG. 16A may be set for each of the window regions $W_1$, $W_2$, $W_3$, and $W_4$.

Also, in the example illustrated in FIG. 17B, in which the sizes of the window regions $W_1$, $W_2$, $W_3$, and $W_4$ are changed in accordance with the sizes of the local area limited images, in cases where the object image becomes obstructed by the window regions $W_1$, $W_2$, $W_3$, and $W_4$, the sizes of the window regions $W_1$, $W_2$, $W_3$, and $W_4$ may be forcibly reduced as in the example shown in FIG. 16A. In such cases, the sizes of the prospective abnormal patterns $P_1$, $P_{11}$, $P_{21}$, and $P_{31}$, which are displayed in the window regions $W_1$, $W_2$, $W_3$, and $W_4$, may be reduced in accordance with the scales of reduction of the sizes of the window regions $W_1$, $W_2$, $W_3$ and $W_4$. Alternatively, the sizes of the prospective abnormal patterns $P_1$, $P_{11}$, $P_{21}$, and $P_{31}$ may not be reduced, and the scroll bars SB, SB, . . . may be provided.

Figure 23:
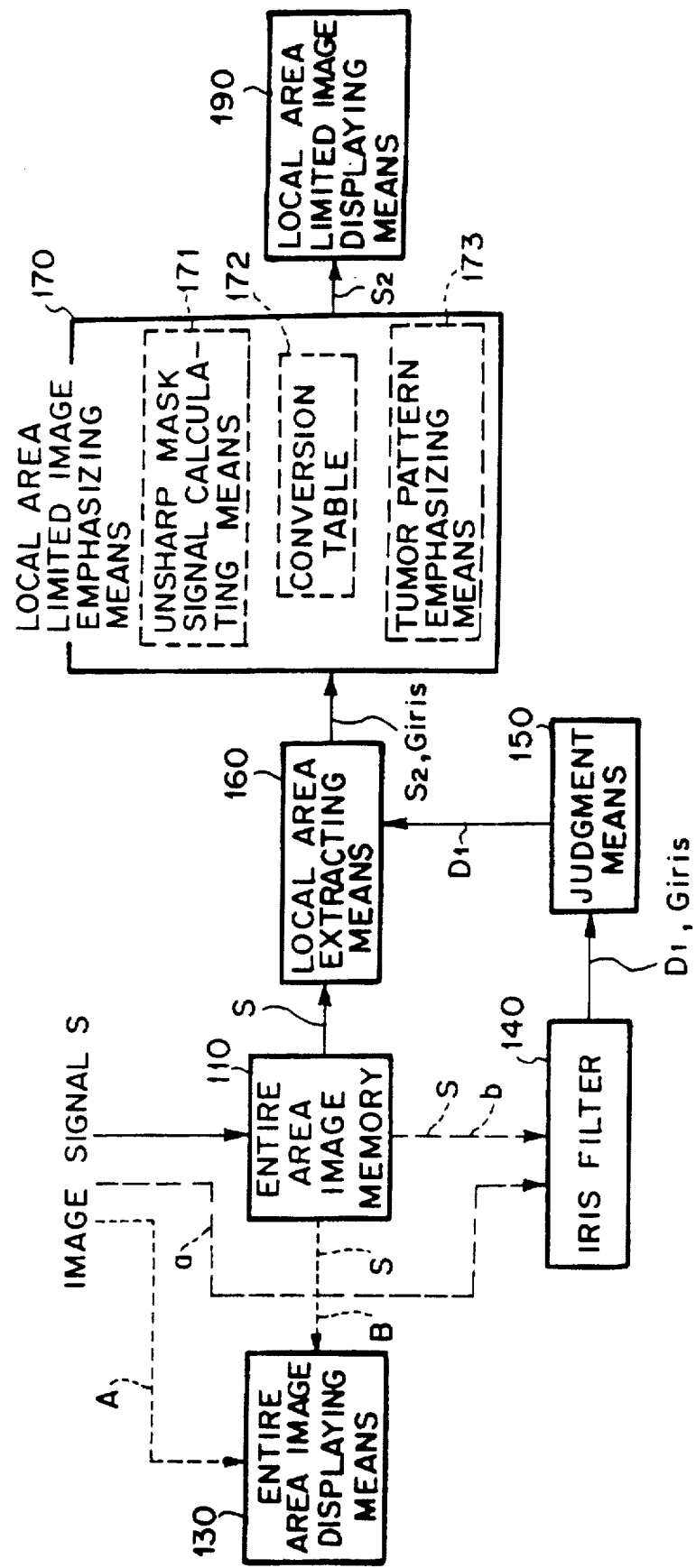
FIG. 23 is a block diagram showing a fifth embodiment of the apparatus for computer aided diagnosis of images in accordance with the present invention.
Figure 24A:
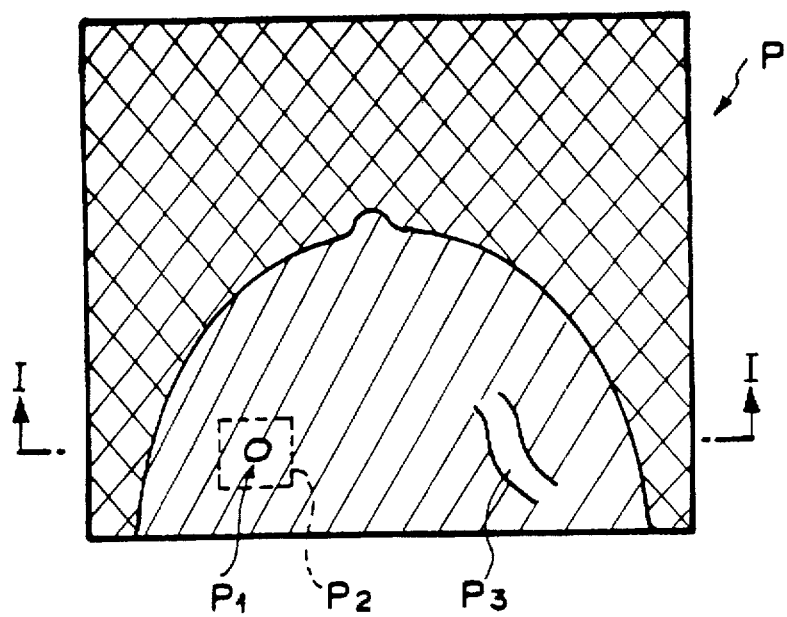
FIG. 24A is an explanatory view showing a radiation image of the mamma (i.e., a mammogram), which is subjected to diagnosis with the embodiment of FIG. 23.

FIG. 23 is a block diagram showing a fifth embodiment of the apparatus for computer aided diagnosis of images in accordance with the present invention. FIG. 24A is an explanatory view showing a radiation image of the mamma (i.e., a mammogram), which is subjected to diagnosis with the embodiment of FIG. 23. The fifth embodiment comprises an entire area image memory 110 for storing an image signal (i.e. an entire area image signal) S, which represents an entire radiation image (i.e., an entire area image) P of a mammogram and which is constituted of a set of density values Dorg corresponding to picture elements of the entire area image P, and an entire area image displaying means 130, which may be constituted of a CRT display device, or the like, and which displays the entire area image P in accordance with the entire area image signal S received directly from the exterior or having been stored in the entire area image memory 110. This embodiment also comprises an iris filter 140 for detecting an abnormal pattern $P_1$ in the entire area image P in accordance with the entire area image signal S, which has been stored in the entire area image memory 110, and a judgment means 150 for making a judgment as to whether the abnormal pattern $P_1$ has been or has not been detected by the iris filter 140. This embodiment further comprises a local area extracting means 160 which, in cases where the judgment means 150 has judged that the abnormal pattern $P_1$ has been detected, extracts an image signal (i.e., a local area limited image signal) $S_2$ representing a local area limited image $P_2$ containing the abnormal pattern $P_1$ from the entire area image signal S having been stored in the entire area image memory 110. This embodiment still further comprises a local area limited image emphasizing means 170 for carrying out image emphasis processing on an image signal representing the abnormal pattern (i.e., an abnormal pattern image signal) $S_1$ such that, of the local area limited image $P_2$ represented by the local area limited image signal $S_2$ having been extracted by the local area extracting means 160, the abnormal pattern $P_1$ may have better image quality and higher capability of serving as an effective tool in, particularly, the efficient and accurate diagnosis of illness than the entire area image P, which is displayed on the entire area image displaying means 130. This embodiment also comprises a local area limited image displaying means 190, which may be constituted of a CRT display device, or the like, and which displays the local area limited image $P_2$ in accordance with the local area limited image signal $S_2$ having been obtained from the image emphasis processing.

The term "abnormal pattern" as used in the fifth embodiment means a tumor pattern.

Also, the iris filter 140 feeds out the information representing the degree of centralization C, which has been calculated with Formula (14) with respect to the picture element corresponding to the tumor pattern, as an iris filter signal Giris representing whether the picture element is or is not the one constituting the tumor pattern.

The image to be processed with the fifth embodiment is not limited to the medical image and may be an image for inspection of an industrial product, or the like. For example, as for X-ray images of castings having a blow-hole therein, the abnormal pattern may be the pattern of the blow-hole.

Also, the term "local area" as used in the fifth embodiment means the region, which is located in the vicinity of the tumor pattern taken as the abnormal pattern and contains the tumor pattern.

In the fifth embodiment, the image signal value representing each of the picture element constituting the image is represented by a density signal value Dorg. Also, the image signal, which represents the region constituted of the set of the picture elements, is represented by the image signal S. The density value Dorg is the high density-high signal level type of signal value. Further, in this embodiment, the tumor pattern has the characteristics such that the density value Dorg may become smaller towards the center point of the pattern.

The processing with the iris filter 140 is carried out with the detection processing algorithm for detecting a specific image portion in accordance with Step 1 to Step 3 described above. However, the term "iris filter" as used in this embodiment does not indicate the algorithm itself and indicates the means for carrying out the processing for detecting the tumor pattern with the algorithm.

Figure 25:
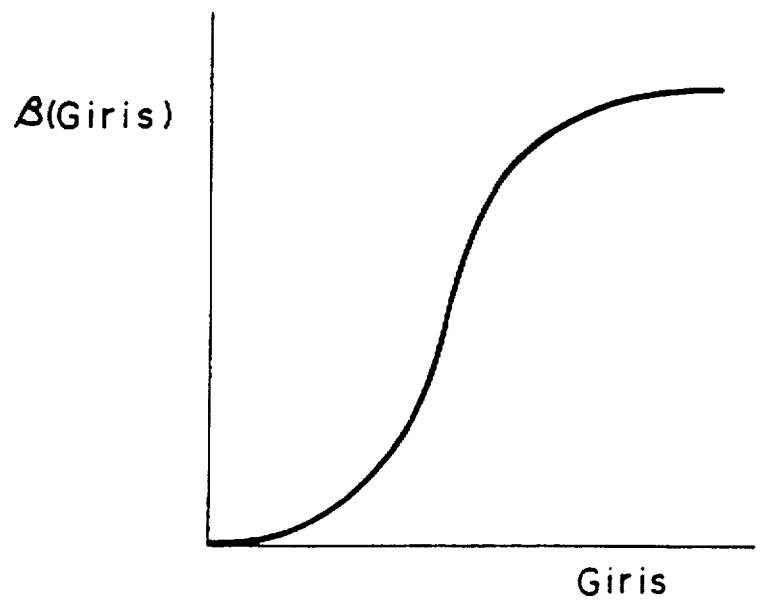

Specifically, the local area limited image emphasizing means 170 comprises an unsharp mask signal calculating means 171 for carrying out an operation on each picture element value (the density value Dorg), which constitutes the local area limited image signal $S_1$, in order to calculate an unsharp mask signal Dus with respect to an unsharp mask constituted of a picture element matrix, which has a size of N columns×N rows (wherein N represents an odd number, for example, 5) and has its center at the picture element, the unsharp mask signal Dus being calculated with Formula (2)

$$Dus = (\Sigma Dorg)/N^2 \qquad (2)$$

wherein ΣDorg represents the sum of the image signal values representing the picture elements located within the unsharp mask. The local area limited image emphasizing means 170 also comprises a conversion table 172 for converting the iris filter signal Giris, which has been obtained with respect to the picture element representing the tumor pattern extracted by the iris filter 140, into an emphasis coefficient β(Giris), which increases monotonously and is shown in FIG. 25. The local area limited image emphasizing means 170 further comprises a tumor pattern emphasizing means 173 for carrying out a frequency emphasis processing with Formula (3)

$$Dproc = Dorg + \beta(Giris) \cdot (Dorg - Dus) \qquad (3)$$

on the density value Dorg, which is the original image signal, by using the unsharp mask signal Dus and the emphasis coefficient β(Giris).

How the fifth embodiment operates will be described hereinbelow.

The entire area image signal S, which represents the entire area image P of the mamma having the tumor therein and serving as the object, is fed from an external storage medium, such as a magneto-optical disk, an image read-out apparatus, or the like, into the entire area image memory 110. Also, the entire area image signal S is fed directly from the exterior into the entire area image displaying means 130 (along a line A shown in FIG. 23). Alternatively, the entire area image signal S having been stored in the entire area image memory 110 may be fed from the entire area image memory 110 into the entire area image displaying means 130 (along a line B shown in FIG. 23). The entire area image displaying means 130 displays the entire area image P in accordance with the entire area image signal S.

The entire area image signal S having been stored in the entire area image memory 110 is also fed into the iris filter 140. In accordance with the procedure described above, with respect to the received entire area image signal S, the iris filter 140 rates the degree of centralization of the gradient vector with Formula (9) in accordance with the density value Dorg. The iris filter 140 thereby detects the image signal (hereinbelow referred to as the tumor pattern image signal) $S_1$, which represents the tumor pattern $P_1$.

Figure 24B:
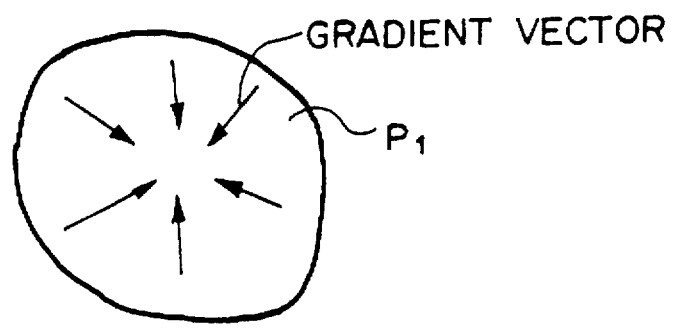
FIG. 24B is an explanatory view showing the degree of centralization of gradient vectors in a tumor pattern.
Figure 24C:
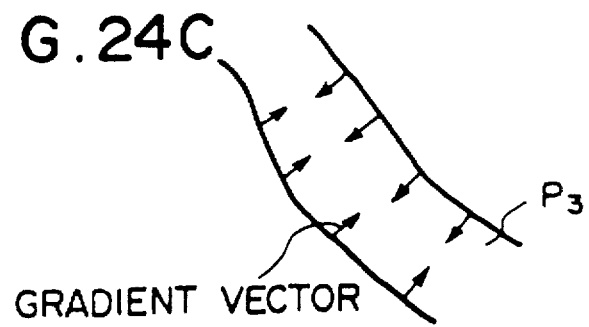
FIG. 24C is an explanatory view showing the degree of centralization of gradient vectors in a blood vessel pattern, or the like, FIG. 25 is a graph showing a function representing a conversion table.

Specifically, the density value Dorg of the tumor pattern $P_1$ in the mammogram, which is shown in FIG. 24A, becomes smaller towards the center point of the pattern. Therefore, as illustrated in FIG. 24B, the direction of the gradient vector represented by Formula (8) centralizes upon the center point of the pattern. On the other hand, as for an image $P_3$ of a blood vessel, the mammary gland, or the like, the density value Dorg becomes smaller towards the center line of the pattern. Therefore, as illustrated in FIG. 24C, the direction of the gradient vector represented by Formula (8) is directed in the same direction and does not centralize upon a single point as in the tumor pattern shown in FIG. 24C.

The iris filter 140 rates the degree of centralization C of the gradient vectors and rates the shape in Step 3 described above. In this manner, the iris filter 140 specifies the picture element (and its position), which corresponds to the image signal $S_1$ representing the tumor pattern $P_1$, and feeds out the information representing the degree of centralization C as the iris filter signal Giris, which represents whether the picture element is or is not the one constituting the tumor pattern. The judgment means 150 judges that the tumor pattern image signal $S_1$ representing the tumor pattern $P_1$ has been detected by the iris filter 140. Also, the judgment means 150 feeds a position signal (hereinbelow referred to as the tumor picture element position signal) $D_1$, which specifies the position of the picture element represented by the tumor pattern image signal $S_1$, and the iris filter signal Giris into the local area extracting means 160.

In cases where it has been judged that the tumor pattern image signal $S_1$ representing the tumor pattern $P_1$ has not been detected by the iris filter 140, the tumor picture element position signal $D_1$, which specifies the position of the picture element represented by the tumor pattern image signal $S_1$, is not fed out, and the processing is finished.

In cases where it has been judged that the tumor pattern image signal $S_1$ has been detected, the entire area image signal S having been stored in the entire area image memory 110 is also fed into the local area extracting means 160. In accordance with the received entire area image signal S and the received tumor picture element position signal $D_1$, the local area extracting means 160 specifies the picture elements (i.e., the local area constituted of the set of these picture elements), which include the picture elements corresponding to the tumor pattern image signal $S_1$ and are located in the vicinity of them, according to a predetermined processing procedure. The local area extracting means 160 thus extracts the local area limited image signal $S_2$, which represents the local area limited image $P_2$, from the entire area image signal S.

The extracted local area limited image signal $S_2$ and the iris filter signal Giris are fed into the local area limited image emphasizing means 170.

With respect to each picture element (the density value Dorg) constituting the local area limited image signal $S_2$ having been fed into the local area limited image emphasizing means 170, the unsharp mask signal calculating means 171 for calculating the super-low frequency component calculates the unsharp mask signal Dus. Thereafter, with the conversion table 172, the iris filter signal Giris having been received from the iris filter 140 is converted into the emphasis coefficient β(Giris). As illustrated in FIG. 25, the conversion table 172 is constituted of the monotonously increasing function. Specifically, the iris filter signal Giris represents the degree of centralization C, and a large value of the degree of centralization C represents that the picture element is the one corresponding to the tumor pattern. Therefore, when the picture element is the one corresponding to the tumor pattern, a large value of the emphasis coefficient β(Giris) is fed out from the conversion table 172.

The tumor pattern emphasizing means 173 calculates the comparatively high frequency component (Dorg-Dus), which is the difference signal between the original image signal Dorg and the unsharp mask signal Dus having been calculated by the unsharp mask signal calculating means 171. Also, the tumor pattern emphasizing means 173 calculates the product β(Giris)·(Dorg-Dus) of the emphasis coefficient β(Giris), which has been obtained from the conversion table 172, and the comparatively high frequency component (Dorg-Dus). The tumor pattern emphasizing means 173 then adds the density value Dorg of the original image to the product and feeds out the signal Dproc, which results from the frequency emphasis processing carried out with Formula (3).

With the frequency emphasis processing, the comparatively high frequency component (Dorg-Dus) is emphasized with the emphasis coefficient β(Giris) obtained in accordance with the iris filter signal Giris, which is obtained from the iris filter 140 and indicates whether the picture element is or is not the one constituting the tumor pattern. Therefore, even if an unnecessary component, such as quantum noise, is contained in the high frequency component (Dorg-Dus), in cases where the picture element is not the one constituting the image portion, such as the tumor pattern, (for example, in cases where the picture element is the one constituting the blood vessel pattern, or the like), the value of β(Giris) with respect to the picture element will be small, and the degree of emphasis with respect to the picture element will be kept low. In cases where the picture element is the one constituting the image portion, such as the tumor pattern, the value of β(Giris) with respect to the picture element is large, and therefore the degree of emphasis with respect to the picture element is kept high.

Therefore, regardless of whether radiation noise is or is not contained in the high frequency component (Dorg-Dus) of the image, the tumor pattern can be selectively emphasized with the function β(Giris), which has a value in accordance with whether the image area is or is not the tumor pattern.

The local area limited image displaying means 190 displays an image, in which the tumor pattern $P_1$ in the local area limited image $P_2$ has been emphasized by the local area limited image emphasizing means 170.

In this manner, of the entire area image P, only the local area limited image $P_2$ containing the tumor pattern $P_1$ is independently displayed on the local area limited image displaying means 190. Therefore, the person, who views the radiation image, can concentrate his attention on the local area limited image $P_2$, which is displayed on the local area limited image displaying means 190. As a result, the efficiency and the accuracy of the diagnosis, or the like, can be kept high.

In this embodiment, the entire area image displaying means 130 may also serve as the local area limited image displaying means 190. In such cases, of the entire area image P displayed, only the tumor pattern $P_1$ is emphasized selectively. Therefore, the efficiency and the accuracy of the diagnosis, or the like, can be kept high.

In lieu of the tumor pattern emphasizing means 173 for carrying out the emphasis processing with Formula (3), the local area limited image emphasizing means 170 may be provided with an abnormal pattern emphasizing means for carrying out the emphasis processing with Formula (1). In such cases, the same effects as those with the aforesaid fifth embodiment can be obtained.

Figure 26:
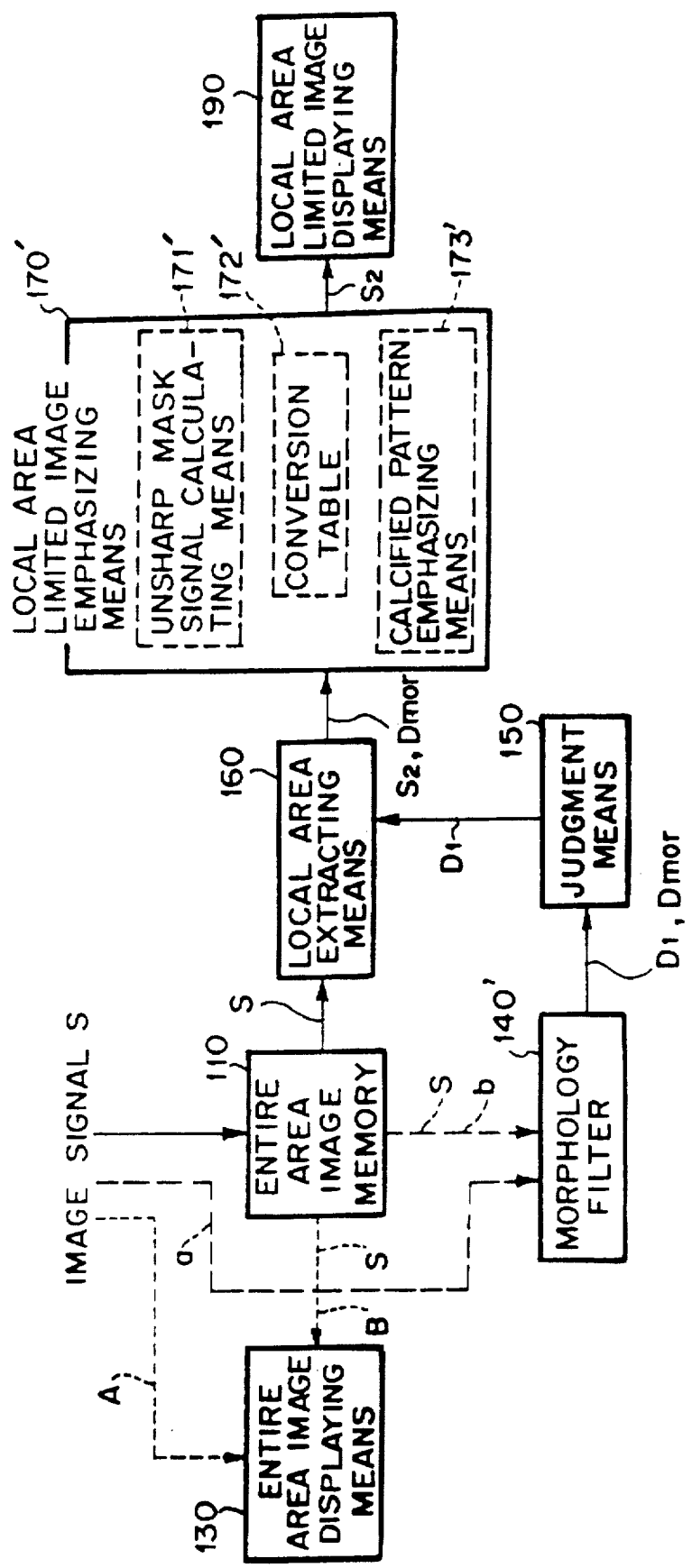
FIG. 26 is a block diagram showing a sixth embodiment of the apparatus for computer aided diagnosis of images in accordance with the present invention.
Figure 27A:
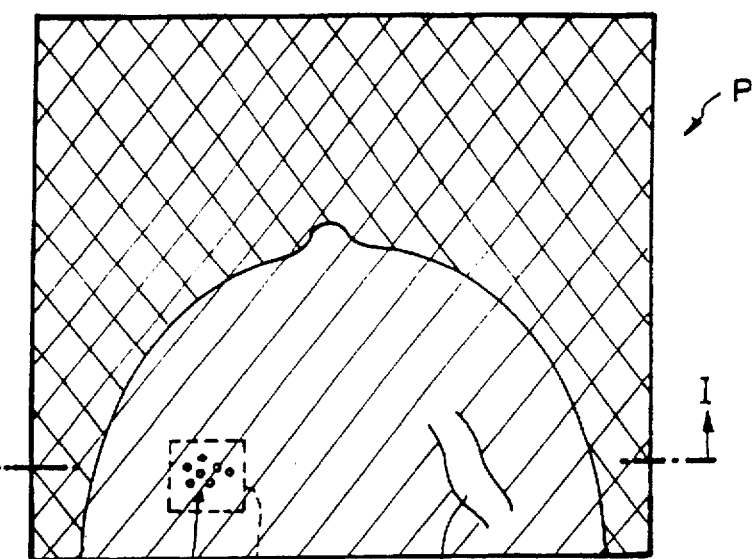
FIG. 27A is an explanatory view showing a radiation image of the mamma (i.e., a mammogram), which is subjected to diagnosis with the embodiment of FIG. 26.
Figure 28A:
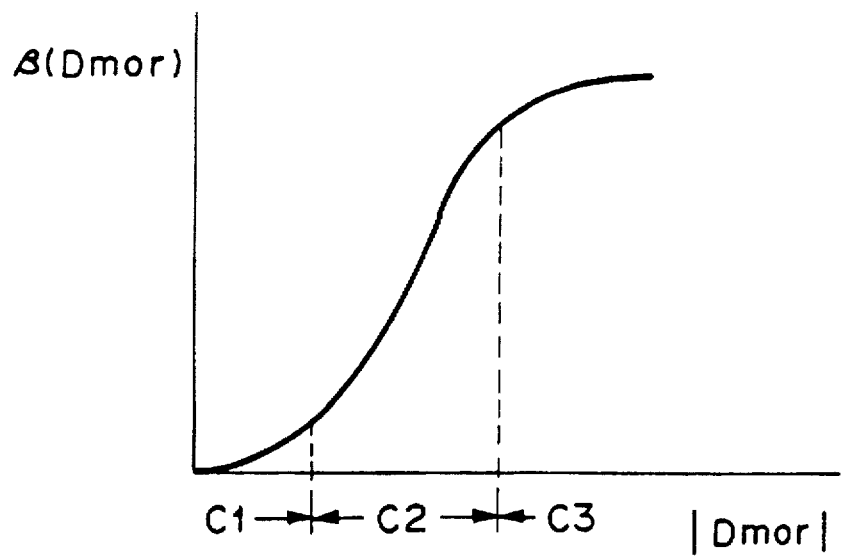
Figure 28B:
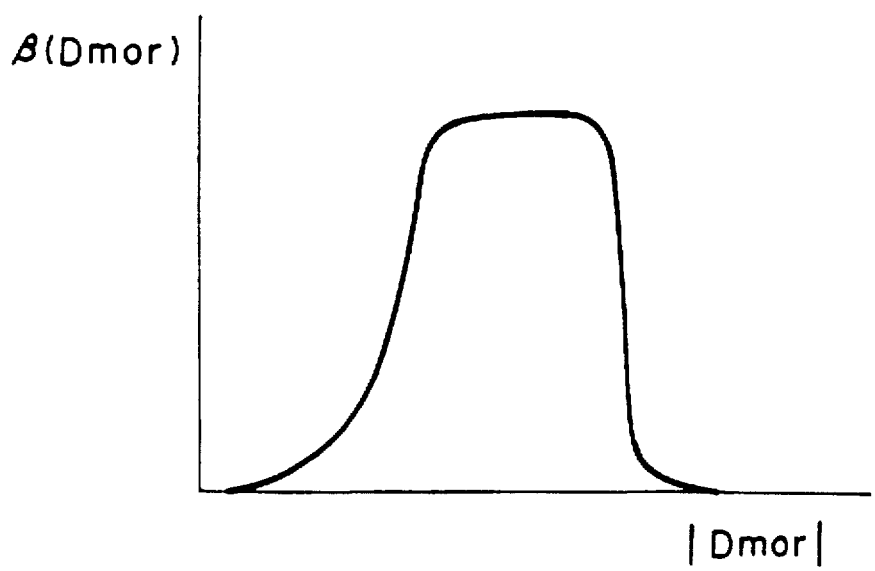
Figure 29:
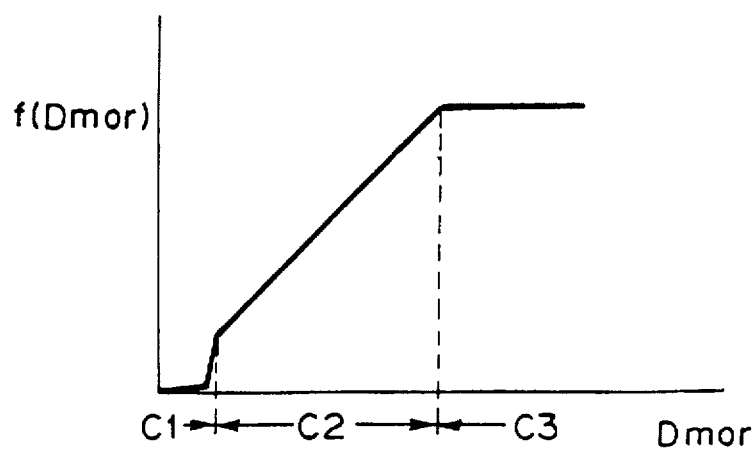
FIG. 29 is a graph showing a function f(Dmor) in accordance with a morphology signal Dmor.
Figure 30A:
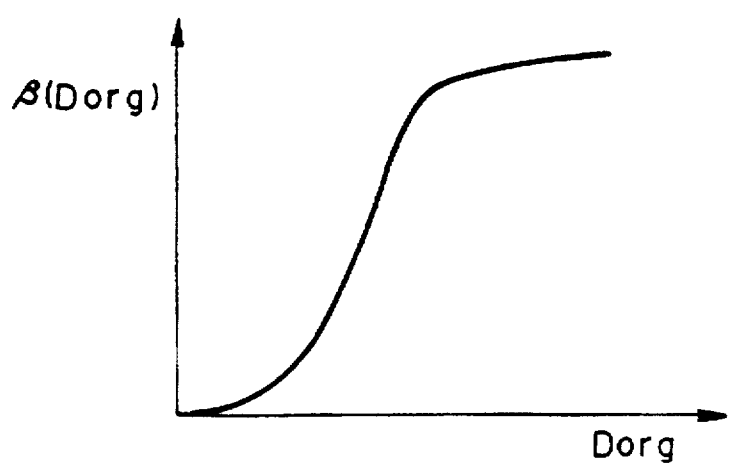
FIGS. 30A and 30B are graphs showing emphasis functions β(Dorg) in accordance with an original image signal Dorg.
Figure 30B:
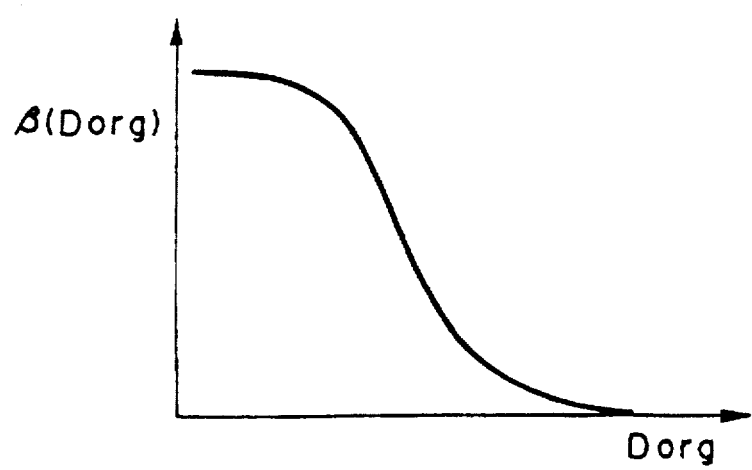
Figure 31:
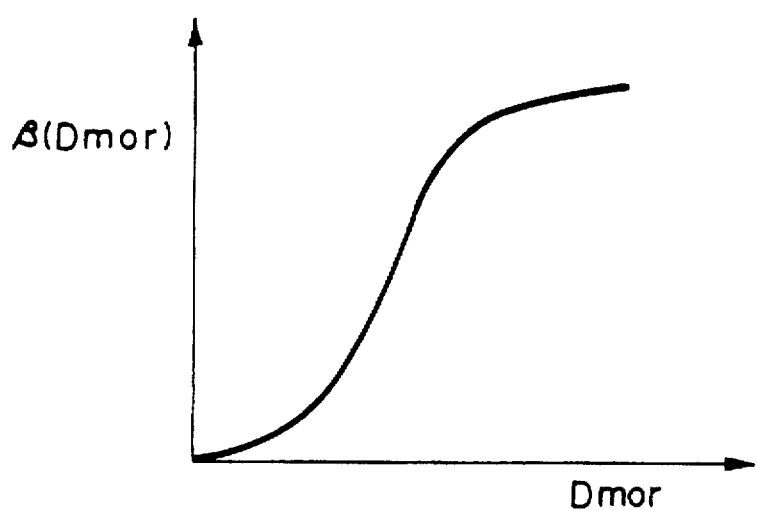
FIG. 31 is a graph showing an emphasis function β(Dmor) in accordance with a morphology signal Dmor.
Figure 33:
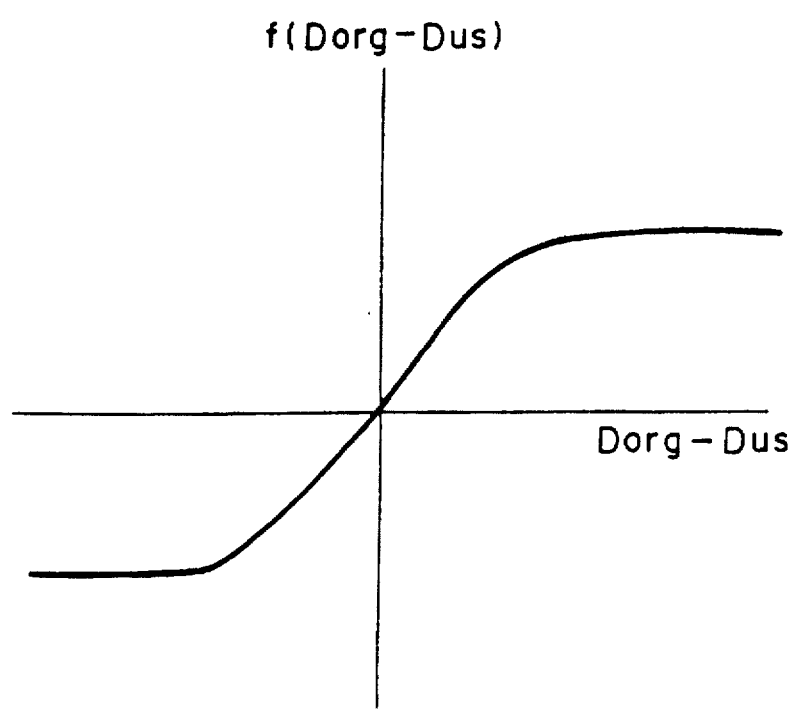
FIG. 33 is a graph showing a function f(Dorg-Dus), which restricts overshooting and undershooting.
Figure 32:
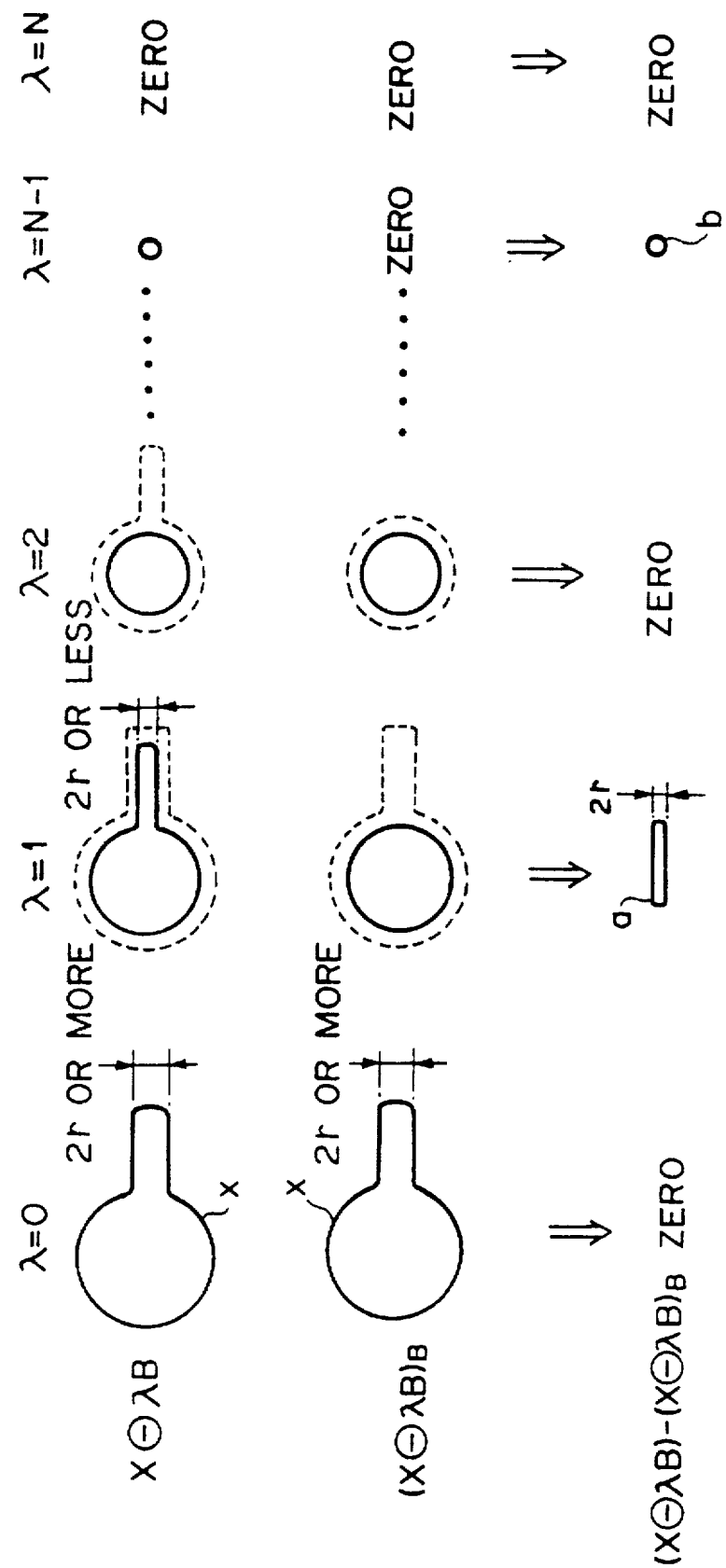
FIG. 32 is an explanatory view showing how a skeleton processing is carried out.

FIG. 26 is a block diagram showing a sixth embodiment of the apparatus for computer aided diagnosis of images in accordance with the present invention. FIG. 27A is an explanatory view showing a radiation image of the mamma (i.e., a mammogram), which is subjected to diagnosis with the embodiment of FIG. 26. The sixth embodiment is the same as the fifth embodiment, except that a morphology filter 140' is provided in lieu of the iris filter 140, a conversion table 172' is provided in lieu of the conversion table 172, and a calcified pattern emphasizing means 173' for carrying out frequency emphasis processing with Formula (7) is provided in lieu of the tumor pattern emphasizing means 173. The conversion table 172' is used to convert a morphology signal Dmor, which has been obtained with respect to a picture element constituting the small calcified pattern having been extracted by the morphology filter 140', into an emphasis coefficient β(Dmor), which increases monotonously and is shown in FIG. 28A.

The term "abnormal pattern" as used in the sixth embodiment means a small calcified pattern.

The processing with the morphology filter 140' is carried out with the detection processing algorithm for detecting a calcified pattern. However, the term "morphology filter" as used in this embodiment does not indicate the algorithm itself and indicates the means for carrying out the processing for detecting the calcified pattern with the algorithm, i.e., the morphology processing with Formula (28).

How the sixth embodiment operates will be described hereinbelow.

The entire area image signal S, which represents the entire area image P of the mamma having the calcified portion therein and serving as the object, is fed from an external storage medium, such as a magneto-optical disk, an image read-out apparatus, or the like, into the entire area image memory 110. Also, the entire area image signal S is fed directly from the exterior into the entire area image displaying means 130 (along a line A shown in FIG. 26). Alternatively, the entire area image signal S having been stored in the entire area image memory 110 may be fed from the entire area image memory 110 into the entire area image displaying means 130 (along a line B shown in FIG. 26). The entire area image displaying means 130 displays the entire area image P in accordance with the entire area image signal S.

The entire area image signal S having been stored in the entire area image memory 110 is also fed into the morphology filter 140'. With Formula (28), the morphology filter 140' detects the image signal (hereinbelow referred to as the calcified pattern image signal) $S_1$, which represents a calcified pattern $P_1$.

Figure 27B:
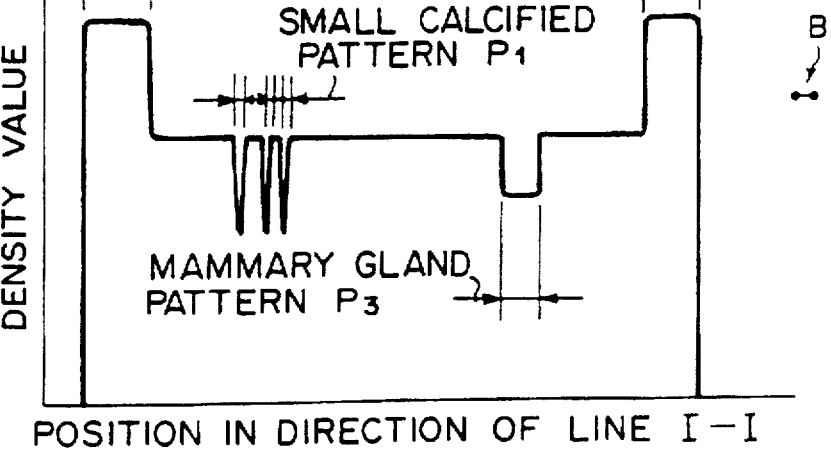
FIG. 27B is a graph showing the distribution of density values of the mammogram in the cross section taken along line I—I of FIG. 27A.

Specifically, density values Dorg of the mammogram in the cross section taken along line I—I of FIG. 27A are distributed in the pattern shown in FIG. 27B. At the small calcified pattern $P_1$, the density value fluctuates in a spatially narrower range than a structure element B and is smaller than the density values of the surrounding image areas. Therefore, the morphology signal Dmor, which is calculated with Formula (28), takes a predetermined value other than zero, and the pattern is smoothed by the closing processing. On the other hand, at a pattern $P_3$ of the blood vessel or the mammary gland, at which the density value fluctuates in a spatially wider range than the structure element B, the value of the morphology signal Dmor becomes equal to zero. Therefore, the pattern is not smoothed by the closing operation.

In this manner, the morphology filter 140' specifies the picture element (and its position), which corresponds to the image signal $S_1$ representing the small calcified pattern $P_1$. The judgment means 150 judges that the calcified oattern image signal $S_1$ representing the small calcified pattern $P_1$ has been detected by the morphology filter 140'. Also, the judgment means 150 feeds a position signal (hereinbelow referred to as the calcified picture element position signal) $D_1$, which specifies the position of the picture element represented by the calcified pattern image signal $S_1$, and the morphology signal Dmor, which represents the fluctuation of the density value of the small calcified pattern $P_1$ having been extracted by the morphology filter 140', into the local area extracting means 160.

In cases where it has been judged that the calcified pattern image signal $S_1$ representing the small calcified pattern $P_1$ has not been detected by the morphology filter 140', the calcified picture element position signal $D_1$, which specifies the position of the picture element represented by the calcified pattern image signal $S_1$, is not fed out, and the processing is finished.

In cases where it has been judged that the calcified pattern image signal $S_1$ has been detected, the entire area image signal S having been stored in the entire area image memory 110 is also fed into the local area extracting means 160. In accordance with the received entire area image signal S and the received calcified picture element position signal $D_1$, the local area extracting means 160 specifies the picture elements (i.e., the local area constituted of the set of these picture elements), which include the picture elements corresponding to the calcified pattern image signal $S_1$ and are located in the vicinity of them, according to a predetermined processing procedure. The local area extracting means 160 thus extracts the local area limited image signal $S_1$, which represents the local area limited image $P_2$, from the entire area image signal S.

The extracted local area limited image signal $S_1$ and the morphology signal Dmor are fed into a local area limited image emphasizing means 170'.

With respect to each picture element (the density value Dorg) constituting the local area limited image signal $S_2$ having been fed into the local area limited image emphasizing means 170', an unsharp mask signal calculating means 171' for calculating the super-low frequency component calculates the unsharp mask signal Dus. Thereafter, with the conversion table 172', the morphology signal Dmor having been received from the morphology filter 140' is converted into the emphasis coefficient β(Dmor). As illustrated in FIG. 28A, the conversion table 172' is constituted of the monotonously increasing function. Specifically, a large value of the morphology signal Dmor represents that the picture element is the one corresponding to the calcified pattern. Therefore, when the picture element is the one corresponding to the calcified pattern, a large value of the emphasis coefficient β(Dmor) is fed out from the conversion table 172'.

Figure 27C:
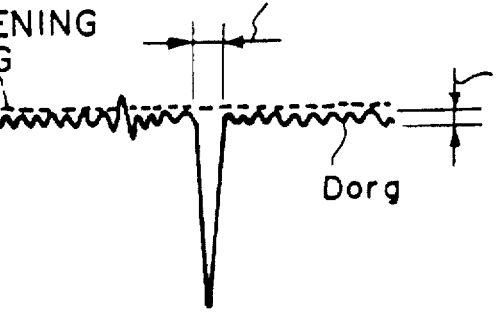
FIG. 27C is an enlarged view showing a portion of the distribution shown in FIG. 27B, FIGS. 28A and 28B are graphs showing a function representing a conversion table.

With the conversion table 172', the emphasis coefficient β(Dmor) is restricted to a very small value with respect to a region C1, in which the value of the morphology signal Dmor is very small. Therefore, as for the region C1, little image emphasis is carried out, and the processed image signal Dproc is close to the original image signal Dorg. Specifically, actually, as illustrated in FIG. 27C, radiation noise has been superposed upon the distribution curve of the density value shown in FIG. 27B. However, as indicated by the broken line in FIG. 27C, the radiation noise is smoothed by the closing operation of the second term in Formula (28). Therefore, the value of Dmor is fluctuated very finely. However, the amount of the fluctuation is smaller than the fluctuation Dmor due to the small calcified pattern $P_1$. Accordingly, by appropriate setting of the value of the boundary between the regions C1 and C2, it is possible to prevent the high-frequency noise from being emphasized.

In the region C3, the change in the emphasis coefficient β(Dmor) is restricted with respect to the change in the value of Dmor. The restriction is done in order to prevent the image portion, which already has a certain level of contrast, from being emphasized excessively. If the excessive emphasis is carried out, the contrast of the image areas other than the image portion will become comparatively low, and therefore the image quality of the image and its capability of serving as an effective tool in the efficient and accurately diagnosis of an illness will become low.

The calcified pattern emphasizing means 173' carries out the frequency emphasis processing with Formula (28) in accordance with the emphasis coefficient β(Dmor) obtained from the conversion table 172' and the unsharp mask signal Dus having been calculated by the unsharp mask signal calculating means 171'.

With the frequency emphasis processing, the comparatively high frequency component (Dorg-Dus) is emphasized with the emphasis coefficient β(Dmor) obtained in accordance with the morphology signal Dmor, which is obtained from the morphology filter 140' and indicates whether the picture element is or is not the one constituting the calcified pattern. Therefore, even if an unnecessary component, such as quantum noise, is contained in the high frequency component (Dorg-Dus), in cases where the picture element is not the one constituting the image portion, such as the calcified pattern, (for example, in cases where the picture element is the one constituting the blood vessel pattern, or the like), the value of β(Dmor) with respect to the picture element will be small, and the degree of emphasis with respect to the picture element will be kept low. in cases where the picture element is the one constituting the image portion, such as the calcified pattern, the value of β(Dmor) with respect to the picture element is large, and therefore the degree of emphasis with respect to the picture element is kept high.

Therefore, regardless of whether radiation noise is or is not contained in the high frequency component (Dorg-Dus) of the image, the specific image portion, such as the calcified pattern, can be selectively emphasized with the function β(Dmor), which has a value in accordance with whether the image area is or is not the specific image portion.

The local area limited image displaying means 190 displays an image, in which the small calcified pattern $P_1$ in the local area limited image $P_2$ has been emphasized by the local area limited image emphasizing means 170'.

In this manner, of the entire area image P, only the local area limited image $P_2$ containing the small calcified pattern $P_1$ is independently displayed on the local area limited image displaying means 190. Therefore, the person, who views the radiation image, can concentrate his attention on the local area limited image $P_2$, which is displayed on the local area limited image displaying means 190. As a result, the efficiency and the accuracy of the diagnosis, or the like, can be kept high.

In this embodiment, the entire area image displaying means 130 may also serve as the local area limited image displaying means 190. In such cases, of the entire area image P displayed, only the small calcified pattern $P_1$ is emphasized selectively. Therefore, overshooting and undershooting can be restricted, an artifact due to them can be reduced, and a reproduced image can be obtained, which has good image quality and can serve as an effective tool in the efficient and accurate diagnosis of an illness.

In this embodiment, the morphology filter 140' carries out the morphology operation with Formula (28). Alternatively, the emphasis processing may be carried out with the morphology operation in accordance with one of Formula (27) and Formulas (29) through (33).

With the processing for detecting the small calcified pattern alone, which is carried out by the morphology filter 140' in accordance with one of morphology operation Formulas (27) through (33), it will often occur that a pattern resembling the small calcified pattern is also detected as a calcified pattern. Specifically, an image (hereinbelow referred to as the non-calcified pattern) will often be detected, which is other than the calcified pattern and has approximately the same size as the calcified pattern and for which the value of Dmor calculated with Formulas (27) through (33) does not become equal to zero. If the emphasis processing is carried out on such a non-calcified pattern, an accurate diagnosis cannot be made.

Therefore, such that the non-calcified pattern may be prevented from being detected together with the calcified pattern and only the calcified pattern can be detected accurately, the morphology filter 140' may be provided with the discriminating function described below.

Specifically, the differential operation based upon the morphology operation is carried out with Formula (34) shown below. A larger value of Mgrad represents a higher possibility that the picture element will be the one constituting the calcified pattern. Therefore, in lieu of Formulas (27) through (33), the logical operation is then carried out with Formula (35).

$$\text{Mgrad} = (\frac{1}{2}) \cdot (\text{Dorg} \oplus \lambda B - \text{Dorg} \ominus B) \tag{34}$$

$$\text{if Dmor}(x,y) \geq T1 \text{ and Mgrad} \geq T2 \text{ then Dmor}(x,y) = \text{Dmor}(x,y) \text{ else Dmor}(x,y) = 0 \tag{35}$$

In cases where the value of Dmor obtained with Formula (35) is equal to zero, the picture element is the one constituting the non-calcified pattern. Therefore, in such cases, the emphasis processing with Formula (7) is not carried out. In cases where the value of Dmor obtained with Formula (35) is not equal to zero, the picture element is the one constituting the calcified pattern. Therefore, in such cases, the emphasis processing with Formula (7) is not carried out. In Formula (35), T1 and T2 represent the threshold values which have been set experimentally.

Besides the discrimination with Formulas (34) and (35), the discrimination between the calcified pattern and the non-calcified pattern may be carried out with the combination of the opening processing and the closing processing with the multi-scale.

Specifically, the value of Dmor may be set with Formulas (36), (37), and (38) shown below.

$$D' = Dmor \ominus \lambda_1 B \oplus \lambda_1 B \quad (36)$$

$$D_c(x,y) = D' \oplus \lambda_2 B \ominus \lambda_2 B \quad (37)$$

$$\text{if } D_c(x,y) \geq T \text{ then } Dmor(x,y) = Dmor(x,y) \text{ else } Dmor(x,y) = 0 \quad (38)$$

In Formula (38), T represents a threshold value having been set experimentally.

In lieu of the calcified pattern emphasizing means 173' for carrying out the emphasis processing with Formula (7), the local area limited image emphasizing means 170' may be provided with an abnormal pattern emphasizing means for carrying out the emphasis processing with one of Formulas (4), (5), and (6). In such cases, the same effects as those with the aforesaid sixth embodiment can be obtained.

What is claimed is:

1. An apparatus for computer aided diagnosis of images, comprising:

i) an entire image storing means for storing an entire area image signal representing a radiation image of an object;

ii) a prospective abnormal pattern detecting means for detecting a prospective abnormal pattern in said radiation image in accordance with said entire area image signal;

iii) a judgment means for making a determination as to the presence or absence of said prospective abnormal pattern in accordance with the results of the detection of said prospective abnormal pattern carried out by said prospective abnormal pattern detecting means;

iv) a local area extracting means for extracting a local area limited image signal corresponding to a local area containing said prospective abnormal pattern from said entire area image signal having been stored in said entire area image storing means, wherein said judgment means has determined that said prospective abnormal pattern is present;

v) a local area limited image displaying means for displaying the image of said local area in accordance with said local area limited image signal, which has been extracted by said local area extracting means;

vi) an entire area image displaying means for displaying the entire area of said radiation image of the object in accordance with said entire area image signal;

vii) local area limited image storing means for temporarily storing said local area limited image signal, said local area limited storing means being located between said local area extracting means and said local area limited image displaying means; and viii) local area limited image display requesting means for causing said local area limited image signal to be fed out from said local area limited image storing means and causing the image of said local area to be displayed on said local area limited image displaying means, when a predetermined image display request is received from the exterior, said local area limited image display requesting means being located between said local area extracting means and said local area limited image displaying means.

2. An apparatus as defined in claim 1 wherein the apparatus further comprises a local area limited image emphasizing means for carrying out image emphasis processing on at least the abnormal pattern image signal, which represents said prospective abnormal pattern and is among said local area limited image signal, such that the image of said prospective abnormal pattern in the image of said local area, which is displayed on said local area limited image displaying means, may have better image quality and higher capability of serving as an effective tool in, particularly, the efficient and accurate diagnosis of an illness than said radiation image, which is displayed on said entire area image displaying means.

3. An apparatus as defined in claim 2 wherein said image emphasis processing carried out by said local area limited image emphasizing means is at least one processing selected from the group consisting of gradation processing, frequency processing, and enlargement processing.

4. An apparatus as defined in claim 3 wherein said gradation processing is set such that the level of contrast of the image of said local area, which is displayed on said local area limited image displaying means, may become higher than the level of contrast of said radiation image, which is displayed on said entire area image displaying means.

5. An apparatus as defined in claim 4 wnerein said gradation processing is set such that the level of contrast of the image of said local area, which is displayed on said local area limited image displaying means, may become at least 1.2 times as high as the level of contrast of said radiation image, which is displayed on said entire area image displaying means.

6. An apparatus as defined in claim 3 wherein said gradation processing is set such that the level of contrast of at least the image of said prospective abnormal pattern in the image of said local area, which is displayed on said local area limited image displaying means, may become higher than the level of contrast of said radiation image, which is displayed on said entire area image displaying means.

7. An apparatus as defined in claim 6 wherein said gradation processing is set such that the level of contrast of at least the image of said prospective abnormal pattern in the image of said local area, which is displayed on said local area limited image displaying means, may become at least 1.2 times as high as the level of contrast of said radiation image, which is displayed on said entire area image displaying means.

8. An apparatus as defined in claim 3 wherein said frequency processing is set such that the degree of emphasis of the image of said local area, which is displayed on said local area limited image displaying means, may become higher than the degree of emphasis of said radiation image, which is displayed on said entire area image displaying means.

9. An apparatus as defined in claim 8 wherein said frequency processing is set such that the degree of emphasis of the image of said local area, which is displayed on said local area limited image displaying means, may become at least 1.1 times as high as the degree of emphasis of said radiation image, which is displayed on said entire area image displaying means.

10. An apparatus as defined in claim 3 wherein said frequency processing is set such that the degree of emphasis of at least the image of said prospective abnormal pattern in the image of said local area, which is displayed on said local area limited image displaying means, may become higher than the degree of emphasis of said radiation image, which is displayed on said entire area image displaying means.

11. An apparatus as defined in claim 10 wherein said frequency processing is set such that the degree of emphasis of at least the image of said prospective abnormal pattern in the image of said local area, which is displayed on said local area limited image displaying means, may become at least 1.1 times as high as the degree of emphasis of said radiation image, which is displayed on said entire area image displaying means.

12. An apparatus as defined in claim 3 wherein said enlargement processing is set such that the display size of the image of said local area, which is displayed on said local area limited image displaying means, or the image of said prospective abnormal pattern in the image of said local area may become larger than the display size of the image of said local area or the image of said prospective abnormal pattern in said radiation image, which is displayed on said entire area image displaying means.

13. An apparatus as defined in claim 12 wherein said enlargement processing is set such that the display size of the image of said local area, which is displayed on said local area limited image displaying means, or the image of said prospective abnormal pattern in the image of said local area may become at least 1.5 times as large as the display size of the image of said local area or the image of said prospective abnormal pattern in said radiation image, which is displayed on said entire area image displaying means.

14. An apparatus as defined in claim 3 wherein said enlargement processing is set such that the scale of enlargement may be changed in accordance with the size of said prospective abnormal pattern detected by said prospective abnormal pattern detecting means.

15. An apparatus as defined in claim 2 wherein the apparatus further comprises an entire area image emphasizing means for carrying out predetermined image emphasis processing on said entire area image signal.

16. An apparatus as defined in claim 15 wherein said predetermined image emphasis processing, which is carried out by said entire area image emphasizing means, is at least one processing selected from the group consisting of gradation processing and frequency processing.

17. An apparatus as defined in claim 1 wherein the processing for detecting said prospective abnormal pattern, which is carried out by said prospective abnormal pattern detecting means, is based upon at least one processing selected from the group consisting of iris filter processing and morphology processing.

18. An apparatus as defined in claim 1 wherein said entire area image displaying means also serves as said local area limited image displaying means, and the image of said local area is displayed at a portion of the display surface of said entire area image displaying means.

19. An apparatus as defined in claim 18 wherein the image of said local area, which is displayed on said entire area image displaying means, is displayed in a display region different from the local area, which is located in said radiation image displayed on said entire area image displaying means and which corresponds to said image of said local area.

20. An apparatus as defined in claim 18 wherein the display region for the image of said local area, which is displayed on said entire area image displaying means, is determined such that it may be accommodated in a display region, which is different from the object image displayed on said entire area image displaying means.

21. An apparatus as defined in claim 20 wherein, in cases where the size of the display region for the image of said local area on said entire area image displaying means is smaller than the size of the image of said local area, only a portion of the image of said local area, which portion is capable of being displayed within the display region for the image of said local area, is displayed, and the image of said local area is scrolled within the display region.

22. An apparatus as defined in claim 18 wherein a plurality of the images of local areas are capable of being displayed on said entire area image displaying means.

23. An apparatus as defined in claim 1 wherein said object is a pair of the right and left mammae, and a pair of the entire area images of the right and left mammae are displayed on said entire area image displaying means.

24. An apparatus as defined in claim 23 wherein the image of said local area, which is displayed on said entire area image displaying means, is displayed in a display region different from the local area, which is located in said radiation image displayed on said entire area image displaying means and which corresponds to said image of said local area.

25. An apparatus as defined in claim 23 wherein the display region for the image of said local area, which is displayed on said entire area image displaying means, is determined such that it may be accommodated in a display region, which is different from the object image displayed on said entire area image displaying means.

26. An apparatus as defined in claim 25 wherein, in cases where the size of the display region for the image of said local area on said entire area image displaying means is smaller than the size of the image of said local area, only a portion of the image of said local area, which portion is capable of being displayed within the display region for the image of said local area, is displayed, and the image of said local area is scrolled within the display region.

27. An apparatus for computer aided diagnosis of images, comprising:

an entire image storing means for storing an entire area image signal representing a radiation image of an object;

prospective abnormal pattern detecting means for detecting a prospective abnormal pattern in said radiation image in accordance with said entire area image signal;

a judgment means for making a judgment as to the presence or absence of said prospective abnormal pattern in accordance with the results of the detection of said prospective abnormal pattern carried out by said prospective abnormal pattern detecting means;

a local area extracting means for extracting a local area limited image signal corresponding to a local area containing said prospective abnormal pattern from said entire area image signal having been stored in said entire area image storing means, wherein said judgment means has judged that said prospective abnormal pattern is present;

local area limited image displaying means for displaying the image of said local area in accordance with said local area limited image signal, which has been extracted by said local area extracting means; and entire area image displaying means for displaying the entire area of said radiation image of the object in accordance with said entire area image signal, wherein said object is a pair of the right and left mammae and wherein, in cases where said prospective abnormal pattern is detected in one of the mammae, the image of said local area, which contains said prospective abnormal pattern in said one mamma, and an image of a local area in the other mamma, which local area corresponds to the portion of said local area in said one mamma, are displayed together on said local area limited displaying means.

28. An apparatus as defined in claim 27 wherein the same processing for emphasizing the image of the local area is carried out on the images of said local areas in the right and left mammae.

29. An apparatus as defined in claim 28 wherein said entire area image displaying means also serves as said local area limited image displaying means, a pair of the entire area images of the right and left mammae are displayed on said entire area image displaying means, and the images of the corresponding local areas of the right and left mammae are displayed respectively in the entire area images.

30. An apparatus as defined in claim 29 wherein the image of said local area, which is displayed on said entire area image displaying means, is displayed in a display region different from the local area, which is located in said radiation image displayed on said entire area image displaying means and which corresponds to said image of said local area.

31. An apparatus as defined in claim 29 wherein the display region for the image of said local area, which is displayed on said entire area image displaying means, is determined such that it may be accommodated in a display region, which is different from the object image displayed on said entire area image displaying means.

32. An apparatus as defined in claim 31 wherein, in cases where the size of the display region for the image of said local area on said entire area image displaying means is smaller than the size of the image of said local area, only a portion of the image of said local area, which portion is capable of being displayed within the display region for the image of said local area, is displayed, and the image of said local area is scrolled within the display region.

33. An apparatus as defined in claim 28 wherein the image of said local area, which is displayed on said entire area image displaying means, is displayed in a display region different from the local area, which is located in said radiation image displayed on said entire area image displaying means and which corresponds to said image of said local area.

34. An apparatus as defined in claim 28 wherein the display region for the image of said local area, which is displayed on said entire area image displaying means, is determined such that it may be accommodated in a display region, which is different from the object image displayed on said entire area image displaying means.

35. An apparatus as defined in claim 34 wherein, in cases where the size of the display region for the image of said local area on said entire area image displaying means is smaller than the size of the image of said local area, only a portion of the image of said local area, which portion is capable of being displayed within the display region for the image of said local area, is displayed, and the image of said local area is scrolled within the display region.

36. An apparatus as defined in claim 27 wherein said entire area image displaying means also serves as said local area limited image displaying means, a pair of the entire area images of the right and left mammae are displayed on said entire area image displaying means, and the images of the corresponding local areas of the right and left mammae are displayed respectively in the entire area images.

37. An apparatus as defined in claim 36 wherein the image of said local area, which is displayed on said entire area image displaying means, is displayed in a display region different from the local area, which is located in said radiation image displayed on said entire area image displaying means and which corresponds to said image of said local area.

38. An apparatus as defined in claim 36 wherein the display region for the image of said local area, which is displayed on said entire area image displaying means, is determined such that it may be accommodated in a display region, which is different from the object image displayed on said entire area image displaying means.

39. An apparatus as defined in claim 38 wherein, in cases where the size of the display region for the image of said local area on said entire area image displaying means is smaller than the size of the image of said local area, only a portion of the image of said local area, which portion is capable of being displayed within the display region for the image of said local area, is displayed, and the image of said local area is scrolled within the display region.

40. An apparatus as defined in claim 27 wherein the image of said local area, which is displayed on said entire area image displaying means, is displayed in a display region different from the local area, which is located in said radiation image displayed on said entire area image displaying means and which corresponds to said image of said local area.

41. An apparatus as defined in claim 27 wherein the display region for the image of said local area, which is displayed on said entire area image displaying means, is determined such that it may be accommodated in a display region, which is different from the object image displayed on said entire area image displaying means.

42. An apparatus as defined in claim 41 wherein, in cases where the size of the display region for the image of said local area on said entire area image displaying means is smaller than the size of the image of said local area, only a portion of the image of said local area, which portion is capable of being displayed within the display region for the image of said local area, is displayed, and the image of said local area is scrolled within the display region.

43. An apparatus for computer aided diagnosis of images, comprising:

i) an entire area image storing means for storing an entire area image signal representing a radiation image of an object;

ii) an iris filter for calculating the degree of centralization of gradients of said entire area image signal, and thereby detecting an image portion, which is associated with a high degree of centralization, in said radiation image in accordance with said entire area image signal;

iii) a judgment means for-making a judgment as to the presence or absence of said image portion in accordance with the results of the detection of said image portion carried out by said iris filter;

iv) a local area extracting means which, in cases where said judgment means has judged that said image portion is present, extracts a local area limited image signal corresponding to a local area containing said image portion from said entire area image signal having been stored in said entire area image storing means;

v) a local area limited image displaying means for-displaying the image of said local area in accordance with said local area limited image signal, which has been extracted by said local area extracting means;

vi) an entire area image displaying means for displaying the entire area of said radiation image of the object in accordance with said entire area image signal;

vii) a local area limited image emphasizing means for selectively carrying out image emphasis processing on the abnormal pattern image signal, which represents said image portion and is among said local area limited image signal, in accordance with the results of the detection of said image portion carried out by said iris filter, such that said image portion in the image of said local area, which is displayed on said local area limited image displaying means, may have better image quality and higher capability of serving as an effective tool in, particularly, the efficient and accurate diagnosis of an illness than said radiation image, which is displayed on said entire area image displaying means;

viii) local area limited image storing means for temporarily storing said local area limited image signal, said local area limited storing means located between said local area extracting means and said local area limited image displaying means; and ix) local area limited image display requesting means for causing said local area limited image signal to be fed out from said local area limited image storing means and causing the image of said local area to be displayed on said local area limited image displaying means, when a predetermined image display request is received from the exterior, said local area limited image display requesting means being located between said local area extracting means and said local area limited image displaying means.

44. An apparatus as defined in claim 43 wherein said local area limited image emphasizing means comprises an abnormal pattern emphasizing means for carrying out an operation with Formula (1)

$$Dproc = Dorg + \alpha \cdot Giris \quad (1)$$

on the original image signal Dorg, which represents each of picture elements of said radiation image, by using an iris filter signal Giris, which has been obtained from said iris filter in accordance with said degree of centralization with respect to said original image signal Dorg, and an emphasis coefficient $\alpha$.

45. An apparatus as defined in claim 43 wherein said local area limited image emphasizing means comprises:

an unsharp mask signal calculating means for carrying out an operation on the original image signal Dorg, which represents each of picture elements of said radiation image, in order to calculate an unsharp mask signal Dus with respect to an unsharp mask constituted of a picture element matrix, which has a size of N columns×N rows and has its center at the picture element represented by said original image signal Dorg, said unsharp mask signal Dus being calculated with Formula (2)

$$Dus = (\Sigma Dorg)/N^2 \quad (2)$$

wherein $\Sigma Dorg$ represents the sum of the image signal values representing the picture elements located within said unsharp mask.

a conversion table for converting an iris filter signal Giris, which has been obtained from said iris filter in accordance with said degree of centralization, into an emphasis coefficient $\beta(Giris)$ in accordance with said iris filter signal Giris, and an abnormal pattern emphasizing means for carrying out an operation with Formula (3)

$$Dproc = Dorg + \beta(Giris) \cdot (Dorg - Dus) \quad (3)$$

on said original image signal Dorg by using said unsharp mask signal Dus and said emphasis coefficient $\beta(Giris)$.

46. An apparatus for computer aided diagnosis of images, comprising:

i) an entire area image storing means for storing an entire area image signal representing a radiation image of an object;

ii) a morphology filter for detecting an image portion, at which said image signal fluctuates in a spatially narrower range than a predetermined multiply structure element Bi, in said radiation image in accordance with said entire area image signal by using said multiply structure element Bi and a scale factor $\lambda$;

iii) a judgment means for making a judgment as to the presence or absence of said image portion in accordance with the results of the detection of said image portion, at which said image signal fluctuates in a spatially narrower range than said multiply structure element Bi, said detection having been carried out by said morphology filter;

iv) a local area extracting means which, in cases where said judgment means has judged that said image portion is present, extracts a local area limited image signal corresponding to a local area containing said image portion from said entire area image signal having been stored in said entire area image storing means, v) a local area limited image displaying means for displaying the image of said local area in accordance with said local area limited image signal, which has been extracted by said local area extracting means;

vi) an entire area image displaying means for displaying the entire area of said radiation image of the object in accordance with said entire area image signal vii) a local area limited image emphasizing means for selectively carrying out image emphasis processing on the abnormal pattern image signal, which represents said image portion and is among said local area limited image signal, in accordance with the results of the detection of said image portion carried out by said morphology filter, such that said image portion in the image of said local area, which is displayed on said local area limited image displaying means, may have better image quality and higher capability of serving as an effective tool in, particularly, the efficient and accurate diagnosis of an illness than said radiation image, which is displayed on said entire area image displaying means;

viii) local area limited image storing means for temporarily storing said local area limited image signal, said local area limited storing means located between said local area extracting means and said local area limited image displaying means; and ix) local area limited image display requesting means for causing said local area limited image signal to be fed out from said local area limited image storing means and causing the image of said local area to be displayed on said local area limited image displaying means, when a predetermined image display request is received from the exterior, said local area limited image display requesting means being located between said local area extracting means and said local area limited image displaying means.

47. An apparatus as defined in claim 46 wherein said local area limited image emphasizing means comprises:

a conversion table for converting a morphology signal Dmor into an output f(Dmor) in accordance with said morphology signal Dmor, said morphology signal Dmor having been obtained from said morphology filter with respect to the original image signal Dorg, which represents each of picture elements of said radiation image, said morphology signal Dmor representing said image portion, at which said image signal fluctuates in a spatially narrower range than said multiply structure element Bi, and an abnormal pattern emphasizing means for carrying out an operation with Formula (4)

$$Dproc = Dorg + \alpha \cdot f(Dmor) \qquad (4)$$

on said original image signal Dorg by using said output f(Dmor) and an emphasis coefficient $\alpha$.

48. An apparatus as defined in claim 46 wherein said local area limited image emphasizing means comprises:

a conversion table for converting the original image signal Dorg, which represents each of picture elements of said radiation image, into an emphasis coefficient $\beta(Dorg)$ in accordance with said original image signal Dorg, and an abnormal pattern emphasizing means for carrying out an operation with Formula (5)

$$Dproc = Dorg + \beta(Dorg) \cdot (Dorg - Dmor) \qquad (5)$$

on said original image signal Dorg by using a morphology signal Dmor and said emphasis coefficient $\beta(Dorg)$, said morphology signal Dmor having been obtained from said morphology filter and representing said image portion, at which said image signal fluctuates in a spatially narrower range than said multiply structure element Bi.

49. An apparatus as defined in claim 46 wherein said local area limited image emphasizing means comprises:

a conversion table for converting a morphology signal Dmor into an emphasis coefficient $\beta(Dmor)$ in accordance with said morphology signal Dmor, said morphology signal Dmor having been obtained from said morphology filter with respect to the original image signal Dorg, which represents each of picture elements of said radiation image, said morphology signal Dmor representing said image portion, at which said image signal fluctuates in a spatially narrower range than said multiply structure element Bi, and an abnormal pattern emphasizing means for carrying out an operation with Formula (6)

$$Dproc = Dorg + \beta(Dmor) \cdot (Dorg - Dmor) \qquad (6)$$

on said original image signal Dorg by using said emphasis coefficient $\beta(Dmor)$ and a signal, which represents the difference between said original image signal Dorg and said morphology signal Dmor.

50. An apparatus as defined in claim 46 wherein said local area limited image emphasizing means comprises:

an unsharp mask signal calculating means for carrying out an operation on the original image signal Dorg, which represents each of picture elements of said radiation image, in order to calculate an unsharp mask signal Dus with respect to an unsharp mask constituted of a picture element matrix, which has a size of N columns×N rows and has its center at the picture element represented by said original image signal Dorg, said unsharp mask signal Dus being calculated with Formula (2)

$$Dus = (\Sigma Dorg)/N^2 \qquad (2)$$

a conversion table for converting a morphology signal Dmor into an emphasis coefficient $\beta(Dmor)$ in accordance with said morphology signal Dmor, said morphology signal Dmor having been obtained from said morphology filter and representing said image portion, at which said image signal fluctuates in a spatially narrower range than said multiply structure element Bi, and an abnormal pattern emphasizing means for carrying out an operation with Formula (7)

$$Dproc = Dorg + \beta(Dmor) \cdot (Dorg - Dus) \qquad (7)$$

on said original image signal Dorg by using said unsharp mask signal Dus and said emphasis coefficient $\beta(Dmor)$.

* * * * *